(12) United States Patent
McDaniel et al.

(10) Patent No.: US 8,986,965 B2
(45) Date of Patent: Mar. 24, 2015

(54) PRODUCTION OF MONOTERPENES

(75) Inventors: Robert McDaniel, Redwood City, CA (US); Galit Meshulam-Simon, Redwood City, CA (US); Oscar Alvizo, Redwood City, CA (US); Xiyun Zhang, Redwood City, CA (US)

(73) Assignee: Codexis, Inc., Redwood City, CA (US)

( * ) Notice: Subject to any disclaimer, the term of this patent is extended or adjusted under 35 U.S.C. 154(b) by 75 days.

(21) Appl. No.: 13/578,525

(22) PCT Filed: Mar. 30, 2011

(86) PCT No.: PCT/US2011/030606
§ 371 (c)(1),
(2), (4) Date: Oct. 23, 2012

(87) PCT Pub. No.: WO2011/123576
PCT Pub. Date: Oct. 6, 2011

(65) Prior Publication Data
US 2013/0143291 A1    Jun. 6, 2013

Related U.S. Application Data

(60) Provisional application No. 61/319,586, filed on Mar. 31, 2010, provisional application No. 61/319,560, filed on Mar. 31, 2010.

(51) Int. Cl.
*C12P 7/22* (2006.01)
*C12P 5/00* (2006.01)
*C12N 9/10* (2006.01)
*C12N 9/88* (2006.01)

(52) U.S. Cl.
CPC .............. *C12P 5/007* (2013.01); *C12N 9/1085* (2013.01); *C12N 9/88* (2013.01)
USPC .................. 435/166; 435/252.1; 435/252.33; 435/254.11; 435/320.1; 435/252.3; 536/23.2

(58) Field of Classification Search
CPC combination set(s) only.
See application file for complete search history.

(56) References Cited

U.S. PATENT DOCUMENTS

| 3,274,224 | A  | 9/1966  | Collier et al.    |
| 6,806,076 | B1 | 10/2004 | Miyake et al.     |
| 2002/0040488 | A1 | 4/2002  | Chappell et al.   |
| 2008/0318292 | A1 | 12/2008 | Keasling et al.   |
| 2009/0137014 | A1 | 5/2009  | Tsuruta et al.    |

OTHER PUBLICATIONS

Bohlmann et al (Terpenoid Secondary Metabolism in *Arabidopsis thaliana*: cDNA Cloning, Characterization, and Functional Expression of a Myrcene/(E)-b-Ocimene Synthase)Archives of Biochemistry and Biophysics vol. 375, No. 2, Mar. 15, pp. 261±269, 2000.*
Allahverdiev et al., "Kinetics of alpha-Pinene isonnerization," Ind. Eng. Chem. Res., May 1998, vol. 37, pp. 2373-2377.
Bohlmann et al., "Terpenoid Secondary Metabolism in *Arabidopsis thaliana*: cDNA Cloning, Characterization, and Functional Expression of a Myrcene/(E)-,beta-Oclmene Synthase," Arch. Biochem. Biophys., Mar. 15, 2000, vol. 375, No. 2; pp. 261-269.
Hyatt et al., Arch. Biochem. Biophys. 2005, 439:222-223.
Hu et al., "Scope and Mechanism of Intramolecular Aziridination of Cyclopent-3-enylmethylamines to 1-Azatricyclo[2.2.1.0]heptanes with Lead Tetraacetate," J. Amer. Chem. Soc., Aug. 2009, vol. 131, pp. 11998-12006.
Huber et al., Characterization of four terpene synthase cDNAs from methyl jasmonate-induced Douglas-fir, *Pseudotsuga menziesii*, Phytochemistry, 2005, 66: 1427-39.
Huber et al., Uniprot accession Q4QSN3, Sep. 2006 [online], downloaded from http://www.uniport.org/uniport/Q4QSN3.txt?verison=1; downloaded on Sep. 1, 2011.
Lee et al., "Directed evolution of *Escherichia coli* famesyl diphosphate synthase (IspA) reveals novel structural determinants of chain length specificity," Metab. Eng., Jan. 2005, vol. 7, No. 1, pp. 18-26.
Martin et al., Nature Biotechnol, 2003, 21:796-802.
Takahashi, Biotechnol. Bioeng., 2007, 97:170-181.
Venskutonis, effect of drying on the volatile constituents of thyme (*Thymus vulgaris* L.) and sage (*Salvia officinalis* L.), Food Chem., 1997, vol. 59, No. 2, pp. 21-227.
Wise et al., Monoterpene Synthases from Common Sage (*Salvia officinalis*), J. Biol. Chem., 1998, 273(24): 14891-99.

* cited by examiner

*Primary Examiner* — Kagnew H Gebreyesus
(74) *Attorney, Agent, or Firm* — Kilpatrick Townsend & Stockton LLP

(57) ABSTRACT

The present invention relates to methods for producing monoterpenes, particularly tricyclene, by culturing microbial organisms that express a terpene synthase and optionally a prenyl transferase.

17 Claims, 18 Drawing Sheets

Figure 3

Polynucleotide sequence (SEQ ID NO: 1) encoding a bornyl diphosphate synthase (BPS-SOFF).

ATGCGTCGTTCTGGGAACTACCAGCCGGCTCTGTGGGACAGTAATTACATCCAGTCTCTGAACA
CACCTTACACCGAAGAGCGCCATCTGGACCGCAAGGCTGAGCTGATCGTGCAAGTCCGCATCTT
ACTGAAAGAGAAAATGGAACCGGTACAGCAGCTGGAACTGATTCACGATTTGAAATATTTAGGG
CTGTCTGATTTTTTCCAAGATGAGATTAAAGAAATTTTAGGCGTGATCTATAACGAACACAAAT
GTTTTCACAACAACGAAGTGGAAAAAATGGATTTATACTTTACCGCATTGGGTTTCCGCTTATT
GCGTCAGCACGGTTTTAATATTTCTCAGGATGTGTTTAATTGCTTTAAAAACGAAAAAGGCATC
GATTTTAAAGCATCTCTGGCCCAAGATACAAAAGGTATGCTGCAACTGTATGAAGCGTCTTTCC
TGTTACGTAAAGGCGAAGATACTCTGGAGCTGGCGCGTGAATTCGCCACGAAATGCCTGCAGAA
AAAACTGGATGAAGGCGGTAACGAAATCGATGAGAACCTGCTGTTATGGATTCGTCATAGCTTA
GATTTACCGCTGCACTGGCGTATTCAAAGCGTAGAGGCTCGTTGGTTCATCGATGCGTATGCGC
GCCGTCCGGATATGAACCCGCTGATTTTCGAATTGGCCAAACTGAACTTTAACATTATTCAGGC
GACACATCAGCAGGAATTAAAAGATCTGTCTCGCTGGTGGTCTCGCCTGTGCTTCCCGGAAAAA
CTGCCGTTTGTTCGTGACCGTTTAGTAGAATCATTTTTTTGGGCAGTGGGCATGTTCGAACCAC
ACCAGCACGGCTATCAGCGTAAAATGGCCGCGACCATCATTGTCCTGGCGACTGTCATTGATGA
TATTTATGATGTCTACGGTACTCTGGACGAACTGGAACTGTTTACGGATACTTTCAAGCGCTGG
GATACTGAATCTATTACCCGTCTGCCATACTATATGCAACTGTGCTACTGGGGGGTCCACAACT
ATATCTCGGACGCAGCGTATGATATTTTAAAGGAACATGGTTTCTTTTGCCTGCAGTATCTGCG
TAAATCGGTCGTCGATTTGGTTGAAGCATACTTCCACGAAGCTAAGTGGTACCACAGCGGTTAT
ACCCCTTCTTTGGACGAATACCTGAATATTGCGAAAATTTCAGTTGCATCGCCGGCCATTATTT
CCCCGACGTATTTTACATTCGCGAACGCTAGTCATGACACGGCGGTGATCGATTCCCTGTACCA
ATATCATGACATCCTGTGCTTGGCTGGCATTATTCTGCGCCTGCCGGATGATCTGGGCACCTCT
TATTTCGAACTGGCGCGTGGTGACGTACCTAAAACGATCCAGTGTTACATGAAAGAAACCAATG
CATCAGAAGAAGAGGCGGTGGAACACGTTAAATTTCTGATTCGTGAAGCCTGGAAAGACATGAA
TACCGCCATCGCCGCGGGCTATCCGTTTCCGGATGGCATGGTAGCAGGCGCCGCGAACATCGGT
CGTGTGGCCCAGTTCATTTATCTGCACGGTGACGGTTTTGGTGTACAGCACTCTAAAACATATG
AACATATTGCGGGTCTGCTGTTTGAACCGTATGCGTAA

Amino acid sequence of a BPS-SOFF SEQ ID NO: 2.

MRRSGNYQPALWDSNYIQSLNTPYTEERHLDRKAELIVQVRILLKEKMEPVQQLELIHDLKYLG
LSDFFQDEIKEILGVIYNEHKCFHNNEVEKMDLYFTALGFRLLRQHGFNISQDVFNCFKNEKGI
DFKASLAQDTKGMLQLYEASFLLRKGEDTLELAREFATKCLQKKLDEGGNEIDENLLLWIRHSL
DLPLHWRIQSVEARWFIDAYARRPDMNPLIFELAKLNFNIIQATHQQELKDLSRWWSRLCFPEK
LPFVRDRLVESFFWAVGMFEPHQHGYQRKMAATIIVLATVIDDIYDVYGTLDELELFTDTFKRW
DTESITRLPYYMQLCYWGVHNYISDAAYDILKEHGFFCLQYLRKSVVDLVEAYFHEAKWYHSGY
TPSLDEYLNIAKISVASPAIISPTYFTFANASHDTAVIDSLYQYHDILCLAGIILRLPDDLGTS
YFELARGDVPKTIQCYMKETNASEEEAVEHVKFLIREAWKDMNTAIAAGYPFPDGMVAGAANIG
RVAQFIYLHGDGFGVQHSKTYEHIAGLLFEPYA

Figure 4

Polynucleotide sequence (SEQ ID NO: 3) encoding a bornyl diphosphate synthase (BPS-ROFF).

ATGCGTCGTAGCGGTAACTATCAGCCGTCAAGTTGGGATTTCAATTACATCCAAAGCCTTAATA
CCCCATACAAAGAAGAACGTCAACTGAACCGTGAAGCCGAACTTATTGTCCAAGTGAAGATGTT
GCTGAAAGAGAAACGTGAATATGTAAAGCAGTTGGAACTGATTGACGATCTTAAATATTTAGGG
CTGTCTTACTTCTTCCAAGATGAGATTAAAGAAATTCTGGGCTTTATCTATAACGAACACAAAT
GGTTAGACAACAGCGAAGCGGATGAACGTGATTTATACTTAAAGGCATTGGGTTTCCGTATCTT
GCGTCAGCACGGTTTCAATGTTTCTCAGGAAGTGTTTGATTGCTTTAAGAATGAGAAGGGCAGC
GACTTCAAAGCATCTCTGGCCCAAGATACCAAAGGTATTCTGCAACTGTATGAAGCGGCTTTCC
TGTTACGTGAAGGCGAAGATACTCTGGAGCTGGCGCGTGCATTCGCCACGAAATGCTTACAGAA
GAAACTGGATGAAGGCGGTGACGGAATTGATGAGAACCTGCTGTCATGGATTCGTCATAGCTTA
GATTTACCGCTGCACTGGCGTATTCAACGTTTAGAGGCTCGTTGGTTCTTAGATGCGTATGCGC
GTCGTCCGGATATGAACCCGCTGATCTTTGAATTGGCCAAACTGGACTTTAACATTATTCAGGC
GACATATCAGCAGGAATTAAAGGATGTGTCTCGTTGGTGGAATCGTCTGGGCTTAGCGGAGAAA
CTGCCGTTTGTTCGTGACCGTATTGTAGAATCATATTTCTGGGGAGTGGGCATGTTCGAACCAA
ACCAGTACGGCTATCAGCGTAAGATGTCCGGGATCATCATTATGCTGGCGACTGTCATTGATGA
TGTTTATGATGTTTATGGTACTCTGGACGAACTGCAACTGTTTACGGATACTATCCGTAGCTTT
AGTTGGGATACTGAATCTATTTCCCAACTGCCATACTATATGCAACTGTGCTACTTGGCGTTAT
ACAACTTTGTCAGTGAATTAGCGTATGATAATTTAAAGGAACAACATTTCATTTCCATTCCGTA
TCTGCATAAATCCTGGGTCGATTTGGCTGAAGCATACTTGAAGGAAGCTAAGTGGTACTACAGC
GGTTATACCCCTTCTTTGGAAGAATACCTGAGTAATGCGAAGATCTCAATTGCAAGTCCGAACA
TTATTTCCCAGTTGCACTTTACATTAGCGAACTCTAGTACTGACAAGTGGAGTATCGAATCCCT
GTACCAATATCATAACATCCTGAACTTGTCTGGCATGCTTCTGCGTCTGGCGGATGATGTGGGC
ACCGCTCCTTTCGAACTGAAGCGTGGTGACGTACAGAAGGCGATCCAGTGTCACATGAAAGATC
GTAATGCCAGTGAGAAGGAGGCGCAGGAACACGTTATGTTTCTGCTTCGTGAAGCCTGGAAAGA
AATGAATACCGCAATGGCTGATGGCTATCCGTTTGCGGATGAATTGGTAGCAGCCGCCGCGAAC
TTAGGTCGTGTGGCCCAGTTCATGTATCTGGAAGGTGACGGTCATGGTGTACAGCACTCTGGTA
TTCATCAACAAATGGCGGGTCTGCTGTTTGAACCATATACCTAA

Amino acid sequence of a BPS-ROFF, SEQ ID NO: 4.

MRRSGNYQPSSWDFNYIQSLNTPYKEERQLNREAELIVQVKMLLKEKREYVKQLELIDDLKYLG
LSYFFQDEIKEILGFIYNEHKWLDNSEADERDLYLKALGFRILRQHGFNVSQEVFDCFKNEKGS
DFKASLAQDTKGILQLYEAAFLLREGEDTLELARAFATKCLQKKLDEGGDGIDENLLSWIRHSL
DLPLHWRIQRLEARWFLDAYARRPDMNPLIFELAKLDFNIIQATYQQELKDVSRWWNRLGLAEK
LPFVRDRIVESYFWGVGMFEPNQYGYQRKMSGIIIMLATVIDDVYDVYGTLDELQLFTDTIRSF
SWDTESISQLPYYMQLCYLALYNFVSELAYDNLKEQHFISIPYLHKSWVDLAEAYLKEAKWYYS
GYTPSLEEYLSNAKISIASPNIISQLHFTLANSSTDKWSIESLYQYHNILNLSGMLLRLADDVG
TAPFELKRGDVQKAIQCHMKDRNASEKEAQEHVMFLLREAWKEMNTAMADGYPFADELVAAAAN
LGRVAQFMYLEGDGHGVQHSGIHQQMAGLLFEPYT

Figure 5

Polynucleotide sequence (SEQ ID NO: 5) encoding a camphene synthase CamS-PMEN.

ATGCGTCGTGTCGGTAACTATCATTCTAACTTATGGGACGATGATTTCATTAATAGTCTGATCT
CAACTCCTTATGAAGCGCCATCATATCGTGAACGTGGCGAGACGTTGATTGGTGAGGTGAAAGA
AATCTTCAACAGCATTAGCGTGGAGGACGCCGGGGAGTTGATTACCCCGTTAAATGACCTGATC
CAACGTCTGTGGATGGTTGACAGCGTGGAACGTTTAGGCATCGACCGTCACTTCAAAGATGAAA
TCAAGAGTGCACTGGATTATGTATATAGTCATTGGCGTGAAGAAGGCATCGGCTGTGGTCGTGA
GAGTGTAGCAACTGATTTAAATTCTACAGCGTTAGGTCTGCGTACCCTGCGTCTGCATGGTTAT
CCGGTTAGTAGCGACGTGTTAGAACATTTCAAAGACCAGAAAGGGCACTTCGCTTCCTGTTCAA
GCAGTAGTATTGAGACCGGTGGGGAGATTCGTAGCGTGCTGAACCTGTTTCGTGCGAGTCTGAT
TGCGTTCCCAAACGAGAAAGTCATGGACGAAGCCCAAATCTTCTCTACCACGTATTTAAAGGAA
GCCGTGCAGAAGATCCCAGTGAGTTCTCTGTCTCGTCAAATCGAATACGTCATGGAATACGGTT
GGGATACCAACCTGCCACGTCTGGAGGCCCGTCACTACATCCATGTGTTGGGCCAAGACATTAC
CTATAATGATAATGAAATGCCCTATACAAATGTAGAGAAACTGCTGGAATTGGCGAAGCTGGAA
TTTAACATGTTCCATTCTTTGCAACAACGTGAACTGAAACACCTGTCCCGTTGGTGGAAGGATA
GTGGTATGCCAGAAGCGACCTTTACCCGTCATCGTCATGTTGAGTACTATGCCCTGGCAAGTTG
TATCGCGTTTGAACCGCAGCACAGTGGGTTCCGATTCGGCTTTGCGAAATTATGCCACATTATT
ACCGTGCTGGATGACATGTATGATTTATTCGGCACCATTGATGAGCTGGAACTGTTTACCGCCG
CCATTAAACGTTGGGACCCTAGTGCCACCGACTGCTTACCGGAATATATGAAAGGTGTGTACAC
TATGGTTTATGATACTATCAATGAGATGGCAGGCGAGGCCCAGAATGCACAGGGCCGTGACACA
TTGAACTACGCACGTGAAGCGTGGGAAGCCTGTTTAGATTCCTATTTGCAGGAGGCCAAATGGA
TTGCAACCGGGTATCTGCCTAGCTTTGAAGAGTACTATGAGAATGGTAAAGTCAGTAGTGCTCA
CCGTGTCTGCACCTTACAGCCGATTCTGACGTTGGATATTCCATTTCCTGATCATATTCTGAAA
GAGGTGGATTTCCCGTCTAAACTGAACGACCTGGCCTGCGCCGTTCTGCGTCTGCGTGGTGATA
CCCGTTGTTATCAGGCCGACCGTGCGCGTGGTGAAGAAGCCAGTTCTATTTCATGTTACATGAA
GGATAATCCAGGTTCCACTGAAGAAGATGCGCTGAACCACATCAATGCCATGCTTAGTGACGTT
ATCAAGGAACTGAACTGGGAACTGTTGAAGCCTGACAGCGTGCCGATTAGCGCTAAGAAACATG
CGTATGATGTCAGTCGTGCATTCCATTACGGCTACAAATACCGTGACGGTTATAGCGTGGCTAA
TATTGAAATTAAGAACTTCGTGGCTATTAGTGTGCTGGAACCCGTATAA

Amino acid sequence of CamS-PMEN SEQ ID NO: 6.

MRRVGNYHSNLWDDDFINSLISTPYEAPSYRERGETLIGEVKEIFNSISVEDAGELITPLNDLI
QRLWMVDSVERLGIDRHFKDEIKSALDYVYSHWREEGIGCGRESVATDLNSTALGLRTLRLHGY
PVSSDVLEHFKDQKGHFASCSSSSIETGGEIRSVLNLFRASLIAFPNEKVMDEAQIFSTTYLKE
AVQKIPVSSLSRQIEYVMEYGWDTNLPRLEARHYIHVLGQDITYNDNEMPYTNVEKLLELAKLE
FNMFHSLQQRELKHLSRWWKDSGMPEATFTRHRHVEYYALASCIAFEPQHSGFRFGFAKLCHII
TVLDDMYDLFGTIDELELFTAAIKRWDPSATDCLPEYMKGVYTMVYDTINEMAGEAQNAQGRDT
LNYAREAWEACLDSYLQEAKWIATGYLPSFEEYYENGKVSSAHRVCTLQPILTLDIPFPDHILK
EVDFPSKLNDLACAVLRLRGDTRCYQADRARGEEASSISCYMKDNPGSTEEDALNHINAMLSDV
IKELNWELLKPDSVPISAKKHAYDVSRAFHYGYKYRDGYSVANIEIKNFVAISVLEPV*

FIGURE 9

>BR5-CAMS-AGR (SEQ ID 7)
ATGCGTCGTGTGGGTAATTACCACTCAAACTTGTGGGATGATGACTTTATTCAAAGTCTGATTAGCACGCCTTA
CGGAGCCCCCGACTATCGTGAACGTGCCGATCGTTTAATTGGTGAGGTGAAAGACATTATGTTCAACTTCAAG
AGCTTGGAGGACGGGGGGAATGACCTGTTACAACGTCTGTTGTTAGTTGACGACGTGGAACGTTTAGGCATC
GACCGTCACTTCAAGAAAGAAATCAAGACCGCACTGGATTATGTAAATAGTTATTGGAACGAGAAGGGCATC
GGCTGTGGTCGTGAGAGTGTAGTAACTGATTTAAATTCTACAGCGTTAGGTCTGCGTACCCTGCGTCTGCATG
GTTATACGGTTAGTAGCGACGTGTTAAATGTGTTTAAAGACAAGAATGGGCAGTTTAGTTCCACTGCAAACAT
TCAGATCGAAGGGGAGATTCGTGGCGTGCTGAACCTGTTTCGTGCGAGTCTGGTTGCGTTCCCAGGCGAGAA
AGTCATGGACGAAGCCGAAACTTTCTCTACCAAGTATTTACGTGAAGCCTTACAGAAGATCCCAGCGAGTTCT
ATTCTGTCTCTTGAAATCCGTGATGTTCTGGAATACGGTTGGCATACCAACCTGCCACGTCTGGAGGCCCGTAA
CTACATGGATGTCTTTGGCCAACACACGAAGAACAAGAACGCAGCAGAGAAGCTGCTGGAATTGGCGAAGCT
GGAATTTAACATCTTTCATTCTTTGCAAGAACGTGAACTGAAACACGTGTCCCGTTGGTGGAAGGATAGTGGT
TCTCCAGAAATGACTTTCTGTCGTCATCGTCATGTTGAGTACTATGCCCTGGCAAGTTGTATCGCGTTTGAACC
GCAGCACAGTGGGTTCCGTTTGGGCTTTACGAAGATGTCCCACCTGATTACCGTGCTGGATGACATGTATGAT
GTCTTCGGCACCGTCGATGAGCTGGAACTGTTTACTGCAACCATTAAACGTTGGGACCCTAGTGCAATGGAAT
GCTTACCGGAATATATGAAAGGTGTGTACATGATGGTTTATCATACTGTCAATGAGATGGCACGTGTGGCCGA
GAAAGCACAGGGCCGTGACACATTGAACTACGCACGTCAAGCGTGGGAAGCCTGTTTCGATTCCTATATGCA
GGAGGCCAAATGGATTGCAACCGGGTATCTGCCTACCTTTGAAGAGTACTTAGAGAATGGTAAAGTCAGTAG
TGCTCACCGTCCCTGCGCCTTACAGCCGATTCTGACGTTGGATATTCCATTTCCTGATCATATTCTGAAAGAGGT
GGATTTCCCGTCTAAACTGAACGACCTGATCTGCATCATTCTGCGTCTGCGTGGTGATACCCGTTGTTATAAGG
CCGACCGTGCGCGTGGTGAAGAAGCCAGTTCTATTTCATGTTACATGAAGGATAATCCAGGTTTAACTGAAGA
AGATGCGCTGAACCACATCAATTTCATGATTCGTGACGCTATCCGTGAACTGAACTGGGAACTGTTGAAGCCT
GACAATAGCGTGCCGATTACCTCCAAGAAGCATGCGTTTGATATTAGTCGTGTATGGCATCACGGCTACCGTT
ACCGTGACGGTTATAGCTTTGCTAATGTGGAAACAAAGTCTCTGGTGATGCGTACTGTGATTGAACCCGTACC
ACTG

>BR5-CAMS-AGR (SEQ ID 8)

MRRVGNYHSNLWDDDFIQSLISTPYGAPDYRERADRLIGEVKDIMFNFKSLEDGGNDLLQRLLLVDDVER

LGIDRHFKKEIKTALDYVNSYWNEKGIGCGRESVVTDLNSTALGLRTLRLHGYTVSSDVLNVFKDKNGQF

SSTANIQIEGEIRGVLNLFRASLVAFPGEKVMDEAETFSTKYLREALQKIPASSILSLEIRDVLEYGWHT

NLPRLEARNYMDVFGQHTKNKNAAEKLLELAKLEFNIFHSLQERELKHVSRWWKDSGSPEMTFCRHRHVE

YYALASCIAFEPQHSGFRLGFTKMSHLITVLDDMYDVFGTVDELELFTATIKRWDPSAMECLPEYMKGVY

MMVYHTVNEMARVAEKAQGRDTLNYARQAWEACFDSYMQEAKWIATGYLPTFEEYLENGKVSSAHRPCAL

QPILTLDIPFPDHILKEVDFPSKLNDLICIILRLRGDTRCYKADRARGEEASSISCYMKDNPGLTEEDAL

NHINFMIRDAIRELNWELLKPDNSVPITSKKHAFDISRVWHHGYRYRDGYSFANVETKSLVMRTVIEPVP

>BR1-TPS10 (SEQ ID 9)

ATGCGCCGCTCGGCGAACTACCAGCCGTCCCGCTGGGATCACCACCACCTGCTGTCGGTGGAAAATAAGTTCG
CCAAAGACAAACGCGTTCGCGAGCGCGATCTGTTAAAAGAAAAAGTACGTAAAATGTTGAACGACGAACAGA
AAACCTATCTGGACCAGCTGGAATTTATTGACGACTTGCAGAAGTTGGGCGTGTCGTACCACTTTGAGGCAGA
GATTGACAATATTCTGACGTCCTCATACAAAAAGGACCGCACCAACATTCAGGAAAGTGATCTGCATGCCACA
GCTCTGGAATTTCGTCTGTTCCGCCAGCATGGTTTCAACGTTAGCGAAGACGTGTTTGATGTATTTATGGAAAA
CTGCGGCAAATTCGATCGTGATGACATCTACGGTCTGATCAGTTTATATGAGGCTTCCTATCTGTCTACGAAAT
TGGATAAGAATCTGCAAATCTTTATTCGTCCGTTTGCTACGCAGCAGCTGCGCGATTTCGTGGATACACACTCC
AACGAAGACTTCGGTTCGTGTGACATGGTTGAAATTGTTGTACAGGCTCTGGATATGCCATACTACTGGCAGA
TGCGTCGTTTATCGACCCGCTGGTATATTGACGTCTACGGTAAACGTCAAAATTACAAGAATCTGGTAGTTGTT
GAATTTGCAAAAATTGACTTTAACATCGTCCAGGCCATTCACCAGGAGGAACTGAAAAACGTGTCATCGTGGT
GGATGGAAACAGGTCTGGGGAAGCAGCTGTACTTTGCCCGCGACCGTATCGTAGAAAACTACTTTTGGACCA
TTGGCCAAATTCAAGAACCGCAGTATGGTTACGTTCGTCAAACAATGACGAAAATCAATGCGTTGTTAACGAC
TATCGATGACATCTATGATATCTACGGCACGTTGGAAGAACTGCAACTGTTCACTGTCGCATTCGAAAACTGG
GACATCAACCGCCTGGATGAACTGCCGGAATACATGCGTCTGTGCTTTCTGGTCATCTACAACGAAGTGAACT
CAATCGCGTGCGAAATTCTGCGTACGAAAAACATCAACGTTATTCCTTTTTTGAAAAAAAGCTGGACCGACGTT
TCTAAGGCATATCTGGTTGAAGCTAAATGGTATAAATCTGGCCACAAACCGAATCTGGAAGAATACATGCAGA
ATGCGCGCATTAGTATTTCCAGTCCGACTATCTTCGTGCACTTTTACTGCGTATTCTCTGACCAACTGAGTATCC
AAGTTCTGGAAACCTTAAGCCAGCACCAACAGAATGTGGTTCGTTGCAGTTCTTCAGTTTTCCGTCTGGCAAC
GACTTAGTAACTTCCCCGGATGAATTGGCCCGTGGCGATGTGTGCAAATCGATCCAATGTTACATGTCCGAAA
CGGGTGCCTCTGAAGATAAAGCACGCAGTCACGTCCGCCAGATGATTAATGATCTGTGGGATGAGATGAATT
ATGAAAAAATGGCCCATTCATCTTCTATTCTGCACCACGATTTTATGGAAACGGTGATCAACTTAGCCCGCATG
TCGCAGTGCATGTATCAGTATGGCGATGGCCACGGGTCTCCGGAAAAAGCGAAAATTGTCGACCGTGTCATG
TCACTGCTGTTTAATCCTATTCCGCTGGAT

>BR1-TPS10 (SEQ ID 10)

MRRSANYQPSRWDHHHLLSVENKFAKDKRVRERDLLKEKVRKMLNDEQKTYLDQLEFIDDLQKLGVSYHF

EAEIDNILTSSYKKDRTNIQESDLHATALEFRLFRQHGFNVSEDVFDVFMENCGKFDRDDIYGLISLYEA

SYLSTKLDKNLQIFIRPFATQQLRDFVDTHSNEDFGSCDMVEIVVQALDMPYYWQMRRLSTRWYIDVYGK

RQNYKNLVVVEFAKIDFNIVQAIHQEELKNVSSWWMETGLGKQLYFARDRIVENYFWTIGQIQEPQYGYV

RQTMTKINALLTTIDDIYDIYGTLEELQLFTVAFENWDINRLDELPEYMRLCFLVIYNEVNSIACEILRT

KNINVIPFLKKSWTDVSKAYLVEAKWYKSGHKPNLEEYMQNARISISSPTIFVHFYCVFSDQLSIQVLET

LSQHQQNVVRCSSSVFRLANDLVTSPDELARGDVCKSIQCYMSETGASEDKARSHVRQMINDLWDEMNYE

KMAHSSSILHHDFMETVINLARMSQCMYQYGDGHGSPEKAKIVDRVMSLLFNPIPLD

FIGURE 11

> BR2-LS-MSPI (SEQ ID 11)
ATGCGTCGTAGTGGTAATTATAATCCATCACGTTGGGATGTGAACTTTATTCAGAGTTTATTATCAGATTATAA
AGAAGACAAACATGTCATTCGTGCTTCAGAATTAGTTACACTGGTCAAGATGGAGTTAGAGAAGGAGACGGA
TCAGATTCGTCAGCTGGAATTGATTGATGATCTTCAACGTATGGGTCTGTCAGACCACTTTCAGAACGAATTTA
AAGAGATCTTATCCTCCATTTATCTTGACCACCATTACTACAAGAACCCATTTCCTAAAGAGGAACGTGATTTGT
ACAGTACCTCCCTTGCCTTTCGTTTATTGCGTGAACACGGCTTTCAGGTTGCTCAGGAAGTGTTTGATTCTTTCA
AGAATGAAGAGGGAGAATTTAAAGAATCCTTGTCCGATGACACTCGTGGTTTACTTCAACTGTACGAAGCATC
CTTCTTATTAACCGAAGGCGAGACTACCTTAGAAAGTGCGCGTGAATTTGCAACGAAATTCTTGGAGGAGAAG
GTTAACGAAGGCGGTGTGGACGGGGATTTACTTACCCGTATTGCCTATTCTCTTGATATTCCACTGCATTGGCG
TATTAAACGTCCGAACGCACCAGTTTGGATCGAATGGTATCGTAAACGTCCAGATATGAATCCGGTTGTCTTA
GAGTTAGCCATTCTTGATCTGAACATTGTACAAGCCCAGTTCCAAGAGGAATTGAAAGAAAGTTTCCGTTGGT
GGCGTAACACGGGTTTCGTAGAGAAATTACCATTCGCCCGTGATCGTTTAGTCGAATGTTACTTCTGGAACAC
CGGGATTATCGAGCCTCGTCAGCATGCGTCAGCCCGTATTATGATGGGTAAAGTCAACGCCCTGATTACCGTT
ATTGATGATATTTATGATGTTTATGGTACACTTGAAGAGCTTGAGCAGTTTACTGACCTGATTCGTCGTTGGGA
TATTAATTCAATTGATCAGCTGCCGGATTACATGCAGTTGTGCTTCCTTGCTTTGAATAATTTCGTAGATGACAC
ATCCTACGATGTCATGAAAGAGAAAGGGGTGAATGTCATTCCTTATCTTCGTCAATCATGGGTAGATTTAGCA
GATAAATACATGGTTGAAGCTCGTTGGTTCTACGGTGGACACAAACCCAGCTTAGAAGAATACTTGGAGAACT
CATGGCAAAGTATCAGCGGCCCTTGTATGTTAACCCACATCTTCTTCCGTGTTACCGACTCCTTCACTAAGGAA
ACCGTCGATTCTCTTTATAAATATCATGATCTGGTACGTTGGTCTAGCTTTGTGTTACGTTTGGCAGACGATCTT
GGGACATCCGTCGAGGAAGTGTCTCGTGGAGATGTACCGAAATCATTACAATGTTACATGTCTGATTACAACG
CATCCGAAGCTGAAGCCCGTAAGCATGTGAAGTGGTTAATCGCAGAAGTCTGGAAGAAGATGAATGCAGAGC
GTGTGAGTAAGGACTCTCCCTTTGGCAAAGACTTTATTGGATGTGCTGTTGACTTAGGTCGTATGGCTCAGTTA
ATGTATCATAACGGTGATGGTCATGGCACTCAGCACCCGATTATTCACCAACAAATGACCCGTACCCTGTTTGA
ACCGTTCGCA

>BR2-LS-MSPI (SEQ ID 12)

MRRSGNYNPSRWDVNFIQSLLSDYKEDKHVIRASELVTLVKMELEKETDQIRQLELIDDLQRMGLSDHFQ

NEFKEILSSIYLDHHYYKNPFPKEERDLYSTSLAFRLLREHGFQVAQEVFDSFKNEEGEFKESLSDDTRG

LLQLYEASFLLTEGETTLESAREFATKFLEEKVNEGGVDGDLLTRIAYSLDIPLHWRIKRPNAPVWIEWY

RKRPDMNPVVLELAILDLNIVQAQFQEELKESFRWWRNTGFVEKLPFARDRLVECYFWNTGIIEPRQHAS

ARIMMGKVNALITVIDDIYDVYGTLEELEQFTDLIRRWDINSIDQLPDYMQLCFLALNNFVDDTSYDVMK

EKGVNVIPYLRQSWVDLADKYMVEARWFYGGHKPSLEEYLENSWQSISGPCMLTHIFFRVTDSFTKETVD

SLYKYHDLVRWSSFVLRLADDLGTSVEEVSRGDVPKSLQCYMSDYNASEAEARKHVKWLIAEVWKKMNAE

RVSKDSPFGKDFIGCAVDLGRMAQLMYHNGDGHGTQHPIIHQQMTRTLFEPFA

FIGURE 12

>BR3-SS-SOFF (SEQ ID 13)

ATGCGTCGCTCGGGCGATTACCAACCTTCTTTATGGGACTTTAATTATATCCAGTCTCTGAACACCCCATATAAA
GAGCAGCGCCATTTCAACCGTCAGGCTGAACTGATTATGCAGGTTCGTATGCTGCTGAAGGTGAAGATGGAA
GCAATTCAGCAGCTGGAACTGATTGACGATCTGCAGTATCTGGGTCTGAGCTACTTCTTTCAGGATGAAATCA
AACAAATTCTGAGCTCTATTCACAACGAACCACGCTATTTTCACAATAACGACTTGTATTTCACGGCACTGGGT
TTCCGCATTTTACGCCAGCATGGGTTCAACGTGTCAGAAGACGTATTCGACTGTTTTAAAATTGAAAAGTGCTC
TGATTTCAACGCGAACCTGGCCCAAGATACGAAAGGCATGCTGCAGCTGTATGAAGCAAGCTTTTTATTACGT
GAAGGTGAAGATACTTTAGAGCTGGCGCGTCGCTTCAGCACCCGTAGCCTGCGTGAAAAGTTTGATGAGGGT
GGTGATGAAATCGATGAAGATTTATCCAGCTGGATTCGTCATTCGCTGGACTTACCGTTGCACTGGCGCGTCC
AAGGGCTGGAAGCACGCTGGTTCCTGGATGCGTATGCCCGTCGTCCGGATATGAATCCACTGATCTTCAAACT
GGCGAAATTAAACTTTAATATTGTGCAGGCCACGTACCAGGAGGAGTTAAAAGATATCTCACGTTGGTGGAA
CAGTAGCTGCTTAGCGGAGAAATTGCCGTTTGTACGTGATCGCATTGTGGAATGTTTTTTTTGGGCTATTGCG
GCATTCGAACCACACCAGTATTCGTACCAACGTAAAATGGCGGCTGTAATTATCACTTTTATCACGATCATTGA
CGATGTCTATGATGTATACGGCACTATCGAGGAACTGGAGTTACTGACCGACATGATCCGTCGCTGGGATAAT
AAATCGATTTCGCAACTGCCGTATTATATGCAAGTTTGTTATCTGGCTCTGTACAACTTTGTATCTGAGCGTGCT
TACGATATCTTAAAAGACCAGCACTTCAACAGCATCCCGTACTTACAGCGTTCGTGGGTTTCTTTGGTAGAAGG
GTATTTAAAGGAAGCATATTGGTACTATAACGGCTACAAACCGTCGCTGGAAGAATACCTGAATAATGCGAAA
ATTTCCATTTCAGCTCCGACTATTATTAGCCAACTGTATTTTACCCTGGCGAATAGTATCGATGAGACTGCTATC
GAGAGCTTGTATCAGTATCACAACATCCTGTATTTGTCGGGGACCATCTTACGCCTGGCCGACGATCTGGGCA
CTTCGCAACATGAGTTGGAGCGCGGGGATGTGCCGAAAGCGATTCAATGTTACATGAACGATACAAATGCGT
CGGAACGCGAGGCAGTAGAACACGTTAAATTTCTGATCCGTGAAGCGTGGAAGGAAATGAACACTGTTACCA
CCGCTTCCGATTGTCCTTTCACCGATGACCTGGTTGCTGCTGCCGCGAATTTGGCTCGTGCAGCGCAGTTCATT
TACCTGGATGGTGACGGGCATGGCGTGCAGCACTCTGAAATTCATCAGCAGATGGGCGGCCTGCTGTTCCAA
CCGTACGTA

>BR3-SS-SOFF (SEQ ID 14)

MRRSGDYQPSLWDFNYIQSLNTPYKEQRHFNRQAELIMQVRMLLKVKMEAIQQLELIDDLQYLGLSYFFQ

DEIKQILSSIHNEPRYFHNNDLYFTALGFRILRQHGFNVSEDVFDCFKIEKCSDFNANLAQDTKGMLQLY

EASFLLREGEDTLELARRFSTRSLREKFDEGGDEIDEDLSSWIRHSLDLPLHWRVQGLEARWFLDAYARR

PDMNPLIFKLAKLNFNIVQATYQEELKDISRWWNSSCLAEKLPFVRDRIVECFFWAIAAFEPHQYSYQRK

MAAVIITFITIIDDVYDVYGTIEELELLTDMIRRWDNKSISQLPYYMQVCYLALYNFVSERAYDILKDQH

FNSIPYLQRSWVSLVEGYLKEAYWYYNGYKPSLEEYLNNAKISISAPTIISQLYFTLANSIDETAIESLY

QYHNILYLSGTILRLADDLGTSQHELERGDVPKAIQCYMNDTNASEREAVEHVKFLIREAWKEMNTVTTA

SDCPFTDDLVAAAANLARAAQFIYLDGDGHGVQHSEIHQQMGGLLFQPYV

FIGURE 13

>BR6-PS-AANN (SEQ ID 15)

ATGCGTCGTAGTGCAAATTACGCCCCTTCACTGTGGAGTTATGACTTCGTTCAATCGCTGTCCTCAAAATACAA
AGGGGATAACTACATGGCGCGTTCGCGCGCGTTGAAAGGTGTAGTGCGCACTATGATCCTGGAAGCGAATGG
CATCGAAAACCCATTGTCATTGCTGAACCTGGTGGACGACTTGCAGCGCTTAGGCATTTCATACCATTTCCTGG
ACGAGATCTCCAACGTTCTGGAAAAAATCTACCTGAACTTCTATAAAAGCCCGGAAAAATGGACTAACATGGA
CTTGAATTTACGTTCTCTGGGCTTCCGCTTACTGCGTCAACACGGTTATCATATTCCTCAGGAAATCTTTAAGGA
TTTCATCGATGTCAACGGCAATTTTAAAGGTGATATCATCAGTATGCTGAATCTGTATGAAGCGTCGTACCACT
CAGTAGAAGAGGAATCCATTCTGGATGATGCCCGCGAATTCACCACGAAATATCTGAAAGAGACCCTGGAGA
ACATTGAAGATCAAAACATTGCTTTGTTCATTAGCCATGCCTTAGTTTTCCCGCTGCATTGGATGGTTCCGCGC
GTCGAAACGTCATGGTTTATTGAAGTCTACCCGAAAAAGGTGGGCATGAATCCGACAGTCCTGGAGTTTGCAA
AACTGGATTTTAATATTCTGCAAGCTGTACATCAGGAGGATATGAAGAAAGCCTCACGCTGGTGGAAAGAAA
CCTGCTGGGAGAAGTTTGGCTTCGCTCGCGATCGTCTGGTCGAAAACTTTATGTGGACCGTCGCTGAGAACTA
TTTACCGCACTTTCAGACCGGCCGTGGCGTCCTGACGAAAGTGAATGCTATGATTACCACCATTGACGACGTTT
ATGATGTGTATGGTACTCTGCCAGAACTGGAACTGTTTACCAACATTGTTAATTCTTGGGATATCAATGCGATC
GATGAACTGCCGGATTATCTGAAAATTTGCTTCCTGGCGTGTTACAATGCCACCAATGAACTGAGCTACAACA
CCCTGACCAACAAAGGTTTTTTTGTTCATCCATACTTAAAAAAAGCCTGGCAGGACTTGTGCAACAGCTATATT
ATTGAAGCTAAGTGGTTTAACGATGGTTACACTCCGACGTTTAACGAATTCATTGAAAACGCTTACATGTCCAT
CGGGATTGCGCCGATCATCCGTCACGCTTACCTGCTGACTCTGACATCCGTGACGGAGGAAGCACTGCAGCAC
ATCGAACGTGCGGAATCAATGATTCGTAACGCGTGCCTGATTGTGCGTCTGACTAACGACATGGGTACGTCAA
GCGACGAACTGGAGCGTGGTGACATTCCTAAGAGCATCCAGTGCTACATGCACGAATCGGGTGCAACCGAAA
TGGAAGCTCGTGCTTACATCAAACAGTTCATTGTTGAAACGTGGAAAAAATTGAACAAGGAACGTCAAGAAAT
CGGTAGCGAATTCCCACAAGAATTCGTTGATTGCGTAATTAATCTGCCGCGCATGGGTCACTTCATGTATACG
GATGGTGATAAACACGGTAAACCGGAGATGTTCAAACCGTATGTCTTTAGTCTGTTCGTGAATCCTATT

>BR6-PS-AANN (SEQ ID 16)

MRRSANYAPSLWSYDFVQSLSSKYKGDNYMARSRALKGVVRTMILEANGIENPLSLLNLVDDLQRLGISY

HFLDEISNVLEKIYLNFYKSPEKWTNMDLNLRSLGFRLLRQHGYHIPQEIFKDFIDVNGNFKGDIISMLN

LYEASYHSVEEESILDDAREFTTKYLKETLENIEDQNIALFISHALVFPLHWMVPRVETSWFIEVYPKKV

GMNPTVLEFAKLDFNILQAVHQEDMKKASRWWKETCWEKFGFARDRLVENFMWTVAENYLPHFQTGRGVL

TKVNAMITTIDDVYDVYGTLPELELFTNIVNSWDINAIDELPDYLKICFLACYNATNELSYNTLTNKGFF

VHPYLKKAWQDLCNSYIIEAKWFNDGYTPTFNEFIENAYMSIGIAPIIRHAYLLTLTSVTEEALQHIERA

ESMIRNACLIVRLTNDMGTSSDELERGDIPKSIQCYMHESGATEMEARAYIKQFIVETWKKLNKERQEIG

SEFPQEFVDCVINLPRMGHFMYTDGDKHGKPDMFKPYVFSLFVNPI

FIGURE 14

>BR7-FS-OBAS (SEQ ID 17)
ATGCGTCGTAGTGGTAATTACCAGCCTTCCGCCTGGGATTTCAATTATATCCAATCTCTTAACAATAATCACTCC
AAAGAAGAGCGTCATTTACAGGGTAAAGCTAAATTGATCGAGGAAGTCAAGATGTTACTGGAACAAGAAATG
GCAGCGGTACAGCAGCTGGAATTTATCGAGGATTTGAAGAACTTAGGGCTGTCTTATTTATTCCAAGATGAGA
TTAAGATTATCTTGAACAGTATCTATAACCATCACAAATGTTTCCACAACAACCATCAGCAACGTACCGATGAG
AATGCGGATTTATACTTTGTCGCATTGGGTTTCCGTTTATTTCGTCAGCACGGTTTCAAAGTTTCTCAGGAAGT
GTTTGATTGCTTTAAGAACGAAGAAGGCAGCGACTTCATTCCAAATCTGGCCGAAGATACCAAAGGTTTGCTG
CAACTGTATGAAGCGTCTTACCTGGTACGTCAAGACGAAGATACTCTGGAGATGGCGCGTCAATTCTCCACGA
AGATCTTGCAGAAGAAAGTGGAAGAGAAGATGATCGAAGAGAACCTGCTGTCATGGACTTGTCATAGCTTAG
AATTACCGCTGCACTGGCGTGTTCAACGTATTGAGGCTAAATGGTTCTTAGATGCGTATGCGAGCAAACCGGA
TATGAACCCGATTATCTTTGAATTGGCCAAACTGGAATTTAACATTGCTCAGGCGTTACAACAGGGGGAATTA
AAGGATCTGTCTCGTTGGTGGAATGACACGGGCATCGCGGAGAAACTGCCGTTTGCTCGTGACCGTATTGTA
GAAGCACATTATTGGGCAATTGGCACGTTAGAACCATACCAGTACCGTTATCAGCGTAGTTTGATCGCGAAGA
TCATTGCCCTGACGACTGTCGTTGATGATGTTTATGATGTTTATGGTACTCTGGACGAACCGCAACTGTTTACG
GATGCTATCCGTCGTTGGGATATTGAATCTATTAACCAACTGCCACACTATTTGCAACTGTGCTACTTGGCGAT
CTACAACTTTGTCAGTGAATTAGCGTATGATATCTTCCGTGATAAAGGTTTCAATTCCCTGCCGTATCTGCATAA
GAGTTGGTTAGATTTGGTTGAAGCATACTTCTTAGAAGCTAAGTGGTTCCACAGCGGTTATACCCCTACTTTGG
AAGAATACCTGAATAATAGTAAGATGACAATTACATGTCCGGCCATTGTTTCCGAGATTTACTTCGCATTCGCG
AACAGTATTGACAAGACGGAGGTCGAATCCGTGTACAAATATCATGACATCCTGTACTTGTCTGGCATGCTTCT
GCGTCTGCCGGATGATCTGGGCACCACTACTTTCGAAATGAAGCGTGGTGACGTAGCTAAAGCGATCCAGTG
TTACATGAAAGAACACAATGCCAGTGAAGAAGAGGCGCGTGAACACATTCGTTTCCTGATGCGTGAAGCCTG
GAAACAAATGAATACCGCCGCCGCCGCCAATAACTGTCCGTTTGTGAATGACTTTGTAGTAGGCGCCGCGAGC
TTAGGTCGTGTGGCCAATTTCGTTTATGTGGAAGGTGACGGTTTCGGTGTACAGCACTCTAAGATCCATCAAC
AAATGGCGGAACTGCTGTTCTACCCGTATCAG

>BR7-FS-OBAS (SEQ ID 18)

MRRSGNYQPSAWDFNYIQSLNNNHSKEERHLQGKAKLIEEVKMLLEQEMAAVQQLEFIEDLKNLGLSYLF

QDEIKIILNSIYNHHKCFHNNHQQRTDENADLYFVALGFRLFRQHGFKVSQEVFDCFKNEEGSDFIPNLA

EDTKGLLQLYEASYLVRQDEDTLEMARQFSTKILQKKVEEKMIEENLLSWTCHSLELPLHWRVQRIEAKW

FLDAYASKPDMNPIIFELAKLEFNIAQALQQGELKDLSRWWNDTGIAEKLPFARDRIVEAHYWAIGTLEP

YQYRYQRSLIAKIIALTTVVDDVYDVYGTLDEPQLFTDAIRRWDIESINQLPHYLQLCYLAIYNFVSELA

YDIFRDKGFNSLPYLHKSWLDLVEAYFLEAKWFHSGYTPTLEEYLNNSKMTITCPAIVSEIYFAFANSID

KTEVESVYKYHDILYLSGMLLRLPDDLGTTTFEMKRGDVAKAIQCYMKEHNASEEEAREHIRFLMREAWK

QMNTAAAANNCPFVNDFVVGAASLGRVANFVYVEGDGFGVQHSKIHQQMAELLFYPYQ

FIGURE 15

>BR8-CS-SFRU (SEQ ID 19)

ATGCGTCGTACCGGAGGGTATCAACCTACTTTGTGGGATTTCAGCACTATTCAATCATTTGATAGCGAATATAA
AGAAGAGAAACATTTAATGCGTGCTGCGGGCATGATTGATCAGGTGAAGATGATGCTTCAAGAAGAAGTTGA
TTCTATTCGTCGTTTGGAACTGATTGACGATTTGCGTCGTCTGGGGATTTCATGCCACTTTGAACGTGAAATCG
TGGAAATCTTGAACTCCAAATATTACACGAACAACGAAATTGACGAGCGTGATCTTTACAGCACCGCATTGCG
ATTCCGTTTATTACGTCAATACGATTTCAGTGTTAGTCAGGAGGTGTTTGATTGCTTTAAGAACGCCAAAGGTA
CGGACTTTAAACCTAGTTTAGTTGATGATACTCGTGGTTTACTTCAACTGTACGAAGCATCCTTTCTTAGTGCCC
AGGGCGAGGAAACCTTGCGTTTAGCGCGTGACTTCGCAACGAAGTTCTTGCAGAAACGTGTGCTGGTGGACA
AAGATATTAATTTATTATCCTCTATTGAGCGTGCACTGGAACTGCCGACTCACTGGCGTGTTCAAATGCCAAAT
GCACGTTCTTTCATTGATGCCTATAAACGTCGTCCAGACATGAACCCAACCGTACTTGAACTGGCAAAGTTGGA
TTTCAATATGGTCCAAGCACAGTTTCAGCAAGAATTAAAGGAAGCCAGTCGTTGGTGGAACAGTACCGGACTT
GTTCATGAGTTGCCCTTTGTTCGTGATCGTATTGTGGAGTGTTACTACTGGACGACTGGCGTGGTGGAGCGTC
GTCAGCATGGTTACGAACGTATCATGTTGACCAAGATTAATGCACTGGTTACGACGATTGATGATGTATTCGA
CATTTATGGCACGCTTGAGGAGCTTCAGCTGTTCACCACGGCGATTCAACGTTGGGACATCGAATCAATGAAG
CAACTGCCGCCTTACATGCAGATCTGTTACCTTGCTTTGTTTAATTTCGTAAACGAGATGGCTTATGACACTCTT
CGTGATAAAGGCTTCGATTCTACTCCTTATCTTCGTAAAGTCTGGGTAGGCTTAATTGAAAGTTACTTGATTGA
GGCCAAATGGTACTATAAAGGCCATAAACCTAGTTTAGAAGAATACATGAAGAACAGTTGGATTAGTATCGG
CGGCATTCCAATCTTAAGTCACTTATTCTTCCGTTTGACTGACTCTATCGAGGAAGAAGCAGCAGAAAGTATGC
ACAAATATCACGATATTGTTCGTGCAAGCTGCACTATCTTGCGTCTTGCCGACGATATGGGGACTTCCCTTGAC
GAAGTGGAACGTGGAGATGTACCAAAGTCCGTCCAATGTTATATGAACGAGAAGAATGCCAGTGAAGAAGA
GGCTCGTGAACACGTGCGTAGCCTTATTGACCAAACGTGGAAGATGATGAACAAAGAAATGATGACGAGTTC
TTTCTCCAAATACTTCGTCGAAGTATCTGCTAACTTAGCACGTATGGCACAGTGGATCTACCAACATGAGAGTG
ATGGCTTTGGTATGCAACACTCCTTAGTGAACAAGATGCTGCGTGACTTATTATTTCATCGTTATGAA

>BR8-CS-SFRU (SEQ ID 20)

MRRTGGYQPTLWDFSTIQSFDSEYKEEKHLMRAAGMIDQVKMMLQEEVDSIRRLELIDDLRRLGISCHFE

REIVEILNSKYYTNNEIDERDLYSTALRFRLLRQYDFSVSQEVFDCFKNAKGTDFKPSLVDDTRGLLQLY

EASFLSAQGEETLRLARDFATKFLQKRVLVDKDINLLSSIERALELPTHWRVQMPNARSFIDAYKRRPDM

NPTVLELAKLDFNMVQAQFQQELKEASRWWNSTGLVHELPFVRDRIVECYYWTTGVVERRQHGYERIMLT

KINALVTTIDDVFDIYGTLEELQLFTTAIQRWDIESMKQLPPYMQICYLALFNFVNEMAYDTLRDKGFDS

TPYLRKVWVGLIESYLIEAKWYYKGHKPSLEEYMKNSWISIGGIPILSHLFFRLTDSIEEEAAESMHKYH

DIVRASCTILRLADDMGTSLDEVERGDVPKSVQCYMNEKNASEEEAREHVRSLIDQTWKMMNKEMMTSSF

SKYFVEVSANLARMAQWIYQHESDGFGMQHSLVNKMLRDLLFHRYE

Figure 16A

```
                      1                                                 50
BR1-TPS10      (1)    MRRSANYQPSRWDHHHLLSVENKPAKDKRVRERDLLKEKVRKMLNDEQ--
BR2-LS-MSPI    (1)    MRRSGNYNPSRWDVNFIQSLLSDY-KEDKHVIRASELVTLVKMELEKE--
BR3-SS-SOFF    (1)    MRRSGDYQPSLWDFNYIQSLNTPY-KEQRHFNRQAELIMQVRMLLKVK--
BR4-BPS-ROFF   (1)    MRRSGNYQPSSWDFNYIQSLNTPY-KEERQLNREAELIVQVKMLLKEK--
BR4-BPS-SOFF   (1)    MRRSGNYQPALWDSNYIQSLNTPY-TEERHLDRKAELIVQVRILLKEK--
BR5-CAMS-AGR   (1)    MRRVGNYHSNLWDDDFIQSLISTPYGAPDYRERADRLIGEVKDIMFNFKS
BR5-CAMS-PME   (1)    MRRVGNYHSNLWDDDFINSLISTPYEAPSYRERGETLIGEVKEI-FNSIS
BR6-PS-AANN    (1)    MRRSANYAPSLWSYDFVQSLSSKYKGDNYMARSRALKGVVRTMILEANG-
BR7-FS-OBAS    (1)    MRRSGNYQPSAWDFNYIQSLNNNHSKEERHLQGKAKLIEEVKMLLEQE--
BR8-CS-SFRU    (1)    MRRTGGYQPTLWDFSTIQSFDSEY-KEEKHLMRAAGMIDQVKMMLQEE--
Consensus      (1)    MRRSGNYQPSLWDFNFIQSL  S Y KEERHL R A LI  VKMLL 51                                                100
BR1-TPS10      (49)   -----------KTYLDQLEFIDDLQKLGVSYHFEAEIDNILTSSYK---K
BR2-LS-MSPI    (48)   -----------TDQIRQLELIDDLQRMGLSDHFQNEFKEILSSIYLDHHY
BR3-SS-SOFF    (48)   -----------MEAIQQLELIDDLQYLGLSYFFQDEIKQILSSIHNEPRY
BR4-BPS-ROFF   (48)   -----------REYVKQLELIDDLKYLGLSYFFQDEIKEILGFIYNEHKW
BR4-BPS-SOFF   (48)   -----------MEPVQQLELIHDLKYLGLSDFFQDEIKEILGVIYNEHKC
BR5-CAMS-AGR   (51)   LEDGG------NDLLQRLLLVDDVERLGIDRHFKKEIKTALDYVNSYWNE
BR5-CAMS-PME   (50)   VEDAGELITPLNDLIQRLWMVDSVERLGIDRHFKDEIKSALDYVYSHWRE
BR6-PS-AANN    (50)   ----------IENPLSLLNLVDDLQRLGISYHFLDEISNVLEKIYLNFYK
BR7-FS-OBAS    (49)   -----------MAAVQQLEFIEDLKNLGLSYLFQDEIKIILNSIYNHHKC
BR8-CS-SFRU    (48)   -----------VDSIRRLELIDDLRRLGISCHFEREIVEILNSKYYTNNE
Consensus      (51)              D IQQLELIDDL RLGLSYHFQDEIK IL SIY   K 101                                               150
BR1-TPS10      (85)   DRTNI-----QESDLHATALEFRLFRQHGFNVSEDVFDVFMENCGKFDRD
BR2-LS-MSPI    (87)   YKNPFPK---EERDLYSTSLAFRLLREHGFQVAQEVFDSFKNEEG-EFKE
BR3-SS-SOFF    (87)   FHNN--------DLYFTALGFRILRQHGFNVSEDVFDCFKIEKCSDFNA
BR4-BPS-ROFF   (87)   LDNSEA----DERDLYLKALGFRILRQHGFNVSQEVFDCFKNEKGSDFKA
BR4-BPS-SOFF   (87)   FHNNEV----EKMDLYFTALGFRLLRQHGFNISQDVFNCFKNEKGIDFKA
BR5-CAMS-AGR   (95)   KGIGCGRES-VVTDLNSTALGLRTLRLHGYTVSSDVLNVFKDKNGQFSST
BR5-CAMS-PME   (100)  EGIGCGRES-VATDLNSTALGLRTLRLHGYPVSSDVLEHFKDQKGHFASC
BR6-PS-AANN    (90)   SPEKW-----TNMDLNLRSLGFRLLRQHGYHIPQEIFKDFIDVNGNF-KG
BR7-FS-OBAS    (88)   FHNNHQQRTDENADLYFVALGFRLFRQHGFKVSQEVFDCFKNEEGSDFIP
BR8-CS-SFRU    (87)   I---------DERDLYSTALRFRLLRQYDFSVSQEVFDCFKNAKGTDFKP
Consensus      (101)             N   E   DLYSTALGFRLLRQHGFNVSQDVFDCFKNEKG DFK 151                                               200
BR1-TPS10      (130)  DIY---------GLISLYEASYLSTKLDKNLQIFIRPFATQQLRDFVDTH
BR2-LS-MSPI    (133)  SLSDDT-----RGLLQLYEASFLLTEGETTLES-AREFATKFLEEKVNE-
BR3-SS-SOFF    (128)  NLAQDT-----KGMLQLYEASFLLREGEDTLEL-ARRFSTRSLREKFDEG
BR4-BPS-ROFF   (133)  SLAQDT-----KGILQLYEAAFLLREGEDTLEL-ARAFATKCLQKKLDEG
BR4-BPS-SOFF   (133)  SLAQDT-----KGMLQLYEASFLLRKGEDTLEL-AREFATKCLQKKLDEG
BR5-CAMS-AGR   (144)  ANIQIE--GEIRGVLNLFRASLVAFPGEKVMDE-AETFSTKYLREALQ--
BR5-CAMS-PME   (149)  SSSSIETGGEIRSVLNLFRASLIAFPNEKVMDE-AQIFSTTYLKEAVQ--
BR6-PS-AANN    (134)  DII--------SMLNLYEASYHSVE-EESILDDAREFTTKYLKETLENI
BR7-FS-OBAS    (138)  NLAEDT-----KGLLQLYEASYLVRQDEDTLEM-ARQFSTKILQKKVEE-
BR8-CS-SFRU    (128)  SLVDDT-----RGLLQLYEASFLSAQGEETLRL-ARDFATKFLQKRVLV-
Consensus      (151)  SLA DT     KGLLQLYEASFLS   GEDTLEL AR FATKYLREKVDE 201                                               250
BR1-TPS10      (171)  SNEDFGSCDMVEIVVQALDMPYYWQMRRLSTRWYIDVYGKRQNYKNLV--
BR2-LS-MSPI    (176)  -GGV--DGDLLTRIAYSLDIPLHWRIKRPNAPVWIEWYRKRPDM-NPV--
BR3-SS-SOFF    (172)  GDEI--DEDLSSWIRHSLDLPLHWRVQGLEARWFLDAYARRPDM-NPL--
BR4-BPS-ROFF   (177)  GDGI--DENLLSWIRHSLDLPLHWRIQRLEARWFLDAYARRPDM-NPL--
BR4-BPS-SOFF   (177)  GNEI--DENLLLWIRHSLDLPLHWRIQSVEARWFIDAYARRPDM-NPL--
BR5-CAMS-AGR   (189)  --KIPASSILSLEIRDVLEYGWHTNLPRLEARNYMDVFGQH-TKNKNA--
BR5-CAMS-PME   (196)  --KIPVSS-LSRQIEYVMEYGWDTNLPRLEARHYIHVLGQDITYNDNEMP
BR6-PS-AANN    (174)  EDQ-----NIALFISHALVFPLHWMVPRVETSWFIEVYPKKVGM-NPT--
```

Figure 16B

```
BR7-FS-OBAS    (181) -KMI---EENLLSWTCHSLELPLHWRVQRIEAKWFLDAYASKPDM-NPI--
BR8-CS-SFRU    (171) -DK---DINLLSSIERALELPTHWRVQMPNARSFIDAYKRRPDM-NPT--
Consensus      (201)        I  D NLLSWI HSLDLPLHWRVQRLEARWFIDAYARRPDM  NPL
                     251                                                  300
BR1-TPS10      (219) ------VVEFAKIDFNIVQAIHQEELKNVSSWWMETGLGKQLYFARDRIV
BR2-LS-MSPI    (220) ------VLELAILDLNIVQAQFQEELKESFRWWRNTGFVEKLPFARDRLV
BR3-SS-SOFF    (217) ------IFKLAKLNFNIVQATYQEELKDISRWWNSSCLAEKLPFVRDRIV
BR4-BPS-ROFF   (222) ------IFELAKLDFNIIQATYQQELKDVSRWWNRLGLAEKLPFVRDRIV
BR4-BPS-SOFF   (222) ------IFELAKLNFNIIQATHQQELKDLSRWWSRLCFPEKLPFVRDRLV
BR5-CAMS-AGR   (234) ---AEKLLELAKLEFNIFHSLQERELKHVSRWWKDSGSPEMT-FCRHRHV
BR5-CAMS-PME   (243) YTNVEKLLELAKLEFNMFHSLQQRELKHLSRWWKDSGMPEAT-FTRHRHV
BR6-PS-AANN    (216) ------VLEFAKLDFNILQAVHQEDMKKASRWWKET-CWEKFGFARDRLV
BR7-FS-OBAS    (225) ------IFELAKLEFNIAQALQQGELKDLSRWWNDTGIAEKLPFARDRIV
BR8-CS-SFRU    (214) ------VLELAKLDFNMVQAQFQQELKEASRWWNSTGLVHELPFVRDRIV
Consensus      (251)       ILELAKLDFNIVQALHQ ELKDLSRWW DTGL EKLPF RDRIV
                     301                                                  350
BR1-TPS10      (263) ENYFWTIGQIQEPQYGYVRQTMTKINALLTTIDDDIYDIYGTLEELQLFTV
BR2-LS-MSPI    (264) ECYFWNTGIIEPRQHASARIMMGKVNALITVIDDDIYDVYGTLEELEQFTD
BR3-SS-SOFF    (261) ECFFWAIAAFEPHQYSYQRKMAAVIITFITIIDDVYDVYGTIEELELLTD
BR4-BPS-ROFF   (266) ESYFWGVGMFEPNQYGYQRKMSGIIIMLATVIDDVYDVYGTLDELQLFTD
BR4-BPS-SOFF   (266) ESFFWAVGMFEPHQHGYQRKMAATIIVLATVIDDIYDVYGTLDELELFTD
BR5-CAMS-AGR   (280) EYYALASCIAFEPQHSGFRLGFTKMSHLITVLDDMYDVFGTVDELELFTA
BR5-CAMS-PME   (292) EYYALASCIAFEPQHSGFRFGFAKLCHIITVLDDMYDLFGTIDELELFTA
BR6-PS-AANN    (259) ENFMWTVAENYLPHFQTGRGVLTKVNAMITTIDDVYDVYGTLPELELFTN
BR7-FS-OBAS    (269) EAHYWAIGTLEPYQYRYQRSLIAKIIALTTVVDDVYDVYGTLDEPQLFTD
BR8-CS-SFRU    (258) ECYYWTTGVVERRQHGYERIMLTKINALVTTIDDVFDIYGTLEELQLFTT
Consensus      (301) E YFWAIGI EP QHGY R MLAKI ALITVIDDVYDVYGTLDELELFTD
                     351                                                  400
BR1-TPS10      (313) AFEN--WDINRLDELPEYMRLCFLVIYNEVNSIACEILRTKNINVIPFLK
BR2-LS-MSPI    (314) LIRR--WDINSIDQLPDYMQLCFLALNNFVDDTSYDVMKEKGVNVIPYLR
BR3-SS-SOFF    (311) MIRR--WDNKSISRAYLPYYMQVCYLALYNFVSERAYDILKDQHFISIPYLQ
BR4-BPS-ROFF   (316) TIRSFSWDTESISQLPYYMQLCYLALYNFSELAYDNLKEQHFISIPYLH
BR4-BPS-SOFF   (316) TFKR--WDTESITRLPYYMQLCYWGVHNYISDAAYDILKEHGFFCLQYLR
BR5-CAMS-AGR   (330) TIKR--WDPSAMECLPEYMKGVYMMVYHTVNEMARVAEKAQGRDTLNYAR
BR5-CAMS-PME   (342) AIKR--WDPSATDCLPEYMKGVYTMVYDTINEMAGEAQNAQGRDTLNYAR
BR6-PS-AANN    (309) IVNS--WDINAIDELPDYLKICFLACYNATNELSYNTLTNKGFFVHPYLK
BR7-FS-OBAS    (319) AIRR--WDIESINQLPHYLQLCYLAIYNFVSELAYDIFRDKGFNSLPYLH
BR8-CS-SFRU    (308) AIQR--WDIESMKQLPPYMQICYLALFNFVNEMAYDTLRDKGFDSTPYLR
Consensus      (351)     IRR  WDI SIDQLPEYMQLCYLALYNFVNELAYDILKDKGF SIPYLR
                     401                                                  450
BR1-TPS10      (361) KSWTDVSKAYLVEAKWYKSGHKPNLEEYMQNARISISSSPTIFVHFYCVFS
BR2-LS-MSPI    (362) QSWVDLADKYMVEARWFYGGHKPSLEEYLENSWQSISGPCMLTHIFFRVT
BR3-SS-SOFF    (359) RSWVSLVEGYLKEAYWYYNGYKPSLEEYLNNAKISISAPTIISQLYFTLA
BR4-BPS-ROFF   (366) KSWVDLAEAYLKEAKWYYSGYTPSLEEYLSNAKISIASPNIISQLHFTLA
BR4-BPS-SOFF   (364) KSVVDLVEAYFHEAKWYHSGYTPSLDEYLNIAKISVASPAIISPTYFTFA
BR5-CAMS-AGR   (378) QAWEACFDSYMQEAKWIATGYLPTFEEYLENGKVSSAHRPCALQPILTLD
BR5-CAMS-PME   (390) EAWEACLDSYLQEAKWIATGYLPSFEEYYENGKVSSAHRVCTLQPILTLD
BR6-PS-AANN    (357) KAWQDLCNSYIIEAKWFNDGYTPTFNEFIENAYMSIGIAPIIRHAYLLTL
BR7-FS-OBAS    (367) KSWLDLVEAYFLEAKWFHSGYTPTLEEYLNNSKMTITCPAIVSEIYFAFA
BR8-CS-SFRU    (356) KVWVGLIESYLIEAKWYYKGHKPSLEEYMKNSWISIGGIPILSHLFFRLT
Consensus      (401) KSWVDLVEAYLIEAKWYYSGY PSLEEYL NAKISIA P IIS LYFTLA
                     451                                                  500
BR1-TPS10      (411) DQLSIQVLETLSQHQQNVVRCSSSVFRLANDLVTSPDELARGDVCKSIQC
BR2-LS-MSPI    (412) D-SFTKETVDSLYKYHDLVRWSSFVLRLADDLGTSVEEVSRGDVPKSLQC
BR3-SS-SOFF    (409) N-SIDETAIESLYQYHNILYLSGTILRLADDLGTSQHELERGDVPKAIQC
BR4-BPS-ROFF   (416) NSSTDKWSIESLYQYHNILNLSGMLLRLADDVGTAPFELKRGDVQKAIQC
BR4-BPS-SOFF   (414) NASHDTAVIDSLYQYHDILCLAGIILRLPDDLGTSYFELARGDVPKTIQC
```

Figure 16C

```
BR5-CAMS-AGR  (428) IPFPDHILKEVDFPSK-LNDLICIILRLRGDTRCYKADRARGEEASSISC
BR5-CAMS-PME  (440) IPFPDHILKEVDFPSK-LNDLACAVLRLRGDTRCYQADRARGEEASSISC
BR6-PS-AANN   (407) TSVTEEALQHI-ERAESMIRNACLIVRLTNDMGTSSDELERGDIPKSIQC
BR7-FS-OBAS   (417) N-SIDKTEVESVYKYHDILYLSGMLLRLPDDLGTTTFEMKRGDVAKAIQC
BR8-CS-SFRU   (406) D-SIEEEAAESMHKYHDIVRASCTILRLADDMGTSLDEVERGDVPKSVQC
   Consensus  (451)   S D   LIESLY YH IL LS IILRLADDLGTS  ELARGDVPKSIQC
                     501                                              550
BR1-TPS10     (461) YMSET-GASEDKARSHVRQMINDLWDEMNYEKMAHSSSILHHDFMETVIN
BR2-LS-MSPI   (461) YMSDY-NASEAEARKHVKWLIAEVWKKMNAERVSKDSPF-GKDFIGCAVD
BR3-SS-SOFF   (458) YMNDT-NASEREAVEHVKFLIREAWKEMNTVTTASDCPF-TDDLVAAAAN
BR4-BPS-ROFF  (466) HMKDR-NASEKEAQEHVMFLLREAWKEMNTAM-ADGYPF-ADELVAAAAN
BR4-BPS-SOFF  (464) YMKET-NASEEEAVEHVKFLIREAWKDMNTAI-AAGYPF-PDGMVAGAAN
BR5-CAMS-AGR  (477) YMKDNPGLTEEDALNHINFMIRDAIRELNWELLKPDNSVPITS-KKHAFD
BR5-CAMS-PME  (489) YMKDNPGSTEEDALNHINAMLSDVIKELNWELLKPD-SVPISA-KKHAYD
BR6-PS-AANN   (456) YMHES-GATEMEARAYIKQFIVETWKKLNKERQEIGSEF-PQEFVDCVIN
BR7-FS-OBAS   (466) YMKEH-NASEEEAREHIRFLMREAWKQMNTAAAANNCPF-VNDFVVGAAS
BR8-CS-SFRU   (455) YMNEK-NASEEEAREHVRSLIDQTWKMMNKEMMT--SSF-SKYFVEVSAN
   Consensus  (501) YMKD  NASEEEAREHVKFLIREAWKEMN ELLA   PF  DFV  AAN
                     551                              589
BR1-TPS10     (510) LARMSQCMY-QYGDGHGSPEKAKIVDRVMSLLFNPIPLD
BR2-LS-MSPI   (509) LGRMAQLMY-HNGDGHGTQHPIIH-QQMTRTLFEPFA--
BR3-SS-SOFF   (506) LARAAQFIY-LDGDGHGVQHSEIH-QQMGGLLFQPYV--
BR4-BPS-ROFF  (513) LGRVAQFMY-LEGDGHGVQHSGIH-QQMAGLLFEPYT--
BR4-BPS-SOFF  (511) IGRVAQFIY-LHGDGFGVQHSKTY-EHIAGLLFEPYA--
BR5-CAMS-AGR  (526) ISRVWHHGY-RYRDGYSFANVETK-SLVMRTVIEPVPL-
BR5-CAMS-PME  (537) VSRAFHYGY-KYRDGYSVANIEIK-NFVAISVLEPV---
BR6-PS-AANN   (504) LPRMGHFMY-TDGDKHGKPDMFK--PYVFSLFVNPI---
BR7-FS-OBAS   (514) LGRVANFVY-VEGDGFGVQHSKIH-QQMAELLFYPYQ--
BR8-CS-SFRU   (501) LARMAQWIYQHESDGFGMQHSLVN-KMLRDLLFHRYE--
   Consensus  (551) LGRMAQFMY  EGDGHGVQHS IH Q MA LLFEPY
```

PRODUCTION OF MONOTERPENES

CROSS-REFERENCES TO RELATED APPLICATIONS

This application claims the benefit of U.S. Provisional Application No. 61/319,560 filed Mar. 31, 2010 and U.S. Provisional Application No. 61/319,586 filed Mar. 31, 2010, the entire contents of which are incorporated herein by reference.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 90834-848430_ST25.TXT, created on Nov. 18, 2012, 88,816 bytes, machine format IBM-PC, MS-Windows operating system, is hereby incorporated by reference in its entirety for all purposes.

FIELD OF THE INVENTION

The present invention relates to methods for the engineered biosynthesis of cyclic monoterpenes, compositions comprising the bioengineered cyclic monoterpenes and methods of use of said compounds.

BACKGROUND OF THE INVENTION

Terpenes are hydrocarbons that are commonly found in plants and seeds. Certain naturally occurring terpenes, such as the cyclic monoterpenes, may be used in, e.g., fuel compositions and solvents for art restoration. These monoterpenes include the monocyclic monoterpenes such as limonene and terpinolene and the bicyclic monoterpenes such as α-pinene, β-pinene, bornyl diphosphate, sabinene and camphene. It has been recently discovered that the tricyclic monoterpene, tricyclene which is distinct from the monocyclic and bicyclic monoterpenes delineated above has very good octane properties and oxidative stability and therefore may be better suited for use as a gasoline component than other monoterpenes. Tricyclene may be obtained from natural sources. It can, for example, be extracted from a plant source, such as *Cordia cylindrostachya* and *Salvia fruiticosa*. It may also be made synthetically, for example by the isomerization of α-pinene into tricyclene and camphene (C M Lopez et al., (2001) *React Kinet Catal Lett* 74:163-170).

In biological systems, terpenes are synthesized from products and intermediates of carbohydrate metabolism by numerous enzyme-catalyzed reactions in the mevalonate (MEV) pathway or 1-deoxy-D-xylulose-5-phosphate (DXP) pathway and are assembled with five-carbon building blocks called isoprene units through the conversion of isopentenyl pyrophosphate (IPP) and dimethylallylpyrophosphate (DMAPP). See FIG. 1 and P. Dewitt (2002) *Nat. Prod. Rep.*, 19:181-222. A transferase is used to elongate the isoprene units to obtain the corresponding monoterpene precursor geranyl pyrophosphate (GPP). Terpene synthases (also sometimes referred to as terpene cyclases) catalyze formation of the monoterpene products by a series of carbocation intermediates that can undergo a variety of cyclizations.

Reports describe microbial strains that have been engineered to produce terpenes (V J J Martin et al., (2003) *Nature Biotechnol* 21:796-802 and Takahashi et al., (2007) *Biotechnol. Bioeng.* 97:170-181); however, the inventors are not aware of any reports of a strain that has been engineered to produce tricyclene. Mutants of a pinene synthase were reported to produce trace amounts of tricyclene in vitro from GPP (Hyatt and Croteau (2005) *Arch. Biochem. Biophys.* 439: 222-223). Likewise, a terpene synthase from *Arabidopsis thaliana* was reported to generate a small amount of tricyclene in vitro (J. Bohlmann et al., (2002) *Arch. Biochem. Biophys.* 375:261-269). However, when the inventors of the present invention expressed either of these pinene synthases or the *A. thaliana* terpene synthase in *E. coli*, together with the mevalonate pathway to supply GPP in vivo they found tricyclene was not produced.

BRIEF SUMMARY OF THE INVENTION

In one aspect, the method for producing a monoterpene, e.g., tricyclene, comprises culturing a microbial organism expressing a heterologous terpene synthase under conditions in which the terpene synthase converts geranyl diphosphate to a monoterpene, e.g., tricyclene. In some aspects, tricyclene is produced at a level of at least 0.5% or at least 5% of total monoterpene production by the organism.

In some aspects, the terpene synthase is a bornyl diphosphate synthase or a variant thereof. In one aspect, the terpene synthase has at least 80% or at least 90% sequence identity to SEQ ID NO: 2 or 4. In one aspect, the terpene synthase comprises at least 90% sequence identity to SEQ ID NO: 2, and comprises an amino acid substitution at one or both of positions V399 and I404 of SEQ ID NO: 2. The substitution at position V399 can be V399I. In one aspect, the terpene synthase further comprises an amino acid substitution at one or more of positions S4, E159, G338, S267, I291, I297, K285, T460, and F525 of SEQ ID NO: 2.

In some aspects, the terpene synthase is a camphene synthase or a variant thereof. In one aspect, the terpene synthase has at least 80% or at least 90% sequence identity to SEQ ID NO: 6 or 8. In one aspect, the terpene synthase comprises at least 90% sequence identity with SEQ ID NO: 6, and comprises an amino acid substitution at one or more of positions N18, A283, I320, and T431 of SEQ ID NO: 6. In one aspect, the terpene synthase further comprises an amino acid substitution at one or more of positions V537, V429, W392, A376, C353, G156, K142, K491, L385, M259, P219, P434, and V537 of SEQ ID NO: 6.

In one aspect, the terpene synthase is a wild-type heterologous terpene synthase.

In another aspect, the terpene synthase is a variant synthase, e.g., a bornyl diphosphate synthase variant or a camphene synthase variant. In another aspect, the terpene synthase has an amino acid modification at one or more positions corresponding to positions 270, 294, 366, 373, 404, 414, 460, and 525 of SEQ ID NO: 2.

In one aspect, the variant terpene synthase produces more tricyclene than the bornyl diphosphate synthase or camphene synthase from which it was derived.

In one aspect, the microbial organism also expresses a prenyl transferase, and the method further comprises contacting the prenyl transferase with IPP and DMAPP to yield geranyl pyrophosphate. The prenyl transferase can be heterologous.

In one aspect, the microbial organism is a bacterial cell or a yeast cell.

In one aspect, the microbial organism is cultured under fermentation conditions in a fermentation medium (e.g., a medium comprising fermentable sugar such as glucose). In one aspect, the microbial cells produce at least 0.1 mg/L tricyclene of fermentation medium. In one aspect, the method further comprising converting a cellulosic feedstock to a fermentable sugar. In one aspect, the culture conditions comprise a two-phase fermentation.

In one aspect, the method further comprising recovering a monoterpene, e.g., tricyclene.

In another aspect, the tricyclene is incorporated into a chemical mixture, e.g., a fuel composition. The fuel composition can further comprise, e.g., ethanol and/or fuel additive(s).

In another aspect, a codon-optimized nucleic acid is provided that encodes a terpene synthase that produces tricyclene in a recombinant microorganism.

In another aspect, a vector comprises a nucleic acid encoding a variant terpene synthase as described herein. In some aspects, the variant terpene synthase produces an amount of tricyclene that is 2-fold more than the corresponding wild-type terpene synthase. In some aspects, the nucleic acid comprises at least 80% sequence identity to SEQ ID NO: 1, 3, 5, or 7. In another aspect, the invention provides a host cell comprising the vector.

In one aspect, an isolated terpene synthase variant is provided, wherein the synthase has an amino acid sequence comprising the sequence of a variant listed in Table 4, 5, or 6.

In one aspect, an isolated variant terpene synthase has at least 90% sequence identity with SEQ ID NO: 2, and has an amino acid substitution at position V399 and/or I404 of SEQ ID NO: 2. In one aspect, the variant terpene synthase further comprises an amino acid substitution at one or more of positions S4, E159, G338, S267, I291, I297, K285, T460, and/or F525 of SEQ ID NO: 2.

In another aspect, an isolated terpene synthase variant has at least 90% sequence identity with SEQ ID NO: 6, and has an amino acid substitution at one or more of positions N18, A283, I320, and T431 of SEQ ID NO: 6. In one aspect, the variant terpene synthase further comprises an amino acid substitution at one or more of positions V537, V429, W392, A376, C353, G156, K142, K491, L385, M259, P219, P434, and V537 of SEQ ID NO: 6.

In another aspect, the invention provides a polynucleotide encoding one of the variant terpene synthases as described above.

BRIEF DESCRIPTION OF THE DRAWINGS

FIG. 3 depicts the codon optimized nucleotide sequence (SEQ ID NO: 1) and amino acid sequence (SEQ ID NO: 2) of a bornyl diphosphate synthase obtained from *Salvia officinalis* (BPS-SOFF).

FIG. 4 depicts the codon optimized nucleotide sequence (SEQ ID NO: 3) and the amino acid sequence (SEQ ID NO: 4) of a bornyl diphosphate synthase obtained from *Rosemarinus officinalis* (BPS-ROFF).

FIG. 5 depicts the codon optimized nucleotide sequence (SEQ ID NO: 5) and the amino acid sequence (SEQ ID NO: 6) of a camphene synthase obtained from *Pseudotsuga menzeseii* (CamS-PMEN).

FIG. 9 depicts the codon optimized nucleotide sequence (SEQ ID NO: 7) and the amino acid sequence (SEQ ID NO: 8) of a camphene synthase obtained from *Abies grandis* (CamS-AGR).

FIG. 10 depicts the codon optimized nucleotide sequence (SEQ ID NO: 9) and the amino acid sequence (SEQ ID NO: 10) of TPS10 synthase obtained from *Arabidopsis thaliana* (TPS10).

FIG. 11 depicts the codon optimized nucleotide sequence (SEQ ID NO: 11) and the amino acid sequence (SEQ ID NO: 12) of a limonene synthase obtained from *Mentha spicata* (LS-MSPI).

FIG. 12 depicts the codon optimized nucleotide sequence (SEQ ID NO: 13) and the amino acid sequence (SEQ ID NO: 14) of a sabinene synthase obtained from *Salvia officinalis* (SS-SOFF).

FIG. 13 depicts the codon optimized nucleotide sequence (SEQ ID NO: 15) and the amino acid sequence (SEQ ID NO: 16) of a pinene synthase obtained from *Artemisia annua* (PS-AANN).

FIG. 14 depicts the codon optimized nucleotide sequence (SEQ ID NO: 17) and the amino acid sequence (SEQ 10 NO: 18) of a fenchol synthase obtained from *Ocimum basilicum* (FS-OBAS).

FIG. 15 depicts the codon optimized nucleotide sequence (SEQ ID NO: 19) and the amino acid sequence (SEQ ID NO: 20) of a cineole synthase obtained from *Salvia fruticosa* (CS-SFRU).

FIGS. 16A-C depicts the sequence alignment for the 10 exemplary terpene synthases (SEQ ID NOS:10, 12, 14, 4, 2, 8, 6, 16, 18 and 20, respectively) and their corresponding consensus sequence (SEQ ID NO:23). This alignment was be obtained using AlignX® (AlignX Jul. 31, 2006, a component of Vector NTI advance 10.3.0 and is based on the ClustalW algorithm). The following default AlignX multiple alignment parameters were used for multiple sequence alignment of terpene synthases—DNA/Protein Gap Open Penalty: 15/10; DNA/Protein Gap Extension Penalty: 6.66/0.05; Gap separation penalty range: 8; Use end gap separation penalty; % identity for alignment delay: 40; Use residue-specific gaps; Use hydrophilic residue gap; transition weighing (for DNA only). After the multiple sequence alignment, the percentage of identical residues among all ungapped positions between the pairs was calculated, and performance sensitive positions (PSPs) were identified.

DETAILED DESCRIPTION OF THE INVENTION

I. Introduction

This invention provides terpene synthases and variants thereof useful for producing monoterpenes, e.g., tricyclene. In some embodiments the terpene synthases catalyze the conversion of geranyl pyrophosphate (GPP) to tricyclene in vivo. In one aspect the present disclosure provides methods for bioengineering microbial cells to produce tricyclene by introducing heterologous monoterpene synthases such as bornyl diphosphate synthase (BPS) or camphene synthase into said microbial cell. The invention also provides recombinant microbial cells that have a heterologous polynucleotide that encodes a terpene synthase. These recombinant microbial cells may be used in the commercial production of monoterpenes.

II. Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references (see generally, Sambrook et al. Molecular Cloning: A Laboratory Manual, 2d ed. (1989) Cold Spring Harbor Laboratory Press, Cold Spring Harbor, N.Y., which is incorporated herein by reference), which are provided throughout this document.

"Isoprene" is 2-methyl-1,3-butadiene ($C_5H_8$) and is the monomer building block for terpenes, defined below. As used herein, "isoprene" refers to the isoprene monomer per se, as well as the functional isoprene isomers dimethylallyl pyrophosphate (DMAPP) and isopentenyl pyrophosphate (IPP), which are utilized in biological systems. The terms "pyrophosphate" and "diphosphate" are used herein interchangeably.

Figure 1:
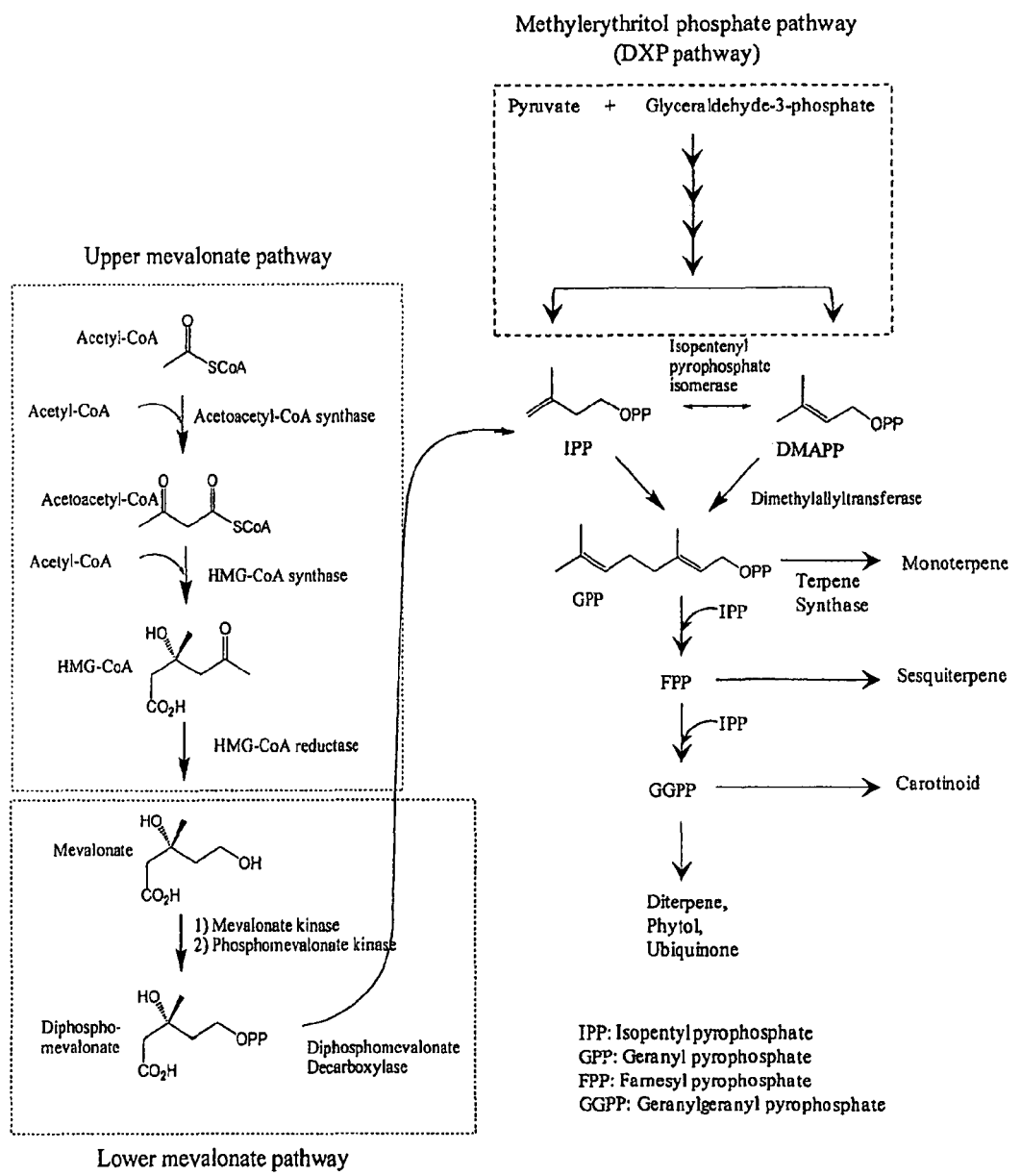
FIG. 1 generally illustrates isoprenoid biosynthesis. IPP and DMAPP, which are substrates for the production of prenyl pyrophosphates such as geranyl pyrophosphate (GPP), farnesyl pyrophosphate (FPP) and geranyl geranyl pyrophosphate (GGPP), may be generated by the MEV pathway or the DXP pathway. GPP may be further modified by terpene synthases to generate monoterpenes (C10).

The isomers DMAPP and/or IPP can be condensed to form geranyl pyrophosphate (GPP) as shown in FIG. 1 (or to form further condensation products such as the 15-carbon farnesyl diphosphate (FPP)). This condensation reaction is catalyzed by a "prenyl transferase" (e.g., dimethylallyl transferase, FPP synthase, or GPP synthase).

The term "terpene synthase" refers to any enzyme that catalyzes the conversion of GPP to a terpene. The substrate for the terpene synthase (the "terpene synthase substrate") is GPP. The term "terpene synthase" includes both linear and cyclic terpene synthases. Cyclic terpene synthases are also referred to as terpene cyclases.

The term "terpene" refers to any compound made up of two or more isoprene (C5) units. The term "terpene" includes compounds comprising only unmodified isoprene units, as well as compounds comprising one or more modified isoprene units (such as oxidation or rearrangement of the carbon skeleton). Such modified terpene compounds can also be referred to as "terpenoids" or "isoprenoids", which are used interchangeably herein. The number of C-atoms present in the terpene is typically evenly divisible by five (e.g., C5, C10, C15, C20, C25, C30 and C40). Irregular terpenes have been reported, and are also included in the definition of "terpene". Terpenes include, but are not limited to, monoterpenes (C10), sesquiterpenes (C15), diterpenes (C20), sesterterpenes (C25), triterpenes (C30), tetraterpenes (C40), and polyterpenes having long changes of many isoprene units. A terpene may be linear or cyclic.

The term "monoterpene" refers to a compound made up of two isoprene units. The term "monoterpene" includes compounds comprising only unmodified isoprene units, as well as compounds comprising one or more modifications as described above. When the monoterpene includes such a modification, it can also be referred to as a "monoterpenoid." A monoterpene may be linear or cyclic. Linear monoterpene include for example, geraniol and myrcene. Cyclic monoterpenes include for example, six-membered rings such as limonene and bicyclic rings such as pinene. Other non-limiting cyclic monoterpenes include for example: terpineol, tricyclene, thujene, borneol, sabinene, and camphene.

Tricyclene (CAS No. 508-32-7), also known as 1,1,7-trimethyl-tricyclo(2.2.1.0(2,6)) heptane, has the three ring structure of formula (I) shown below:

(I)

The term "biosynthetic pathway" is used to refer to the series of enzymes and steps in a pathway leading to the biosynthesis of a molecule.

The term "mevalonate pathway" or "MEV pathway" is used herein to refer to the biosynthetic pathway that converts acetyl-CoA to IPP and DMAPP. Similarly, a "mevalonate pathway enzyme" is an enzyme, or functional fragment or variant thereof, that catalyzes one or more steps in the MEV pathway (upper or lower MEV pathway).

The term "1-deoxy-D-xylulose 5-diphosphate (DXP) pathway" or "DXP pathway" is used herein to refer to the pathway that converts glyceraldehyde-3-phosphate and pyruvate to IPP and DMAPP through the pathway intermediate DXP. Similarly, a "DXP pathway enzyme" is an enzyme, or functional fragment or variant thereof, that catalyzes one or more steps in the DXP pathway.

The term "contacting", in the context of an enzyme and a substrate, refers to combining an enzyme and a substrate under conditions in which the enzyme can act on the substrate. Those skilled in the art will recognize that mixing a solution containing an enzyme (e.g., a terpene synthase) with a substrate (e.g., GPP) will effect "contacting."

The terms "naturally occurring", "native", and "wild-type" are used interchangeably herein to refer to a form found in nature. For example, when used in reference to a nucleotide or polypeptide sequence, the term means the nucleotide or polypeptide sequence occurring in a naturally occurring microorganism found in nature. When used in reference to a microorganism, the term means a naturally occurring (not genetically modified) microorganism.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Identity" or "percent identity" refers to two or more nucleotide or polypeptide sequences or sub-sequences that are the same or have a specified percentage of nucleotides or amino acid residues that are the same. For example, the sequence can have a percent identity of at least 50%, 60%, 70%, 85%, 90%, 91%, 92%, 93%, 94%, 95%, 96%, 97%, 98%, or 99% over a specified region to a reference sequence when compared and aligned for maximum correspondence over a comparison window, or designated region as measured using a sequence comparison algorithm or by manual alignment and visual inspection. Sequences that are at least about 88%, 89%, 90%, 91%, 92%, 93%, 94%, 95%, 96%, 97%, 98%, 99% identical can be called "substantially identical" or having "substantial sequence identity."

Two polynucleotide or amino acid sequences may be aligned manually (i.e., by inspection). Manual alignment is particularly convenient for aligning pairs of similar (e.g., 70% or more sequence identity) polypeptide sequences. While optimal alignment and scoring can be accomplished manually, the process is facilitated by the use of a computer-implemented alignment algorithm. To determine sequence identity, sequences can be aligned using the methods and computer programs, including BLAST, available over the world wide web (see, e.g., Altschul et al., 1990, *J. Mol. Biol.* 215:403-10) and, e.g., gapped BLAST 2.0 (see Altschul, et al. 1997, *Nucleic Acids Res.,* 25:3389-3402) made available to the public at the National Center for Biotechnology Information Website. Software for performing BLAST analyses is publicly available through the National Center for Biotechnology Information (on the worldwide web at ncbi.nlm.nih.gov/). The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For amino acid sequences, a scoring matrix is used to calculate the cumulative score. For amino acid sequences, the BLASTP program uses as defaults a word size (W) of 3, an expectation (E) of 10, and the BLOSUM62 scoring matrix (see Henikoff & Henikoff, 1989, *Proc. Natl. Acad. Sci. USA* 89:10915, incorporated herein by reference). Two sequences may be optimally aligned when they are aligned for similarity scoring using a defined amino acid substitution matrix (e.g., BLOSUM62), gap existence penalty and gap extension penalty so as to arrive at the highest score possible for that pair of sequences. The alignment is defined by the amino acid position of each sequence at which the alignment begins and ends, and optionally by the insertion of a gap or multiple gaps in one or both sequences so as to arrive at the highest possible score. Amino acid substitution matrices and their use in quantifying the similarity between two sequences are well-known in the art. The gap existence penalty is imposed for the introduction of a single amino acid gap in one of the aligned sequences, and the gap extension penalty is imposed for each additional empty amino acid position inserted into an already opened gap. Another alignment algorithms include FASTA, available in the Genetics Computing Group (GCG) package, from Madison, Wis., USA; and methods described in *Meth. Mol. Biol.* 70: 173-187 (1997) (Smith-Waterman) and *J. Mol. Biol.* 48: 443-453 (1970) (Needleman and Wunsch).

Optimal multiple (or pairwise) alignments also can be prepared using readily available programs such as PSI-BLAST, which is described by Altschul, et al. (1997), supra; AlignX® (AlignX Jul. 31, 2006, a component of Vector NTI advance 10.3.0 and is based on the ClustalW algorithm); or "T-Coffee" (Notredame et al., 2000, *J. Mol. Bio.* 302:205-17). T-Coffee alignments may be carried out using default parameters (T-Coffee Technical Documentation, Version 8.01, July 2009, WorldWideWeb.tcoffee.org).

A "reference sequence" refers to a defined sequence used as a basis for a sequence comparison.

The term "biologically active" used in reference to a polypeptide means that the polypeptide exhibits catalytic activity upon the substrate(s) identified.

The term "isolated" means in an environment different from naturally occurring environment. For example, an "isolated" polynucleotide, polypeptide, enzyme, compound, or cell can be one that is removed from the environment in which it naturally occurs. Also, an "isolated" recombinant cell can be a recombinant cell that has been isolated from the parent host cell and may be present in a clonal culture of cells or in a mixed population of cells, including other recombinant cells.

The term "endogenous", in the context of a species of microbe or other organism, refers to a naturally occurring gene or protein that is originally contained in the species. Conversely, an "exogenous" gene is one that originates outside the microorganism, such as a gene from another species, or a modified or recombinant gene. An exogenous gene may be introduced into the microorganism by methods known in the art.

The term "heterologous" is used to refer to a nucleic acid or polypeptide sequence from another species, i.e., a species different from the host cell species.

"Recombinant," when used in reference to e.g., a cell, nucleic acid or a polypeptide, refers to a material, or a material corresponding to the natural or native form of the material, that has been modified in a manner that would not otherwise exist in nature, or is identical thereto but produced or derived from synthetic materials and/or by manipulations using recombinant techniques. Non-limiting examples include among others, recombinant cells expressing a gene or genes that are not found with the native or naturally occurring (non-recombinant) form of the cell, or express native or naturally occurring genes that are otherwise expressed at a different level.

Thus, e.g., the term "recombinant" polynucleotide refers to one which is not naturally occurring, e.g., is made by the artificial combination of at least two otherwise separated segments of sequence through human intervention. This artificial combination is often accomplished by either chemical synthesis means, or by the artificial manipulation of isolated segments of nucleic acids, e.g., by genetic engineering techniques. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

"Vector" refers to a DNA construct comprising a DNA protein coding sequence. A vector may be an expression vector comprising a protein coding sequence operably linked to a suitable control sequence (i.e., promoter) capable of effecting the expression of the DNA in a suitable host.

As used herein, the term "operon" is used to refer to two or more contiguous coding regions (nucleotide sequences that encode a gene product such as an RNA or a protein) that are coordinately regulated by one or more controlling elements (e.g., a promoter). "Operably linked" means that DNA sequence segments are arranged so that they function in concert for their intended purposes, e.g., a promoter controls transcription of a gene sequence to which it is operably linked.

As used herein, the term "gene product" refers to RNA encoded by DNA (or vice versa) or protein that is encoded by an RNA or DNA.

"Coding sequence" refers to that portion of a nucleic acid that encodes an amino acid sequence of a protein. A gene will typically comprise one or more nucleotide sequences that encode a protein, and may also include introns and other non-coding nucleotide sequences.

The term "expression" includes any step involved in the production of a polypeptide including, but not limited to, transcription, post-transcriptional modification, translation, post-translational modification, and secretion.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (i.e., DNA exogenous to the cell).

A "host cell," "transformed cell," or "recombinant cell" denotes a eukaryotic cell or a prokaryotic cell wherein the cell has been used as a recipient for a nucleic acid, and includes the progeny of the transformed cell or recombinant cell that has been genetically modified by the nucleic acid.

The term "variant" means a nucleic acid or polypeptide sequence that varies from the wild-type sequence. A variant can include substitutions (such as one or more conservative and/or non-conservative substitutions) additions, and/or deletions. Variants can be produced by methods including, but not limited to site-specific mutagenesis and sequence shuffling.

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength.

"Improved production" refers to an increase in the amount of measureable monoterpenes generally, or a specific monoterpene, e.g., tricyclene, produced by the recombinant microbial organism compared to the wild type microbial organism, when cultured under the same conditions. Production may be improved by any means including expressing an exogenous gene, increasing the expression of an endogenous gene, expressing a modified endogenous gene, and/or expressing modified exogenous gene.

"Bioengineered fuel" or "biofuel" refers to a fuel containing a component made by a recombinant host cell expressing a terpene synthase. For example, "bioengineered tricyclene" refers to tricyclene made by a recombinant host cell.

"Fuel composition" is a composition that comprises at least two fuel components.

"Fuel component" is any compound used to formulate a fuel composition.

"Fuel" refers to one or more hydrocarbons (e.g., alkanes, cycloalkanes and aromatic hydrocarbons), optionally in combination with one or more alcohols and/or one or more fatty esters. Fuel can be used to power internal combustion engines. In some embodiments, fuel comprises one or more of the isoprenoid compounds disclosed herein (e.g., monoterpenes).

"Fuel additive" refers to chemical components added to fuels to alter the properties of the fuel, e.g., to improve engine performance, fuel handling, fuel stability, or for contaminant control. Types of additives include, but are not limited to, antioxidants, thermal stability improvers, cetane improvers, stabilizers, cold flow improvers, combustion improvers, anti-foams, anti-haze additives, corrosion inhibitors, lubricity improvers, icing inhibitors, injector cleanliness additives, smoke suppressants, drag reducing additives, metal deactivators, dispersants, detergents, demulsifiers, dyes, markers, static dissipaters, biocides and combinations thereof.

As used herein, a composition that is a "substantially pure" compound is substantially free of one or more other compounds, i.e., the composition contains greater than 80 vol. % of the compound. Preferably the composition contains greater than 90 vol. %, greater than 95 vol. %, greater than 96 vol. %, greater than 97 vol. %, greater than 98 vol. %, greater than 99 vol. %, greater than 99.5 vol. %, greater than 99.6 vol. %, greater than 99.7 vol. %, greater than 99.8 vol. %, or greater than 99.9 vol. % of the compound; or less than 20 vol. %, of the one or more other compounds. Preferably, the composition contains less than 10 vol. %, less than 5 vol. %, less than 3 vol. %, less than 1 vol. %, less than 0.5 vol. %, less than 0.1 vol. %, or less than 0.01 vol. % of the one or more other compounds, based on the total volume of the composition.

As used herein and unless otherwise indicated, a composition that is "substantially free" of a compound means that the composition contains less than 20 vol. % of the compound. Preferably the composition contains less than 10 vol. %, less than 5 vol. %, less than 4 vol. %, less than 3 vol. %, less than 2 vol. %, less than 1 vol. %, less than 0.5 vol. %, less than 0.1 vol. %, or less than 0.01 vol. % of the compound, based on the total volume of the composition.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein "a", "an", and "the" include plural references unless the context clearly dictates otherwise.

The term "comprising" and its cognates are used in their inclusive sense; that is, equivalent to the term "including" and its corresponding cognates.

III. Terpene Production Via the MEV and DXP Pathways

Tricyclene and other terpenes may be synthesized from a five carbon precursor, isopentenyl pyrophosphate (IPP). As shown in FIG. 1, there are two major metabolic pathways for producing IPP:

1) the "mevalonate (MEV) pathway," which converts acetyl-CoA to IPP; and 2) the "1-deoxy-D-xylulose 5-diphosphate pathway" (also referred to as the "DXP pathway"), which converts D-glyceraldehyde-3-phosphate and pyruvate to IPP and DMAPP.

MEV pathway enzymes are depicted in FIG. 1. The MEV pathway comprises the following enzymatic reactions: (a) condensing two molecules of acetyl-CoA to acetoacetyl-CoA; (b) condensing acetoacetyl-CoA with acetyl-CoA to form hydroxymethylglutaryl (HMG)-CoA; (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to IPP. Enzymes that carry out these reactions include acetoacetyl-CoA thiolase, hydroxymethylglutaryl-CoA synthase (HMGS), hydroxymethylglutaryl-CoA reductase (HMGR), mevalonate kinase (MK), phosphomevalonate kinase (PMK), and mevalonate pyrophosphate decarboxylase (MPD). The upper MEV pathway includes enzymes responsible for the conversion of acetyl-CoA to mevalonate. The lower MEV pathway includes enzymes responsible for the conversion of mevalonate to isopentenyl diphosphate, which can be converted to its isomer, diphosphomevalonate (DMAPP), by isopentenyl pyrophosphate isomerase.

The IPP and/or the DMAPP can be acted on by prenyl transferases to produce polyprenyl pyrophosphates. IPP or DMAPP can be modified by prenyl transferases to generate the polyprenyl diphosphates geranyl diphosphate (GPP), farnesyl diphosphate (FPP), and geranylgeranyl diphosphate (GGPP).

In the DXP pathway, pyruvate and D-glyceraldehyde-3-phosphate are converted via a series of reactions to IPP and DMAPP. The pathway involves action of the following enzymes: 1-deoxy-D-xylulose-5-phosphate synthase (Dxs), l-deoxy-D-xylulose-5-phosphate reductoisomerase (IspC), 4-diphosphocytidyl-2-C-methyl-D-ervthritol synthase (IspD), 4-diphosphocytidyl-2-C-methyl-D-erythritol kinase (IspE), 2C-methyl-D-erythritol 2,4-cyclodiphosphate synthase (IspF), 1-hydroxy-2-methyl-2-(E)-butenyl 4-diphosphate synthase (IspG), and isopentenyl diphosphate isomerase (IspH).

Eukaryotic cells other than plant cells use the MEV pathway to convert acetyl-CoA to IPP, which is subsequently isomerized to DMAPP. Plants use both the mevalonate and the DXP pathways for isoprenoid synthesis. Prokaryotes, with some exceptions, use the DXP pathway to produce IPP and DMAPP separately through a branch point (see, for example Lange et al. (2000) PNAS 97:24; 13172-13177).

Whether the MEV pathway or DXP pathway is used to produce GPP, the GPP may be further modified by terpene synthases to generate specific terpenes, including tricyclene. In one embodiment, a terpene synthase acts upon the substrate GPP to produce tricyclene.

IV. Microbial Organisms

A. Host Cells

The invention provides and makes use of recombinant microbial organisms expressing a heterologous terpene synthase gene. The recombinant microbial organism may also include additional exogenous genes, such as those encoding one or more mevalonate pathway enzymes. The microbial organism can be any "host cell" that naturally produces monoterpenes or that produces monoterpenes when transformed with a gene encoding a terpene synthase.

It is understood that the progeny of a single cell may not necessarily be completely identical in morphology or in genomic or total DNA complement as the original parent, due to natural, accidental, or deliberate mutation. The host cell can be eukaryotic or prokaryotic. Suitable host cells include, but are not limited to, fungi, filamentous fungi, yeast, algae and bacteria.

In some embodiments, the transformed host cell is a eukaryotic cell. Suitable eukaryotic host cells include, but are not limited to, fungal cells, algal cells, insect cells, and plant cells. Suitable fungal host cells include, but are not limited to, yeast cells and filamentous fungal cells.

In one embodiment, the host cell is a filamentous fungus. The filamentous fungi host cells of the present invention include all filamentous forms of the subdivision Eumycotina and Oomycota (Hawksworth et al., 1995, in *Ainsworth and Bisby's Dictionary of The Fungi*, 8th ed.). Filamentous fungi are characterized by a vegetative mycelium with a cell wall composed of chitin, cellulose, and other complex polysaccharides. As used herein, the filamentous fungi host cells of the present invention are morphologically distinct from yeast. Exemplary filamentous fungal cells include, but are not limited to, species of: *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, Volvariella*, or teleomorphs, synonyms or taxonomic equivalents thereof.

In some embodiments, the filamentous fungal host cell is a species of: *Aspergillus* (e.g., *A. awamori, A. fumigatus, A. japonicus, A. nidulans, A. niger, A. aculeatus, A. foetidus, A. oryzae* and *A. kawachi*); *Chrysosporium* (*C. lucknowense, C. keratinophilum, C. tropicum, C. merdarium, C. inops, C. pannicola*, and *C. zonatum*); *Fusarium* (e.g., *F. bactridioides, F. cerealis, F. crookwellense, F. culmorum, F. graminearum, F. graminum, F. oxysporum, F. roseum*, and *F. venenatum*); *Myceliophthora* (e.g, *M. thermophilia*); *Neurospora* (e.g., *N. crassa*); or *Trichoderma* (*T. longibrachiatum, T. viride, Hypocrea jecorina* or *T. reesei*).

In one embodiment, the microbial organism is a yeast. In one embodiment, the yeast is from one of the genera: *Candida, Hansenula, Saccharomyces, Schizosaccharomyces, Pichia, Kluyveromyces*, and *Yarrowia*. In some embodiments, the yeast cell is *Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, or *Yarrowia lipolytica*.

In some embodiments, the host cell is an algal cell such as *Chlamydomonas* (e.g., *C. Reinhardtii*) and *Phormidium* (*P.* sp. ATCC29409).

In other embodiments, the host cell is a prokaryotic cell. Suitable prokaryotic cells include gram positive, gram negative and gram-variable bacterial cells. Exemplary prokaryotic host cells include, but are not limited to, species of: *Agrobac-* terium, Alicyclobacillus, Anabaena, Anacystis, Acinetobacter Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, Ilyobacter, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmun, Streptomyces, Streptococcus, Synnecoccus, Staphylococcus, Serratia, Salmonella, Shigella, Thermoanaerobacterium, Tropheryma, Tularensis, Temecula, Thermosynechococcus, Thermococcus, Ureaplasma, Xanthomonas, Xylella, Yersinia and Zymomonas.

In some embodiments, the bacterial host cell is non-pathogenic to humans. In some embodiments, the bacterial host strain is an industrial strain. Numerous bacterial industrial strains are known and suitable in the present invention.

In some embodiments, the bacterial host cell is of the Bacillus species, e.g., B. thuringiensis, B. megaterium, B. subtilis, B. lentus, B. circulans, B. pumilus, B. lautus, B. coagulans, B. brevis, B. licheniformis, B. clausii, B. stearothermophilus and B. amyloliquefaciens. In some embodiments, the bacterial host cell is of the Clostridium species, e.g., C. acetobutylicum, C. tetani E88, C. lituseburense, C. saccharobutylicum, C. perfringens, and C. beijerinckii. In some embodiments, the bacterial host cell is of the Corynebacterium species e.g., C. glutamicum and C. acetoacidophilum. In some embodiments, the bacterial host cell is of the Escherichia species, e.g., E. coli. In some embodiments the bacterial host cell is of the Erwinia species, e.g., E. uredovora, E. carotovora, E. ananas, E. herbicola, E. punctata, and E. terreus. In some embodiments, the bacterial host cell is of the Pantoea species, e.g., P. citrea and P. agglomerans. In some embodiments, the bacterial host cell is of the Pseudomonas species, e.g., P. pudita, P. mevalonii, and P. sp. D-0l 10. In some embodiments, the bacterial host cell is of the Streptococcus species, e.g., S. equisimiles, S. pyogenes, and S. uberis. In some embodiments, the bacterial host cell is of the Streptomyces species, e.g., S. ambofaciens, S. avermitilis, S. coelicolor, S. aureofaciens, S. aureus, S. fungicidicus, S. griseus, and S. lividans. In some embodiments, the bacterial host cell is of the Zymomonas species, e.g., Z. mobilis and Z. lipolytica.

Strains that may serve as suitable host cells, including both prokaryotic and eukaryotic strains, are readily accessible to the public from a number of culture collections such as American Type Culture Collection (ATCC), Deutsche Sammlung von Mikroorganismen and Zellkulturen GmbH (DSM), centraalbureau Voor Schimmelcultures (CBS), and Agricultural Research Service Patent Culture Collection, Northern Regional Research Center (NRRL).

B. Terpene Synthases and Variants Thereof

Figure 2:
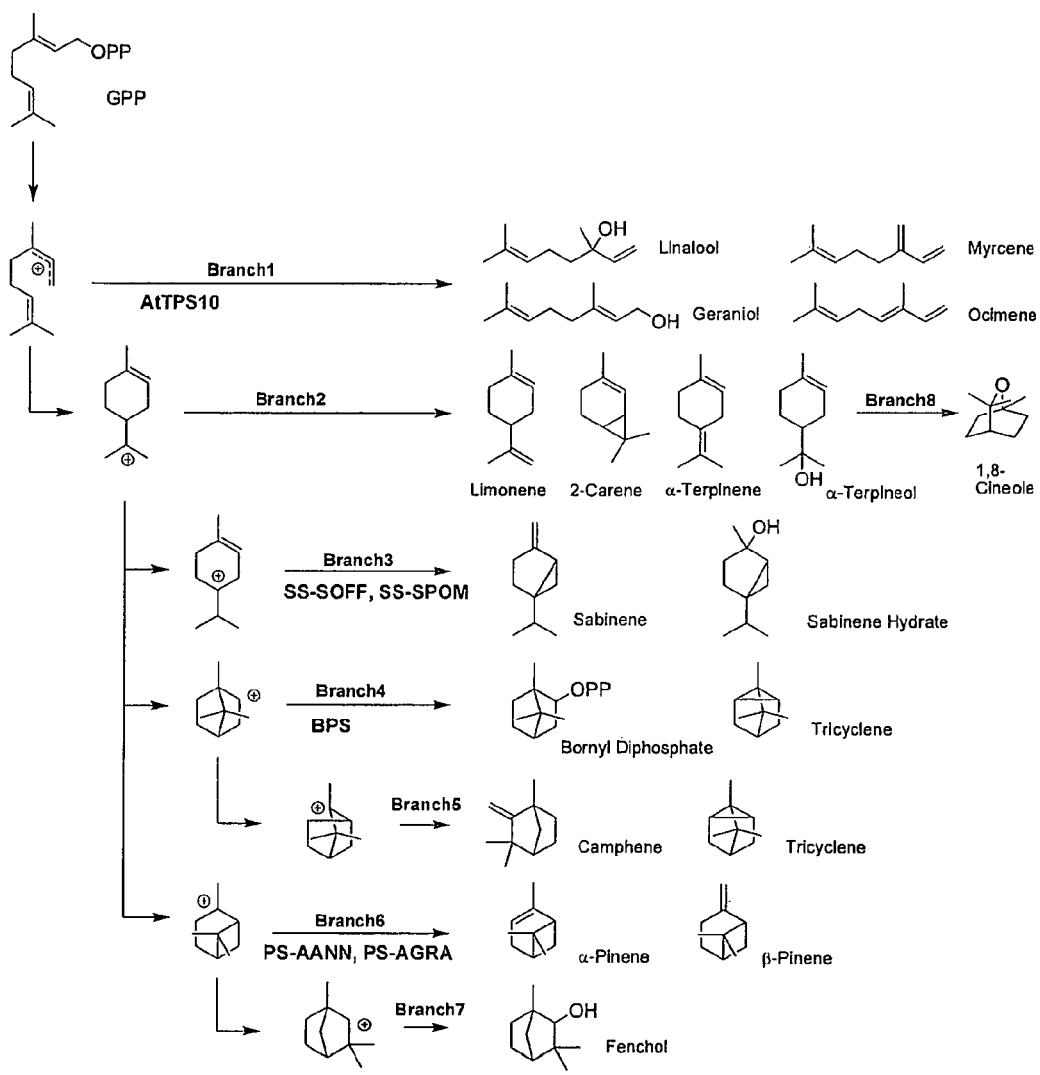
FIG. 2 depicts the cyclizations pathways for monoterpenes. Tricyclene is formed by the cyclizations cascade that proceeds through branches 4 or 5.

In one embodiment, the invention provides a method for producing a monoterpene by culturing a microbial organism expressing a heterologous terpene synthase under conditions in which the terpene synthase converts geranyl diphosphate to a monoterpene. The heterologous terpene synthase can be a wild-type heterologous terpene synthase or it can be a variant terpene synthase as described below. Such terpene synthases can be useful for producing a variety of monoterpenes including, but not limited to, the monoterpenes depicted in FIG. 2.

1. Gene and Gene Variants

In one embodiment, the terpene synthase gene is from one of Salvia officinalis, Rosemarinus offcinalis, Pseudotsuga menzeseii, Abies grandis, Arabidopsis thaliana, Mentha spicata, Artemisia annua, Ocimum basilicum, and Salvia fruticosa. In some embodiments, the terpene synthase is from one of Salvia officinalis, Rosemarinus officinalis, Pseudotsuga menzeseii, or Abies grandis.

Typically, a terpene synthase will produce one or two major terpene products and several minor terpene products. Exemplary terpene synthases and their major terpene products are described below, but are not to be limited by their representative major terpenes and proposed metabolic pathways. The exemplary terpene synthases may produce additional major terpenes, alternative major terpenes, and/or additional minor terpenes. They may also catalyze terpene production via additional and/or alternative pathways.

In one embodiment, the terpene synthase is a bornyl diphosphate synthase (BPS synthase) such as, but not limited to, those from Salvia officinalis (BPS-SOFF) (e.g., NCBI Accession No. AAC26017) and Rosemarinus officinalis (BPS-ROFF) (e.g., NCBI Accession No. ABP01684.1). Such synthases may useful to produce terpenes including, but not limited to, tricyclene. The reaction may proceed by the mechanism shown in FIG. 2, branch 4.

In another embodiment, the terpene synthase is a camphene synthase (CamS) such as, but not limited to, those from Pseudotsuga menzeseii (CamS-PMEN) (e.g., NCBI Accession No. AAX07267.1) and Abies grandis (CamS-AGR) (e.g., NCBI Accession No. AAB70707.1). Such synthases may useful to produce terpenes including, but not limited to, tricyclene and camphene. The reaction may proceed by the mechanism shown in FIG. 2, branch 5.

In one embodiment, the terpene synthase is a linear terpene synthase 10 enzyme such as, but not limited to, those from Arabidopsis thaliana (TPS10) (e.g., NCBI Accession No. NP_179998.1). Such synthases may useful to produce terpenes including, but not limited to, myrcene and ocimene. The reaction may proceed by the mechanism shown in FIG. 2, branch 1.

In another embodiment, the terpene synthase is a limonene synthase (LS) such as, but not limited to those from Mentha spicata (LS-MSPI) (e.g., NCBI Accession No. AAC37366.1). Such synthases may useful to produce terpenes including, but not limited to, limonene, 2-carene, α-terpinene, and α-terpineol. The reaction may proceed by the mechanism shown in FIG. 2, branch 2.

In another embodiment, the terpene synthase is a sabinene synthase (SS) such as, but not limited to those from Salvia officinalis (SS-SOFF) (e.g., NCBI Accession No. AAC26018.1). Such synthases may useful to produce terpenes including, but not limited to, sabinene. The reaction may proceed by the mechanism shown in FIG. 2, branch 3.

In another embodiment, the terpene synthase is a pinene synthase (PS) such as, but not limited to those from Artemisia annua (PS-AANN) (e.g., NCBI Accession No. AAK58723.1). Such synthases may useful to produce terpenes including, but not limited to, α-pinene and β-pinene. The reaction may proceed by the mechanism shown in FIG. 2, branch 6.

In another embodiment, the terpene synthase is a fenchol synthase (FS) such as, but not limited to those from Ocimum basilicum (FS-OBAS) (e.g., NCBI Accession No. AAV63790.1). Such synthases may useful to produce terpenes including, but not limited to, fenchol. The reaction may proceed by the mechanism shown in FIG. 2, branch 7.

In another embodiment, the terpene synthase is a 1,8 cineole synthase (CS) such as, but not limited to those from Salvia fruticosa (CS-SFRU) (e.g., NCBI Accession No. ABH07677.1). Such synthases may useful to produce terpenes including, but not limited to, 1,8 cineole. The reaction may proceed by the mechanism shown in FIG. 2, branch 8.

The nucleotide sequences for the terpene synthases can be codon optimized. Exemplary terpene synthases, and their corresponding terpene synthesis branch, organism source, and SEQ ID NO. are shown below in Table 1:

TABLE 1

EXEMPLARY WILD-TYPE TERPENE SYNTHASES

| Branch | Enzyme | Organism | Abbreviated name | Nucleotide SEQ ID NO. | Amino Acid SEQ ID NO. | FIG. | NCBI Accession No. |
|---|---|---|---|---|---|---|---|
| 4 | Bornyl Phosphate Synthase | Salvia officinalis | BPS-SOFF | 1 | 2 | 3 | AAC26017 |
| 4 | Bornyl Phosphate Synthase | Rosmarinus officinalis | BPS-ROFF | 3 | 4 | 4 | ABP01684.1 |
| 5 | Camphene Synthase | Pseudotsuga menziesii | CamS-PMEN | 5 | 6 | 5 | AAX07267.1 |
| 5 | Camphene Synthase | Abies grandis | CamS-AGR | 7 | 8 | 9 | AAB70707.1 |
| 1 | TPS10 | Arabidopsis thaliana | TPS10 | 9 | 10 | 10 | NP_179998.1 |
| 2 | Limonene Synthase | Mentha spicata | LS-MSPI | 11 | 12 | 11 | AAC37366.1 |
| 3 | Sabinene Synthase | Salvia officinalis | SS-SOFF | 13 | 14 | 12 | AAC26018.1 |
| 6 | Pinene Synthase | Artemisia annua | PS-AANN | 15 | 16 | 13 | AAK58723.1 |
| 7 | Fenchol Synthase | Ocimum basilicum | FS-OBAS | 17 | 18 | 14 | AAV63790.1 |
| 8 | 1,8-Cineole Synthase | Salvia fruticosa | CS-SFRU | 19 | 20 | 15 | ABH07677.1 |

The terpene synthases described above are named (e.g., bornyl phosphate synthase, camphene synthase) by reference to one of their terpene products. In one embodiment, the synthase is named by reference to a primary or major terpene product. The primary terpene product is the terpene product that is produced in the highest amount by the cell in which the wild-type enzyme is found in nature. A major terpene product is one that is produced in an amount that is more than 20%, 30%, 40%, or 50% of the total terpene production. Thus, a bornyl phosphate synthase is one that produces a detectable amount of bonyl phosphate, e.g., at least 1%, or at least 20% bornyl diphosphate as a proportion of the total terpene production. Similarly, a camphene synthase is a terpene synthase that produces a detectable amount of camphene, e.g., at least 1%, or at least 20% camphene as a proportion of the total terpene production. However, this naming convention does not require that bornyl diphosphate and cam phene are the only, or indeed the primary, monoterpene products.

It will be apparent that, although the variant sequence may be based upon the sequence for a bornyl phosphate synthase or a camphene synthase, the variant itself may or may not produce bornyl diphosphate or camphene, respectively, as a major product. The genetic modifications that increase monoterpene production, particularly tricyclene production, may decrease the relative yield for bornyl diphosphate or camphene.

As described in more detail below, the terpene synthases used herein include wild-type terpene synthases as well as variants.

In one embodiment, the heterologous terpene synthase gene encodes a terpene synthase that produces tricyclene. In some embodiments, the terpene synthase produces tricyclene via branch 4 or 5. See FIG. 2. In addition to tricyclene, branch 4 terpene synthases produce bornyl diphosphate and branch 5 terpene synthases produce camphene. Thus, bornyl diphosphate synthases and camphene synthases may be used as terpene synthases that produce tricyclene.

In one embodiment, the disclosure provides a nucleic acid encoding a terpene synthase that produces tricyclene. In some embodiments, a nucleic acid encoding a terpene synthase means that the tricyclene that is produced from the expression of the nucleic acid comprises at least 5% of the total terpenes produced by a host cell. Nucleic acid sequences encoding some preferred wild-type terpene synthases are set forth in FIGS. 3-5 and 9 (SEQ ID NOs: 1, 3, 5, and 7). However, the present invention also provides nucleic acids that encode variant terpene synthases that produce tricyclene. For example, reference is made to the variant terpene synthases disclosed in Tables 4, 5, and 6 and further as disclosed herein below under polypeptides.

In some embodiments, variant polynucleotides are nucleic acid molecules that encode a terpene synthase that produces tricyclene and that are capable of hybridizing, preferably under stringent hybridization and wash conditions, to nucleotide sequences encoding a full-length terpene synthase polypeptide that produces tricyclene as disclosed herein.

In some embodiments, the variant nucleic acid encodes a terpene synthase that produces tricyclene and has at least about 80% nucleic acid sequence identity with a nucleotide acid sequence encoding a full-length naturally occurring sequence terpene synthase polypeptide that produces tricyclene sequence as disclosed herein or any other fragment of a full-length terpene synthase polypeptide that produces tricyclene sequence as disclosed herein. Ordinarily, a variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a reference sequence, which in this case may be a nucleic acid sequence encoding a full-length native sequence terpene synthase polypeptide that produces tricyclene sequence as disclosed herein, or any other fragment of a full-length terpene synthase polypeptide that produces tricyclene sequence as disclosed herein. Variants do not encompass the naturally occurring nucleotide sequence.

In one embodiment, the variant nucleic acid is hybridizable with the wild-type or naturally occurring nucleic acid. Hybridization and washing conditions are well known and exemplified in Sambrook et al., 1989, *Molecular Cloning: A Laboratory Manual,* 2nd ed., particularly Chapter 11 and Table 11.1; and Sambrook et al., 2001, *Molecular Cloning: A Laboratory Manual,* 3rd ed. The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Hybridization conditions and post-hybridization washes are useful to obtain the desired stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C. Stringent hybridization conditions and post-hybridization wash conditions are those that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

Additionally, the nucleotide sequence of the nucleic acids can be "codon optimized." That is, the nucleotide sequences can be modified for optimal expression to reflect the codon bias of the host cell and a desired secondary structure of the transcript product mRNA. One of ordinary skill in the art will appreciate the likelihood of successful expression if codon usage is biased towards those codons favored by the host and the 5'-terminal of transcript mRNA is readily accessible to the translational machinery of the cell. Determination of preferred codons can be based on a survey of genes derived from the host cell where sequence information is available and mRNA secondary structure can be determined computationally by a variety of known computer programs, databases and calculators, such as but not limited to Encor Biotechnology's Codon Optimization Calculator.

2. Polypeptide and Polypeptide Variants

In one embodiment, the terpene synthases have the amino acid sequence as set forth in SEQ ID NOs: 2, 4, 6, and 8. However, the present invention also provides polypeptides having identity with the amino acid sequence as set forth in SEQ ID NOs: 2, 4, 6, and 8. While there is diversity in the nucleic acid and/or amino acid sequence, the function of the terpene synthase of the invention is readily apparent by detecting production of tricyclene from the recombinant cells comprising the heterologous terpene synthase.

A variant terpene synthase will have substitutions, additions, deletions, and/or insertions at certain amino acid positions compared to the naturally occurring terpene synthase. The deletions or additions may occur at the N- or C-terminus of the full length naturally occurring polypeptide. Substitutional variants will include exchange of one amino acid for another. These exchanges or substitutions can be conservative and include an exchange of amino acids with similar properties, as described herein. Alternatively, the exchanges can result in the substitution of a non-conservative amino acid, such as one that has a different charge or opposite charge. In some embodiments, substitutions will include at least 1, at least 2, at least 3, at least 4, at least 5, at least 6, at least 7, at least 8 amino acid residues. In some embodiments, the terpene synthase will include more than 10 substitutions as compared to a reference polypeptide. Insertional variants include modification to the polypeptide by addition of one or more amino acids from the reference polypeptide. Insertional mutants include an additional amino acid as compared to the reference polypeptide. Insertions can include addition of 1 or more, 2 or more, 5 or more 10 or more amino acids. Insertions can include larger additions as well. Deletional variants will include removal of one or more amino acids from a reference polypeptide. Deletions can comprise removal or 1 or more amino acids, 2 or move amino acids, 5 or more amino acids up to 10% of the total number of amino acids of the reference protein, or up to 20% of the total number of amino acids of the reference protein, or up to 30% of the total number of amino acids of the reference protein. In some embodiments, the variant terpene synthase will be a variant cyclic terpene synthase that will convert geranyl pyrophosphate to tricyclene.

In some embodiments, the variant terpene synthase will have at least about 80% amino acid sequence identity with a full-length naturally occurring terpene synthase sequence (e.g., SEQ ID NOs:2, 4 and 6) that produces tricyclene as disclosed herein. That is, a polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length naturally occurring terpene synthase sequence as disclosed herein. In some embodiments, a terpene synthase useful in the invention to produce tricyclene will include monoterpene synthases that are able to cyclize GPP via branches 4 or 5. See FIG. 2.

In one embodiment, when polypeptide variants are generated, conservative mutations are introduced into the amino acid sequence. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; a group of amino acids having sulfur-containing side chains consists of cysteine and methionine; and acidic side chains including glutamic acid and aspartic acid. Exemplary conservative amino acids substitution groups are: valine-leucine-isoleucine, phenylalanine-tyrosine, lysine-arginine, alanine-valine, and asparagine-glutamine. In some embodiments, conservative replacement will include no more than 1%, no more than 2%, no more than 5%, no more than 7%, no more than 10%, no more than 12%, or no more than 15% of the amino acid substitutions.

In some embodiments, a variant terpene synthase comprises an amino acid sequence comprising a sequence of a variant listed in Tables 4, 5, and 6. In some embodiments, the variant terpene synthase will comprise a substitution of an amino acid residue at a position corresponding to position I291, V399 and/or I404, when aligned with SEQ ID NO: 2 and having at least 90% (e.g., at least 90%, 91% 92%, 93%, 94%, 95%, 96%, 97%, 98% or 99%) sequence identity with SEQ ID NO: 2. In some embodiments, the variant comprises a substitution at position V399 corresponding to V399A, V399G, V399S, V399I or V399R and particularly V399I. In some embodiments, in addition to a substitution at a position corresponding to V399 or I404, the variant will further comprise a substitution of an amino acid residue at a one or more positions corresponding to S4, E159, G338, S267, I291, I297, K285, T460, and F525 when aligned with SEQ ID NO: 2. In some preferred aspects of this embodiment, the substitution will further encompass a substitution of S4Q, E159R, E159V, G338A, S267G, I291A, I291C, I291S, I291M, I297V, T460S, and/or F525Y. In one embodiment, a polynucleotide according to the invention will encode a terpene synthase having at least 90% sequence identity to SEQ ID NO: 2 and a substitution of amino acid residue at a position corresponding to V399 of SEQ ID NO: 2. In some embodiments the substitution will correspond to V399I.

In some embodiments, a variant terpene synthase comprises an amino acid sequence having at least 90% (e.g., at least 90%, 91% 92%, 93%, 94%, 95%, 96%, 97%, 98% or 99%) sequence identity with SEQ ID NO: 4 and comprising a substitution of an amino acid residue at a position corresponding to position H527 when aligned with SEQ ID NO: 4. In some embodiments the substitution will be H527Y.

In some embodiments, the variant terpene synthase will comprise a substitution of an amino acid residue at a position corresponding to position N18, A283, I320 and/or T431, when aligned with SEQ ID NO: 6 and having at least 90% (e.g., at least 90%, 91% 92%, 93%, 94%, 95%, 96%, 97%, 98% or 99%) sequence identity with SEQ ID NO: 6. In some embodiments, the variant comprises a substitution at position N18 corresponding to N18Q. In some embodiments, the variant comprises a substitution at position A283 corresponding to A283L. In some embodiments, the variant comprises a substitution at position I320 corresponding to I320A, I320V or I320T. In some embodiments, the variant comprises a substitution at a position T431 corresponding to T431I, T431C, T431F, T431W, T431L, T431M, or T431 V. In some embodiments, it is T431C, T431F, T431M, or T431 W. In other embodiments, in addition to the substitution at a position corresponding to position N18, A283, I320 and/or T431, the variant will comprise a substitution of an amino acid residue at one or more positions corresponding to V537, V429, and/or W392 when aligned with SEQ ID NO: 6. In some embodiments the substitution at position V429 will correspond to V429P, V429N, V429L, V429I, V429A, V429C, V429Q or V429S. In some embodiments, the substitution at W392 is W392L, W392M, or W392V. In some embodiments, in addition to or alternatively to the substitutions described above, the variant terpene synthase has a substitution at one or more of positions A376, C353, G156, K142, K491, L385, M259, P219, P434, and V537. In other embodiments, the variant terpene synthase comprises one or of the following amino acid substitutions: A376V, C353S, G156S, I320A, I320T, I320V, K142E, K491N, L385S, M259T, N18Q, P219S, P434S, T431C, T431F, T431M, T431W, V429A, V429C, V429I, V429L, V429N, V429Q, V429S, V537I, W392L, W392M, and W392V.

Performance sensitive positions, i.e., positions that have been identified as resulting in a change in monoterpene production, include positions 270, 294, 366, 373, 404, 414, 460, and 525 when numbered according to SEQ ID NO: 2. Accordingly, variant terpene synthases for use in the invention may have a mutation at one or more of these positions. Amino acid positions in a reference sequence that correspond to positions in SEQ ID NO: 2 can be determined by aligning SEQ ID NO:2 and the reference sequence (see, e.g., FIG. 16). Exemplary performance sensitive positions, and mutations that increase monoterpene production, are listed below. Suitable variant terpene synthases may include one or more of these exemplary mutations.

TABLE 2

PERFORMANCE SENSITIVE POSITIONS AND MUTATIONS

| Performance Sensitive Position (SEQ ID NO: 2) | Beneficial mutations in BPS-SOFF (SEQ ID NO: 2) | Beneficial mutations in BPS-ROFF (SEQ ID NO: 4) | Beneficial Mutations in CamS-PMEN (SEQ ID NO: 6) |
|---|---|---|---|
| 270 | W270L | | L296P |
| 294 | A294I | | I320ATV |
| 366 | V366W | | W392LMV |
| 373 | Y373H | | Y399H |
| 404 | I404ACLSTV | | C430A |
| 414 | N414S | | I440FT |
| 460 | T460S | | S485C |
| 525 | F525Y | H527Y | |

Naturally occurring terpene synthases and biologically active variants thereof catalyze the formation of a terpene, such as tricyclene, from GPP. Biological activity can be measured using art known methods. For example, the terpene synthase can be expressed in an *E. coil* expression system under appropriate culture conditions, e.g., as described in Example 2, and then one or more terpene products can be measured, e.g., by GC/MS techniques. The assay described in Example 2 is particularly useful to detect or quantitate tricyclene production.

As explained above, the terpene synthase may produce more than one monoterpene product. Individual monoterpene products or total monoterpene production can be measured by art known methods. Production of alternative monoterpenes (other than tricyclene, e.g., camphene, limonene, pinene, myrcene, borneol, terpineol, terpinolene, thujene, sabinene) can also be measured according to known methods. See, e.g., Wise et al. (1998) Monoterpene Synthases from Common Sage (*Salvia officinalis*). J Biol Chem 273(24):14891-99 and Huber et al. (2005) Characterization of four terpene synthase cDNAs from methyl jasmonate-induced Douglas-fir, *Pseudotsuga menziesii*. Phytochemistry 66: 1427-39.

In one embodiment, the variant terpene synthase exhibits improved monoterpene production (e.g., tricyclene production) as described below in section VII.B.

V. Vectors

Many embodiments of the invention utilize an expression vector that comprises a nucleotide sequence that encodes a heterologous biosynthetic pathway enzyme (e.g. the heterologous protein or polypeptide), including a terpene synthase that produces tricyclene.

Suitable exemplary vectors include, but are not limited to, viral vectors (e.g., baculovirus vectors, bacteriophage vectors, and vectors based on vaccinia virus, poliovirus, adenovirus, adeno-associated virus, SV40, herpes simplex virus, and the like), phage, plasmids, phagemids, cosmids, phosmids, bacterial artificial chromosomes (BACs), bacteriophage PI, PI-based artificial chromosomes (PACs), yeast artificial chromosomes (YACs), yeast plasmids, and any other vectors suitable for a specific host cell (e.g., *E. coli* or yeast). Preferably, the vector stably maintains and expresses a genomic DNA insert of at least 20, 50, or 75 kb. Thus, for example, a nucleic acid encoding a biosynthetic pathway enzyme, including a terpene synthase that produces tricyclene is included in any one of a variety of expression vectors for expressing the biosynthetic pathway gene product. Such vectors include chromosomal, non-chromosomal and synthetic DNA sequences, and may comprise a full or mini transposon for the integration of a desired DNA sequence into the host chromosome. Examples of transposons include but are not limited to TN5, TN7, and TN10, as well as the engineered transposons from Epicentre.

Numerous suitable expression vectors are known to those of skill in the art, and many are commercially available. The following vectors are provided by way of example: for bacterial host cells: pQE vectors (Qiagen), pBluescript plasmids, pNH vectors, lambda-ZAP vectors (Stratagene); pTrc99a, pKK223-3, pDR540, and pRIT2T (Pharmacia); for eukaryotic host cells: pXTI, pSG5 (Stratagene), pSVK3, pBPV, pMSG, and pSVLSV40 (Pharmacia). However, any other plasmid or other vector, with or without various improvements for expression, may be used so long as it is compatible with the host cell. In some embodiments, known *E. coli* expression vectors would be suitable for transforming a bacterial cell host cell and particularly an *E. coli* host with a vector comprising a polynucleotide encoding a terpene synthase according to the invention.

Standard recombinant DNA techniques can be used to perform in vitro construction of plasmid and viral chromosomes, and transformation of such into host cells including clonal propagation.

The vector can include at least one origin of replication for the host cell into which the vector is to be introduced. If also necessary, the vector can include one or more copy-control sequences for controlling the number of copies of the vector in any one cell. By way of illustration, for use in *E. coli* and other bacterial host cells, the vector preferably includes one or more bacterial origins of replication (Ori), and preferably ones that do not adversely affect gene expression in infected cells. For example, the bacterial Ori can be a pUC bacterial Ori relative (e.g., pUC, colEl, pSCIOI, pl 5A and the like). The bacterial origin of replication can also, for example, be a RK2 OriV or f 1 phage Ori. The vectors may also further include a single stranded replication origin.

The polynucleotide encoding a terpene synthase or another enzyme of interest in the expression vector is operably linked to an appropriate expression control sequence(s) (promoter) to direct synthesis of the encoded gene product. Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516-544).

In some embodiments, the promoter is inducible. Inducible promoters are well known in the art. Suitable inducible promoters include, but are not limited to, the pL of bacteriophage Plac; Ptrp; Ptac (Ptrp-lac hybrid promoter); an isopropyl-beta-D-thiogalactopyrahoside (IPTG) inducible promoter, e.g., a lacZ promoter; a tetracycline-inducible promoter; an arabinose inducible promoter, e.g., PBAD (see, e.g., Guzman et al. (1995) Bacteriol 177:4121-4130); a xylose-inducible promoter, e.g., Pxyl (see, e.g., Kim et al. (1996) Gene 181: 71-76); a GALI promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda PL promoter, a promoter controlled by a heat-sensitive repressor (e.g., CI857-repressed lambda-based expression vectors; see, e.g., Hoffmann et al. (1999) FEMS Microbiol Lett. 177(2):327-34); and the like.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), apagC promoter (Pulkkinen and Miller, J: Bacteriol., 1991: 173 (1): 86-93; Alpuche-Aranda et al., PNAS, 1992; 89(21): 10079-83), a nirB promoter (Harborn et al. (1992) Mol. Micro. 6:2805-2813), and the like (see, e.g., Dunstan et al. (1999) Infect. Immun. 67:5133-5141; McKelvie et al. (2004) Vaccine 22:3243-3255; and Chatfeld et al. (1992) Biotechnol 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) Infect. Immun. 70:1087-1096); an rpsM promoter (see, e.g., Valdivia and Falkow (1996). Mol. Microbiol 22:367-378); a tet promoter (see, e.g., Hillen, W. and Wissmann, A. (1989) In Saenger, W. and Heinemann, U. (eds), Topics in Molecular and Structural Biology, Protein-Nucleic Acid Interaction. Macmillan, London, UK, Vol. 10, pp. 143-162); an SP6 promoter (see, e.g., Melton et al. (1984; Nucl. Acids Res. 12:7035-7056); and the like. Further useful promoters for bacterial host cells include the promoter obtained from the Streptomyces coelicolor agarase gene (dagA), Bacillus subtilis levansucrase gene (sacB), Bacillus licheniformis alpha amylase (amyL), Bacillus stearothermophilus maltogenic amylase gene (amyM), Bacillus amyloliquefaciens alpha amylase gene (amyQ), Bacillus licheniformis penicillinase gene (penP), Bacillus subtilis xylA and xylB genes and prokaryotic beta-lactamase gene. These promoters are all well known in the art.

For filamentous fungal host cells suitable promoters include promoters obtained from Aspergillus oryzae TAKA amylase, Rhizomucor miehei aspartic proteinase, Aspergillus niger or awamori glucoamylase (glaA), Rhizomucor miehei lipase and the like.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N. Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast Saccharomyces, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. H5 A Practical Approach, Ed. D M Glover, 1986, IRL Press, Wash., D.C.).

In addition, the expression vectors will in many embodiments contain one or more selectable marker genes to provide a phenotypic trait for selection of transformed host cells such as dihydrofolate reductase or neomycin resistance for eukaryotic cell culture, or such as tetracycline or ampicillin resistance in prokaryotic host cells such as E. coli. Generally, recombinant expression vectors will include origins of replication and selectable markers permitting transformation of the host cell, e.g., the ampicillin resistance gene of E. coli, the S. cerevisiae TRP 1 gene, etc.; and a promoter derived from a highly expressed gene to direct transcription of the biosynthetic pathway gene product-encoding sequence. Such promoters can be derived from operons encoding glycolytic enzymes such as 3-phosphoglycerate kinase (PGK), x-factor, acid phosphatase, or heat shock proteins, among others.

Generally, DNA sequences encoding the structural coding sequence can be assembled from cDNA fragments and short oligonucleotide linkers, or from a series of synthetic oligonucleotides, to provide a synthetic nucleic acid that is capable of being expressed from a recombinant transcriptional unit contained in a cell or in a cell-free transcription and translation system. "Synthetic nucleic acids" can be assembled from oligonucleotide building blocks that are chemically synthesized using procedures known to those skilled in the art. These building blocks are ligated and annealed to form gene segments which are then enzymatically assembled to construct the entire gene. "Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms.

Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. In prokaryotic cells, permanent changes can be introduced into the chromosome or via extrachromosomal elements such as plasmids and expression vectors, which may contain one or more selectable markers to aid in their maintenance in the transformed host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

In some embodiments, a genetically modified host cell is one that is genetically modified with a nucleic acid comprising a nucleotide sequence encoding a single gene product in a biosynthesis pathway leading to the production of tricyclene. In other embodiments, a subject host cell is genetically modified with a nucleic acid comprising nucleotide sequences encoding two or more gene products in a biosynthesis pathway leading to the production of tricyclene.

Where the host cell is genetically modified to express two or more gene products in a biosynthetic pathway, nucleotide sequences encoding the two or more gene products will in some embodiments each be contained on separate expression vectors. Where the host cell is genetically modified to express two or more gene products in a biosynthetic pathway, nucleotide sequences encoding the two or more gene products will in some embodiments be contained in a single expression vector. Where nucleotide sequences encoding the two or more gene products are contained in a single expression vector, in some embodiments, the nucleotide sequences will be operably linked to a common control element (e.g., a promoter), e.g., the common control element controls expression of all of the biosynthetic pathway gene product-encoding nucleotide sequences on the single expression vector.

In some embodiments, a nucleotide sequence encoding a biosynthetic pathway gene product will be operably linked to an inducible promoter. In other embodiments, a nucleotide sequence encoding a biosynthetic pathway gene product will be operably linked to a constitutive promoter. In some embodiments, where two or more biosynthetic pathway gene products are encoded by two or more nucleotide sequences, one of the nucleotide sequences will be operably linked to an inducible promoter, and one or more of the other nucleotide sequences will be operably linked to a constitutive promoter.

The biosynthetic pathway enzymes produced by a genetically modified host cell are in some embodiments produced at a higher level than the level of such enzymes produced by a control cell, e.g., the same cell not genetically modified with one or more nucleic acids encoding a biosynthetic pathway enzyme(s). Thus, e.g., the biosynthetic pathway enzymes produced by a genetically modified host cell will in some embodiments be produced at a level that is at least 25%, at least 50%, at least 75%, at least 2-fold, or at least 5-fold, or more, higher than the level of such enzymes produced by a control cell, e.g., the same cell not genetically modified with one or more nucleic acids encoding a biosynthetic pathway enzyme(s).

In some embodiments, a genetically modified host cell comprises one or more nucleic acids that comprise nucleotide sequences encoding one or more biosynthetic pathway enzyme(s), including terpene synthases that produce tricyclene, where the nucleic acids are maintained extrachromosomally, e.g., are maintained episomally. For example, in some embodiments, the nucleic acids are plasmids or other expression vectors that do not become integrated into the genome of the genetically modified host cell. In other embodiments, the nucleic acid is integrated into the genome of the genetically modified host cell. Integration includes multiple tandem integrations, multiple non-tandem integrations, targeted integration, and random integration.

VI. Additional Metabolic Engineering

In some embodiments, the terpene synthase that produces tricyclene is co-expressed with other MEV pathway enzymes, DXP enzymes and/or prenyl transferases (See FIG. 1).

A. MEV Pathway Enzymes

The other enzyme can be an MEV pathway enzyme catalyzing any one of the MEV reaction steps: (a) condensing two molecules of acetyl-CoA to acetoacetyl-CoA; (b) condensing acetoacetyl-CoA with acetyl-CoA to form HMG-CoA; (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to isopentenyl pyrophosphate. The mevalonate pathway enzymes required for production of IPP vary depending on the culture conditions.

In some embodiments, a genetically modified host cell of the invention comprises a nucleic acid comprising nucleotide sequences encoding a mevalonate kinase (MK), as described above; a nucleic acid comprising a nucleotide sequence encoding one or more mevalonate pathway enzymes other than mevalonate kinase; and a heterologous nucleic acid comprising a nucleotide sequence encoding a terpene synthase.

Nucleotide sequences encoding MEV pathway gene products are known in the art, and any known MEV pathway gene product-encoding nucleotide sequence can used to generate a subject genetically modified host cell. For example, nucleotide sequences encoding acetoacetyl-CoA thiolase, HMGS, HMGR, MK, PMK, MPD, and IDI are known in the art. The following are non-limiting examples of known nucleotide sequences encoding MEV pathway gene products, with GenBank Accession numbers and organism following each MEV pathway enzyme, in parentheses: acetoacetyl-CoA thiolase: (NC_000913 REGION: 2324131 . . . 2325315; *E. coli*), (D49362; *Paracoccus denitrificans*), and (L20428; *Saccharomyces cerevisiae*); HMGS: (NC OOI 145. complement 19061 . . . 20536; *Saccharomyces cerevisiae*), (X96617; *Saccharomyces cerevisiae*), (X83882; *Arabidopsis thaliana*), (AB037907; *Kitasatospora griseola*), and (BT007302; *Homo sapiens*); HMGR: (NM_206548; *Drosophila melanogaster*), (NM_204485; *Gallus gallus*), (ABOI 5627; *Streptomyces sp.* KO-3988), (AF542543; *Nicotiana attenuata*), (AB037907; *Kitasatospora griseola*), (AX128213, providing the sequence encoding a truncated HMGR; *Saccharomyces cerevisiae*), and (NCjOOI 145: complement (115734 . . . 118898; *Saccharomyces cerevisiae*)); MK: (L77688; *Arabidopsis thaliana*), and (X55875; *Saccharomyces cerevisiae*); PMK: (AF429385; *Hevea brasiliensis*), (NM_006556; *Homo sapiens*), (NC_001145. complement 712315 . . . 713670; *Saccharomyces cerevisiae*); MPD: (X97557; *Saccharomyces cerevisiae*), (AF290095; Enter ococcus faecium), and (U49260; *Homo sapiens*); and IDI: (NC_000913, 3031087 . . . 3031635; *E. coli*), and (AF082326; *Haematococcus pluvialis*).

A non-limiting example of nucleotide sequences encoding acetoacetyl-CoA thiolase, HMGS3 and HMGR is set forth in FIGS. 13A-C of U.S. Pat. No. 7,183,089. A non-limiting example of nucleotide sequences encoding MK, PMK, MPD, and isopentenyl diphosphate isomerase (DDI) is set forth in FIGS. 16A-D of U.S. Pat. No. 7,183,089.

In some embodiments, the HMGR coding region is set forth in U.S. Pat. No. 7,183,089 (see also FIGS. 20A-C of U.S. Pat. No. 7,183,089), which encodes a truncated form of HMGR ("tHMGR") that lacks the transmembrane domain of wild-type HMGR. The transmembrane domain of HMGR contains the regulatory portions of the enzyme and has no catalytic activity.

The coding sequence of any known MEV pathway enzyme may be altered in various ways known in the art to generate targeted changes in the amino acid sequence of the encoded enzyme. The amino acid of a variant MEV pathway enzyme will usually be substantially similar to the amino acid sequence of any known MEV pathway enzyme, i.e. will differ by at least one amino acid, and may differ by at least two, at least 5, at least 10, or at least 20 amino acids, but typically not more than about fifty amino acids. The sequence changes may be substitutions, insertions or deletions. For example, as described below, the nucleotide sequence can be altered for the codon bias of a particular host cell. In addition, one or more nucleotide sequence differences can be introduced that result in conservative amino acid changes in the encoded protein.

B. DXP Pathway Enzymes

As described herein, in some embodiments the DXP pathway may be used to produce the biosynthetic precursors leading to the production of IPP. In one embodiment, the genetically modified host cell comprises a nucleic acid encoding a DXP pathway enzyme. Exemplary DXP pathway enzymes include, but are not limited to, 1-deoxyxylulose-5-phosphate synthase (dxs, AAC73523.1), 1-deoxy-D-xylulose 5-phosphate reductoisomerase (dxr, AAC73284.1), 4-diphosphocytidyl-2C-methyl-D-erythritol synthase (ispD, AAC75789.1), 4-diphosphocytidyl-2-C-methylerythritol kinase (ispE, AAC74292.1), 2C-methyl-D-erythritol 2,4-cyclodiphosphate synthase (ispF, AAC75788.1), 1-hydroxy-2-methyl-2-(E)-butenyl 4-diphosphate synthase (ispG, AAC75568.1), and 4-hydroxy-3-methylbut-2-enyl diphosphate reductase (ispH, AAC73140.1). In some embodiments, an endogenous DXP pathway in the host cell is functionally disabled.

C. Prenyl Transferases

In some embodiments, a genetically modified host cell comprises a nucleic acid comprising nucleotide sequences encoding a biologically active prenyl transferase.

Naturally occurring prenyl transferases and biologically active variants thereof catalyze the formation of prenyl diphosphates (see FIG. 1). For example, the enzyme may catalyze the formation of prenyl diphosphates (e.g., GPP) when expressed in an $E.$ $coli$ expression system under appropriate culture conditions, e.g., as described in Example 2. The prenyl diphosphates produced by the prenyl transferase can have various chain lengths. Suitable prenyl transferases include enzymes that catalyze the condensation of IPP with allylic primer substrates to form isoprenoid compounds with about 2 isoprene units to about 6000 isoprene units or more, e.g., 2 isoprene units (geranyl pyrophosphate synthase), 3 isoprene units (farnesyl pyrophosphate synthase), 4 isoprene units (geranylgeranyl pyrophosphate synthase), 5 isoprene units, 6 isoprene units (hexadecylpyrophosphate synthase), 7 isoprene units, 8 isoprene units (phytoene synthase, octaprenyl pyrophosphate synthase), 9 isoprene units (nonaprenyl pyrophosphate synthase), or 10 isoprene units (decaprenyl pyrophosphate synthase). Suitable prenyl transferases include, but are not limited to, geranyl diphosphate (GPP) synthase, farnesyl diphosphate (FPP) synthase, geranylgeranyl diphosphate (GGPP) synthase, hexaprenyl diphosphate (HexPP) synthase, heptaprenyl diphosphate (HepPP) synthase, octaprenyl (OPP) diphosphate synthase, solanesyl diphosphate (SPP) synthase, decaprenyl diphosphate (DPP) synthase, chicle synthase, and gutta-percha synthase; and a Z-isoprenyl diphosphate synthase, including, but not limited to, nonaprenyl diphosphate (NPP) synthase, undecaprenyl diphosphate (UPP) synthase, dehydrodolichyl diphosphate synthase, eicosaprenyl diphosphate synthase, natural rubber synthase, and other Z-isoprenyl diphosphate synthases and variants thereof.

In one embodiment, the prenyl transferase enzyme catalyzes the formation of GPP from IPP and DMAPP. In some embodiments, the prenyl transferase has been genetically modified to produce more GPP, or a higher GPP:FPP ratio than the wild-type prenyl transferase from which it was derived. Such comparative production can be measured, e.g., by expressing the genetically modified prenyl transferase and the reference prenyl transferase (e.g., wild-type IspA or in some embodiments, IspA mutant S80F) in $E.$ $coli$ under similar conditions, such as those in Example 2. Exemplary GPP synthases are disclosed in U.S. Application 61/319,586. In one embodiment, the GPP synthase has at least 90% sequence identity to wild-type IspA from $E.$ $coli$, and has an amino acid substitution corresponding to M154 and/or Q158. The substitution at M154 can be, e.g., H, Y, or W. The substitution at Q158 can be, e.g., M, F, L, or W. In some embodiments, the GPP synthase also has an amino acid substitution at position L112, e.g., L112H or L112Y. In some embodiments, it also comprises the substitution S80F. In some embodiments, GPP synthase also has amino acid substitutions at one or more of V32, A54, I76, P99, R136, I139, A159, L162, G201, K237, A241, and L290 (e.g., V32A, A54V, I76V, P99S, R136C, I139V, A159M, A159S, L162M, G201Q, K237N, A241V, and L290P).

The nucleotide sequences of numerous prenyl transferases from a variety of species are known, and can be used or modified for use in generating a genetically modified host cell. See, e.g., Human farnesyl pyrophosphate synthetase mRNA (GenBank Accession No. J05262; *Homo sapiens*); farnesyl diphosphate synthetase (FPP) gene (GenBank Accession No. J05091; *Saccharomyces cerevisiae*); isopentenyl diphosphate:dimethylallyl diphosphate isomerase gene (J05090; *Saccharomyces cerevisiae*); Wang and Ohnuma (2000) Biochim. Biophys. Acta 1529:33-48; U.S. Pat. No. 6,645,747; *Arabidopsis thaliana* farnesyl pyrophosphate synthetase 2 (FPS2)/FPP synthetase 2/farnesyl diphosphate synthase 2 (At4g17190) mRNA (GenBank Accession No. NM_202836); Ginkgo biloba geranylgeranyl diphosphate synthase (ggpps) mRNA (GenBank Accession No. AY371321); *Arabidopsis thaliana* geranylgeranyl pyrophosphate synthase (GGPSI)/GGPP synthetase/farnesyl transferase (At4g36810) mRNA (GenBank Accession No. NM_119845); *Synechococcus elongatus* gene for farnesyl, geranylgeranyl, geranylfarnesyl, hexaprenyl, heptaprenyl diphosphate synthase (SelF-HepPS) (GenBank Accession No. AB016095).

VII. Cell Culture

In another embodiment, the invention provides a method comprising providing a microbial organism as described herein, and culturing the microbial organism under conditions in which terpenes are produced. In one embodiment, the method comprises culturing a microbial organism expressing a heterologous terpene synthase under conditions in which the terpene synthase converts geranyl diphosphate to tricyclene. In some embodiments, the microbial organism having a heterologous terpene synthase gene is capable of improved production of monoterpenes, that is, at least a 50% increase in the production of monoterpenes generally or a specifically desired monoterpene compared to the wild-type microbial organism.

"Culturing" or "cultivation" refers to growing a population of microbial cells under suitable conditions in a liquid or solid medium. In particular embodiments, culturing refers to the fermentative bioconversion of a substrate to an end-product. Conditions for the culture and production of cells, including filamentous fungi, bacterial, and yeast cells, are readily available. Cell culture media in general are set forth in Atlas and Parks, eds., 1993, *The Handbook of Microbiological Media*. The individual components of such media are available from commercial sources.

In addition to convention culture conditions, in some embodiments, the culturing steps include providing an increased intracellular concentration (e.g., the concentration of the intermediate in the genetically modified host cell) of a substrate of the terpene synthase and/or a biosynthetic pathway precursor, e.g., a substrate of a MEV pathway enzyme, DXP enzyme, or prenyl transferase. The intracellular concentration of such substrates can be increased in a number of ways including, but not limited to, increasing the concentration of the substrate in the culture medium. In some embodiments, the culture medium includes mevalonate.

Various determining steps may be used to assess the impact of the genetic modifications to the host cell. For example, the method may include measuring the optical density of a liquid culture comprising the cell, or identifying a viable cell.

A. Production From Fermentable Sugars

In one embodiment, the culture medium contains fermentable sugars. Fermentable sugars are sugars that may be metabolized by a host cell. Fermentable sugars may be five-carbon (C5) sugars, six-carbon (C6) sugars, and/or oligomers of C6 and C5 sugars. Examples include, but are not limited to, glucose, fructose, sucrose, maltose, xylose, arabinose, galactose, mannose, raffinose and combinations thereof. Fermentable sugars are derived from the hydrolysis of carbohydrate polymers such as cellulose and starch. Sources of starch include plant material (such as leaves, stems, leaves, roots and grain, particularly grains derived from but not limited to corn, wheat, barley, rice, and sorghum. Exemplary feedstocks may be obtained from alfalfa, corn stover, crop residues, debarking waste, forage grasses, forest residues, municipal solid waste, paper mill residue, pomace, scraps & spoilage (fruit & vegetable processing), sawdust, spent grains, spent hops, switchgrass, waste wood chips, wood chips.

The molecular form which the digestible carbon is available in varies with the choice of feedstock. Some feedstocks will have the majority of carbon available in cellulose. In some embodiments, the method further comprising converting a cellulosic feedstock to a fermentable sugar. Other feedstocks will have a significant amount of carbon available in hemicellulose. Many feedstocks will contain lignin as well as cellulose. In some instances the lignocellulose feedstock can be pretreated using heat, acid treatment or base treatment. Therefore, the choice of feedstock degrading peptides used can be optimized depending on the structure of the chosen feedstock and whether a pretreatment is used. Possible pretreatments include the use of dilute acid, steam explosion, ammonia fiber explosion (AMFE), organic solvents (Bio-Cycle, May 2005 News Bulletin, and see: Ethanol from Cellulose: A General Review, P. Badger, p. 17-21 in J. Janick and A. Whipkey (eds.), Trends in New Crops and Uses, ASHS Press, 2002).

B. Improved Monoterpene Production

In some embodiments, levels of monoterpenes, e.g., tricyclene, can be measured as an indication of the impact of the expression of exogenous nucleic acid sequences on the host cell. Monoterpenes, e.g., tricyclene, can be detected by several methods including gas chromatography-mass spectrometry (GC-MS) and thin layer chromatography (TLC). Monoterpene production can be measured in vivo from cell culture. Alternatively, monoterpene production (e.g., terpene synthase activity) can be assessed in vitro with cell lysates or purified enzyme.

As described above, terpene synthases can produce multiple terpenes. Some of these are major products (e.g., more than 20%, 30%, 40%, or 50% of the total monoterpene production) and some are minor products (e.g., less than 20% of the total monoterpene production). According to the present invention, the microbial organisms of the present invention produce detectable levels of at least one monoterpene when cultured in vitro. More specifically, the microbial organisms of the present invention yield improved production of at least one monoterpene compared to the wild-type microbial organism. Depending on the terpene synthase used, the microbial organism can be used to produce a variety of monoterpene compounds selected from those resulting from branches 1-8 of FIG. 2. The improved monoterpene production is described below with respect to tricyclene (branches 4 and 5), but could be equally used to describe the production of an alternative desired monoterpene of branches 1-3 or 6-8.

In one embodiment, the tricyclene (or an alternative desired monoterpene) is at least 0.05% of the total monoterpene production. In some embodiments, the tricyclene is at least: 0.1%, 0.5%, 1%, 2%, 5%, 6%, 8%, 10%, 15%, 20%, 25%, 30%, 35%, 40%, or 45% of the total monoterpene production. In another embodiment, the tricyclene is about 0.1% to about 15%, about 0.5% to about 15%, about 1% to about 20%, about 1% to about 15%, or about 5% to about 20% of the total monoterpene production.

In some embodiments, the terpene synthase is a variant terpene synthase that produces increased tricyclene (or an alternative desired monoterpene) as compared to the wild-type synthase from which the variant is derived. That is, terpene synthase produces tricyclene at a level that is at least 1%, at least 2%, at least 5%, at least 10%, at least 50%, at least 75%, at least 2-fold, at least 5-fold, at least 10-fold, at least 20-fold, at least 50-fold or more, higher than the level produced by a wild-type synthase from which the variant is derived. Tricyclene production can be compared in a variety of ways, including comparing tricyclene produced by cells expressing the different synthases. In some embodiments, a variant terpene synthase produces an amount of tricyclene in a host cell greater than 50%, greater than 100%, greater than 150%, greater than 200%, as compared to a wild type terpene synthase in a corresponding host cell grown under essentially the same conditions.

In some embodiments, the host cells are capable of producing from at least about 0.001 grams, 0.005 grams, 0.01 grams, 0.05 grams, 0.1 grams, 0.2 grams, 0.3 grams, 0.4 grams, 0.5 grams, at least about 1 gram, at least about 2 grams, at least about 5 grams, at least about 10 grams, at least about 15 grams, are least about 20 grams, at least about 25 grams, at least about 30 grams, at least about 35 grams, at least about 40 grams, at least about 45 grams or at least about 50 grams of tricyclene (or an alternative desired monoterpene) per liter of fermentation medium. In some embodiments the host cells are capable of producing 0.01 to 10 gram, 0.01 to 5 grams, 0.05 to 5 grams, 0.1 to 5 grams, 0.5 to 5 grams, or 1 to 5 grams of tricyclene per liter of fermentation medium.

In some embodiments, the host cells are capable of producing from about 0.05 mg to about 1500 mg, 0.1 mg to about 1500 mg, 0.5 mg to about 1500 mg, 1 mg to about 1500 mg, 5 mg to about 1500 mg, 10 mg to about 1500 mg, 50 mg to about 1500 mg, 100 mg to about 1500 mg, 250 mg to about 1500 mg, 500 to about 1500 mg, such as more than about 10 milligrams, more than about 50 milligrams, more than about 100 milligrams, more than about 150 milligrams, more than about 200 milligrams, more than about 250 milligrams, more than about 500 milligrams, more than about 750 milligrams or more than about 1000 milligrams of tricyclene (or alternative desired monoterpene) per gram of dry cell weight cultures.

C. Recovery

The methods can further include a step of recovering, e.g., isolating, the monoterpene(s). In some embodiments, the monoterpene is secreted and/or diffuses into the culture medium, and the monoterpene is recovered from the culture medium. In other embodiments, the monoterpene is recovered from the host cells. Suitable protocols for recovering monoterpenes from recombinant host cells and/or culture medium are known to the skilled artisan. For example, wherein the aqueous medium comprises a first phase, recovering can include forming a liquid organic second phase or adding a liquid organic second phase in which the monoterpene is concentrated. The method further includes separating at least a portion of the second phase from the first phase and isolating the monoterpene from the second phase. Organic compositions that can be added to the first phase include, but are not limited to hexane, heptanes, decane, dodecane, hexadecane, ethyl acetate and methyl-t-butyl ether. In addition, hydrophobic resins such as Tenax or XAD resins can be useful to isolate the monoterpene. WO 2007/139924 expressly incorporated by reference herein describes a system for separating terpenes from aqueous media. In some embodiments, production and recovery can be performed simultaneously as a two-phase fermentation. In such embodiments, the microbial organisms can be cultured in a growth and/or production medium, with an organic phase overlay (e.g., a 10% overlay of dodecane) to facilitate recovery.

The method may include one or more additional processing components including one or more separation systems for separating the monoterpene from the aqueous media and the organic second phase, one or more reactors for biologically or chemically altering the monoterpene such as by addition, substitution, hydrogenation, alkylation, hydroxylation, condensation, halogenation or any other suitable reaction, one or more blending vessels or systems for blending the monoterpene with one or more additional components, and one or more additional purification or separation systems for further purifying the monoterpene.

The monoterpene may be isolated from the first phase and/or second phase using any suitable separation method. In some embodiments, the organic second phase occurs spontaneously as a result of chemical and molecular interactions such as differences in solubility, or hydrophobicity, density, concentration or any other spontaneous phase separation mechanism. In other embodiments, separation of the first and second phases is induced in a separation vessel or vessels or system that may be the same or a different vessel or vessels or processing system as the fermentation vessel or vessels. In some embodiments, phase separation is induced by centrifugation and/or by the introduction of a demulsifier or a nucleating agent into the fermentation reaction.

Once phase separation occurs, the separate phases can be individually drawn from the separation vessel.

In some embodiments, the monoterpene may be isolated from the organic second phase using adsorption, a process in which molecules move from a bulk liquid onto the surface of adsorbents. Isolation by adsorption may be performed using a batch, continuous or semi-continuous process. In other embodiments, the monoterpene may be isolated from the organic second phase using distillation, a method of separating substances based on differences in their volatilities. In other embodiments, the monoterpene is isolated from the organic second phase using gas-liquid extraction. This process is also known as stripping and is the transfer of a component dissolved in a liquid stream into a vapor stream in a more concentrated form. In other embodiments, the monoterpene is isolated from the organic second phase using liquid-liquid extraction. Also known as solvent extraction, liquid-liquid extraction is the transfer of a substance from one liquid phase into another immiscible liquid phase.

In a batch liquid-liquid extraction system, the feed liquid (the organic second phase) is mixed with a second immiscible liquid phase in a suitable vessel. The mixture is then permitted to settle into layers and separate into extract and raffinate and the lighter layer can be decanted from the vessel. The desired monoterpene can be in the extract or raffinate depending on the product and solvent used.

In a continuous liquid-liquid extraction system, differences in density, vapor pressure at a given temperature, or boiling points are used to separate the desired monoterpene from the feed liquid (the organic phase). Such systems can use mixer/settler tanks, towers or columns, centrifuges and combinations thereof to effect separation.

In other embodiments, the monoterpene is isolated from the organic second and/or the aqueous first phase using ultrafiltration, a pressure-driven membrane process used to separate solution components on the basis of molecular size and shape.

VIII. Fuel Compositions

The monoterpenes produced as described herein have numerous uses and can be incorporated into a chemical mixture, e.g., a fuel composition or a solvent for art restoration. In one embodiment, the monoterpene can be used as a fuel or fuel additive. For example, a gasoline fuel composition comprising monoterpene(s) and an alcohol. In some embodiments, the alcohol will be ethanol. In some embodiments, the fuel composition includes monoterpene(s) and a fuel additive.

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

EXAMPLES

Example 1

Construction of Plasmids for Monoterpene Synthase Screening

A pathway for terpene production from mevalonate was constructed in *E. coli* with a two-plasmid system consisting of genes encoding the lower MVA pathway (mevalonate kinase, phosphomevalonate kinase, diphosphomevalonate decarboxylase, isopentyl pyrophosphate isomerase, and prenyl transferase) on one plasmid, and a terpene synthase cloned on the second plasmid. Plasmid pMBIS-S80F is a derivative of pMBIS (Martin et. al, Nature Biotech. 2003, 21:796-802) containing a mutation encoding a S80F substitution in IspA, the FPP synthase from *E. coli*. This mutation changes the product selectivity of IspA so that it generates both GPP and FPP (K. K. Reiling et al, Biotechnol. Bioengin. 2004, v.87, pp. 200-212 and U.S. Pat. No. 5,935,832). The mutation was introduced into the ispA gene in pMBIS by SOE-PCR mutagenesis (Horton R M, Hunt H D, Ho S N, Pullen J K, Pease L R. Gene. (1989) 15; 77(1):61-8.). An additional plasmid for GPP production was constructed (pMBIS-IspA1.A) from pMBIS by introducing 2 different mutations (L112H; Q158M) in the ispA gene that encodes for IspA.

Figure 8:
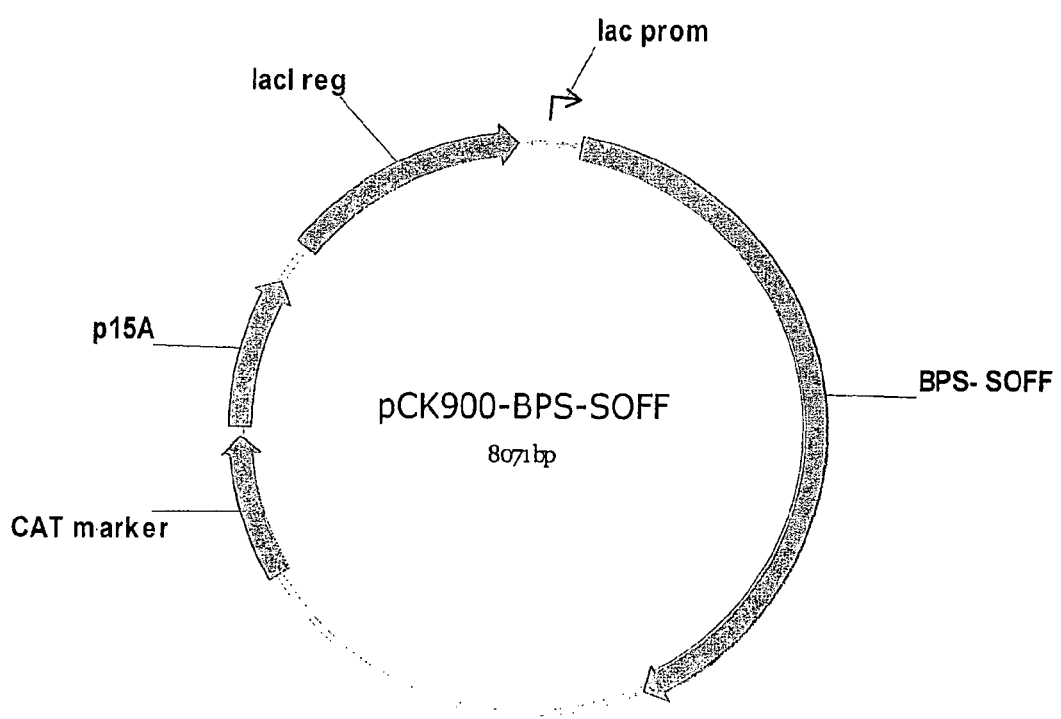
FIG. 8 depicts the plasmid map of pCK900-BPS-SOFF as further described in Example 1.

Terpene synthase genes were cloned into the *E. coli* expression vector pCK110900-I (See FIG. 3 of PCT publication WO 05/017135 and corresponding U.S. Pat. No. 7,629,157) which contains the P15A replication origin for low plasmid copy number, the chloramphenicol resistance gene camR for antibiotic selection, and a host-independent repressible promoter based on the lac regulon that contains the lacp/o promoter and the lacI repressor gene which inhibits expression in the absence of IPTG. Genes encoding plant monoterpene synthases were synthesized with flanking BglI restriction sites and codons altered for expression in *E. coli*. In addition, the plant plastid targeting sequences from the N-terminus of terpene synthases were removed since it is reported to improve expression and activity in *E. coli*. These genes were digested at 37° C. for 4 hours with BglI restriction enzyme (New England Biolabs) and purified by QIAquick PCR Purification (Qiagen) following the manufacturer's instructions. pCK110900-I was digested with BglI and purified by gel electrophoresis using QIAquick® Gel Extraction kit (Qiagen) following the manufacturer's instructions. Purified vector and inserts were ligated using T4 DNA ligase (New England Biolabs) by incubation at 16° C. for 16 hours and used to transform *E. coli* host cell line W3110 containing pMBIS-S80F or pMBIS-IspA1.A. FIG. 8 depicts plasmid pCK900-BPS-SOFF containing the bornyl diphosphate synthase from *Salvia officinalis* constructed as described above. Other terpene synthase containing plasmids were constructed in an analogous manner to pCK-BPS-SOFF. In these plasmids, the BPS-SOFF gene was substituted for CamS-PMEN and variant terpene synthases encompassed by the invention.

Example 2

Screening of Wild-Type Monoterpene Synthases

Shake-flask cultures of these strains were used to characterize in-vivo production of monoterpenes by the different cyclases. Strains harboring pMBIS-S80F or pMBIS-IspA1.A and a monoterpene synthase gene cloned in pCK110900-I plasmid were grown in M9 medium supplemented with 0.4% glucose with mevalonate additions between 1 and 40 mM, typically 20 mM. 15-50 mL cultures were grown in sealed 250 ml shake flasks or 500 mL bottles containing dodecane or heptane overlays (typically 10% v/v of the total culture) to capture volatile products and to alleviate toxicity. A typical growth and production cycle started with 5-10% v/v inoculation from overnight LB+1% glucose culture, induction with 0.5-1 mM IPTG during mid-exponential logarithmic growth phase and about 40 additional incubation hours at 30° C. and 200-250 RPM. The monoterpenes were recovered by transfer of the culture into falcon tube and removal of the organic phase by centrifugation at 4000 RPM for 15 min. If heptane was used as the organic phase it was removed directly and analyzed. If dodecane was used it was first diluted at 1:9 v/v/ ratio in ethyl acetate and then analyzed. The monoterpenes were identified and quantified by GC/MS analysis. GC/MS methods were typically either a referenced method (Adams, R. P. (2007) Identification of Essential oil Components by Gas Chromatography/Mass Spectrometry. 4th ed., Allured Pub Corp. Carol Stream, Ill.) or an isothermal method (60° C. for 6.5 min, ramped at 50° C./min to 250° C. and held for 1 min at 250° C., DB-MS5 column from Agilent, l=30 m, d=0.25 mm ID, 0.25 um df) designed to resolve tricyclene from alpha-thujene. Detection was performed in either SIM mode for m/z-93, 105, 121 & 136 ions or full scan analysis. Authentic tricyclene standard can be obtained from Chiron NS (Norway) with a purity of ~95%, and authentic tricyclene standard was used to verify the identity of GC-MS peaks corresponding to tricyclene. Other authentic commercial standards obtained from Sigma were used to validate and quantify alpha & beta-pinene, camphene, myrcene, and limonene. 3-Nitrobenzaldehyde (NBA) and m-xylene were used as internal standards for monoterpenes quantification for the reference and isothermal methods, respectively. The following synthases were tested: AtTPS10 myrcene synthase, NCBI Accession No. NM_179998 (branch 1); Myrcene synthase, NCBI Accession No. AAS47696.1 (branch 1); Carene synthase, Accession No. AAM89254.1 (branch 2); Sabinene synthase (SS-SOFF), Accession No. AAC26018.1 (branch 3); Sabinene synthase (SS-SPOM); branch 3; Bornyl-PP synthase (BPS-SOFF), Accession No. AAC26017 (branch 4); Bornyl-PP synthase (BPS-ROFF) Accession No. ABP01684.1 (branch 4); Camphene/pinene synthase (CamS-PMEN), Accession No. AAX07267.1 (branch 5); Pinene synthase (PS-AANN), Accession No. AF276072.1 (branch 6); Pinene synthase (PS-AGRA) Accession No. AAB71085.1 (branch 6); and 1, 8-Cineole synthase (CIN-SFRU), Accession No. ABH07677.1 (branch 8).

With the exception of the AtTPS10 myrcene synthase and the bornyl diphosphate synthases (BPS-SOFF and BPS-ROFF) all of the synthases tested produced the expected major corresponding monoterpene product for which they had been named. Terpene production was not detected from control samples without mevalonate or lacking the lower MVA pathway. In each case, several other minor monoterpenes were also detected. The only synthases for which tricyclene was observed were BPS-SOFF, BPS-ROFF, and CamS-PMEN as shown in Table 3.

TABLE 3

SYNTHESIZED *E. COLI* CODON OPTIMIZED MONOTERPENE CYCLASE GENES AND PRODUCT DISTRIBUTIONS INCLUDING TRICYCLENE.

| Enzyme | Source Organism | Monoterpene Products identified by GC/MS (in vivo) and estimated amounts |
|---|---|---|
| BPS-SOFF | *Salvia officinalis* | camphene (58%) limonene (16%) α-pinene (12%) myrcene (12%) borneol (unknown) tricyclene (<0.5%) |
| BPS-ROFF | *Rosmarinus oficinalis* | α-pinene (89%) camphene (3%) terpineol (2%) terpinolene (3%) limonene (2%) myrcene (1%) α-thujene (trace) tricyclene (<0.1%) |
| CamS-PMEN | *Pseudotsuga menzeseii* | α-pinene (59%) camphene (29%) sabinene (2%) limonene (3%) tricyclene (4.5%) |

Example 3

Improved Tricyclene Producing Variants

BPS-SOFF, BPS-ROFF and CamS-PMEN monoterpene synthases were subjected to directed evolution methods to improve production of tricyclene. Combinatorial and/or saturated mutagenesis libraries of variants were designed and constructed based on the reported crystal structure of BPS-SOFF and homology models.

Approximately 2400 *E. coli* colonies were screened for BPS-SOFF, 170 variants for BPS-ROFF and 2850 for CamS-PMEN. Screening was done in-vivo under high throughput conditions similar to the conditions described in Example 2 but with growth and production in 96-well plates in a total volume of 400 ul containing 10% overlay of organic solvent, typically dodecane. Extraction of the monoterpenes was performed directly with ethyl acetate, usually at a volume of 400 μl per well. Analysis of the products is described in Example 2. Several variants were found with increased tricyclene amounts, higher total terpenes productivity, and/or a higher selectivity (ratio of tricyclene to the other monoterpenes) (See Tables 4, 5, and 6).

TABLE 4

SUMMARY OF SELECTED VARIANTS FOR BPS-SOFF WHEN OPTIMALLY ALIGNED WITH SEQ ID NO: 2. TRICYCLENE PRODUCTION IS RELATIVE TO THE WILD-TYPE (WT) BPS-SOFF.

| Variant No. | Amino Acid Changes (relative to WT, SEQ ID NO: 2) | Tricyclene Production (average of n = 1 to 5 variants) | % Tricyclene of Total Monoterpenes |
|---|---|---|---|
| 1 | I404C | 2.0 | 0.6% |
| 2 | A294I; V399S; I404C | 2.2 | 0.3% |
| 3 | E125K; I404V | 1.6 | 0.8% |
| 4 | I404A | 2.0 | 0.8% |
| 5 | I404C; F525Y | 2.1 | 0.7% |
| 6 | I404C; M504V | 1.3 | 0.5% |
| 7 | I404L | 1.4 | 0.8% |
| 8 | I404S | 1.4 | 0.7% |
| 9 | I404T | 2.1 | 0.7% |
| 10 | I404V | 1.9 | 0.8% |
| 11 | N229S; I404C | 1.7 | 0.6% |
| 12 | V399A | 2.1 | 1.9% |
| 13 | V399G | 2.2 | 0.0 |
| 14 | V399I | 7.3 | 0.3% |
| 15 | D389N; V399S; T419A | 1.4 | 1.0% |
| 16 | E159R; V366W; I404C | 2.1 | 0.4% |
| 17 | V399I; E159V; R484C; F525Y | 4.7 | 0.5% |
| 18 | F69L; V399S; I404C | 3.1 | 0.8% |
| 19 | V399I; G103S; G177D; I291V; N414S | 5.7 | 0.5% |
| 20 | V399I; G338A | 8.2 | 0.3% |
| 21 | I222T; A294I; V399S; I404C | 2.2 | 0.4% |
| 22 | V399I; I291A | 50.7 | 4.3% |
| 23 | V399I; I291C | 4.8 | 2.7% |
| 24 | V399I; I291M; I297V | 20.8 | 3.8% |
| 25 | V399I; I291S | 1.1 | 2.0% |
| 26 | V399S | 2.3 | 1.1% |
| 27 | V399S; F450L | 1.3 | 0.7% |
| 28 | V399S; I404C | 3.3 | 0.8% |
| 29 | V399S; I404C; D502G | 2.9 | 0.8% |
| 30 | I73V; N178I | 1.3 | 0.6% |
| 31 | V399I; K285I | 6.2 | 0.4% |
| 32 | V399I; K85E; I291C | 5.7 | 2.7% |
| 33 | L388S; V399S; I404C | 1.9 | 0.7% |
| 34 | M274T; V399S | 1.8 | 1.1% |
| 35 | V399I; Q52R; F87L; I291C | 4.1 | 2.7% |
| 36 | Q70R; V399S | 2.2 | 1.0% |
| 37 | V399I; S115P; V203I; F525Y | 6.2 | 0.5% |
| 38 | V399I ; S267G | 15.0 | 0.6% |
| 39 | V399I ; S4Q | 7.1 | 0.3% |
| 40 | V399I; T460S | 5.2 | 0.4% |
| 41 | W270L; V399S | 2.8 | 0.4% |
| 42 | V399R | 1.8 | 0.3% |
| 43 | Y373H; I404C | 1.8 | 0.2% |

TABLE 5

SUMMARY OF SELECTED VARIANTS FOR BPS-ROFF WHEN OPTIMALLY ALIGNED WITH SEQ ID NO: 4. TRICYCLENE PRODUCTION IS RELATIVE TO THE WILD-TYPE (WT) BPS-ROFF.

| Variant No. | Amino Acid Changes (Relative to WT, SEQ ID NO: 4) | Tricyclene Production | % Tricyclene of Total Monoterpenes |
|---|---|---|---|
| 44 | H527Y | 4 | 0.1% |

TABLE 6

SUMMARY OF SELECTED VARIANTS FOR CAMS-PMEN WHEN OPTIMALLY ALIGNED WITH SEQ ID NO: 6. TRICYCLENE PRODUCTION IS RELATIVE TO THE WILD-TYPE CAMS-PMEN.

| Variant No. | Amino Acid Changes (relative to WT, SEQ ID NO: 6) | Tricyclene production (average of n = 1 to 5 variants) | % tricyclene of total monoterpenes |
|---|---|---|---|
| 45 | A283L | 1.8 | 5.3 |
| 46 | A426G | 1.8 | 4.2 |
| 47 | A53D | 0.8 | 5.1 |
| 48 | A89V; T431V | 1.7 | 3.7 |
| 49 | C430A | 2.5 | 1.3 |
| 50 | G308A | 1.3 | 4.7 |
| 51 | G312S; I320V | 1.4 | 5.1 |
| 52 | G34A | 1.4 | 5.2 |
| 53 | H144Q | 1.1 | 5.1 |
| 54 | I21V; Y399H | 1.2 | 2.1 |
| 55 | I320A | 1.4 | 9.6 |
| 56 | I320V | 1.3 | 5.9 |
| 57 | K142N | 0.8 | 5.2 |
| 58 | L230F | 0.8 | 5.2 |
| 59 | L509I | 1.9 | 4.7 |
| 60 | N18Q | 3.6 | 5.6 |
| 61 | N18Q; A283L; A373G; A426G; V537I | 8.0 | 4.7 |
| 62 | N18Q; A283L; A426G | 6.8 | 4.6 |
| 63 | N18Q; A283L; A426G; L509I | 6.1 | 4.3 |
| 64 | N18Q; A283L; E416G; L509I; V537I | 6.5 | 4.4 |
| 65 | N18Q; A283L; F452L; L509I; V537I | 4.7 | 4.2 |
| 66 | N18Q; A283L; I320A; A462S; V537I | 4.8 | 9.6 |
| 67 | N18Q; A283L; I320A; V537I | 13.1 | 11.8 |
| 68 | N18Q; A283L; I320A; V537I; A376V; T431F | 12.8 | 10.4 |
| 69 | N18Q; A283L; I320A; V537I; E158G;T431G | 1.6 | 10.5 |
| 70 | N18Q; A283L; I320A; V537I; I505T | 8.0 | 12.0 |
| 71 | N18Q; A283L; I320A; V537I; P28S; T431C | 10.4 | 11.9 |
| 72 | N18Q; A283L; I320A; V537I; T431A | 7.1 | 11.6 |
| 73 | N18Q; A283L; I320A; V537I; T431C | 13.1 | 11.8 |
| 74 | N18Q; A283L; I320A; V537I; T431L | 7.6 | 9.6 |
| 75 | N18Q; A283L; I320A; V537I; T431M | 14.1 | 11.1 |
| 76 | N18Q; A283L; I320A; V537I; T431M; F452L | 12.1 | 11.3 |
| 77 | N18Q; A283L; I320A; V537I; T431Q | 12.8 | 9.1 |
| 78 | N18Q; A283L; I320A; V537I; T431V | 10.6 | 9.2 |
| 79 | N18Q; A283L; I320A; V537I; T431W | 13.6 | 10.2 |
| 80 | N18Q; A283L; I320A; V537I; T431W; P434S | 15.3 | 7.4 |
| 81 | N18Q; A283L; I320A; V537I; V429A | 15.2 | 12.1 |
| 82 | N18Q; A283L; I320A; V537I; V429C | 14.9 | 10.4 |
| 83 | N18Q; A283L; I320A; V537I; V429I | 11.0 | 11.6 |
| 84 | N18Q; A283L; I320A; V537I; V429L | 14.3 | 8.5 |
| 85 | N18Q; A283L; I320A; V537I; V429N | 12.1 | 8.1 |
| 86 | N18Q; A283L; I320A; V537I; V429P | 25.3 | 10.1 |
| 87 | N18Q; A283L; I320A; V537I; V429Q | 15.4 | 9.6 |
| 88 | N18Q; A283L; I320A; V537I; V429S | 6.6 | 9.8 |

TABLE 6-continued

SUMMARY OF SELECTED VARIANTS FOR CAMS-PMEN WHEN OPTIMALLY ALIGNED WITH SEQ ID NO: 6. TRICYCLENE PRODUCTION IS RELATIVE TO THE WILD-TYPE CAMS-PMEN.

| Variant No. | Amino Acid Changes (relative to WT, SEQ ID NO: 6) | Tricyclene production (average of n = 1 to 5 variants) | % tricyclene of total monoterpenes |
|---|---|---|---|
| 89 | N18Q; A283L; I320A; V537I; W392L | 15.3 | 10.8 |
| 90 | N18Q; A283L; I320A; V537I; W392M | 7.0 | 12.0 |
| 91 | N18Q; A283L; I320A; V537I; W392V | 9.3 | 11.2 |
| 92 | N18Q; A283L; I320T; A426G | 6.1 | 7.5 |
| 93 | N18Q; A283L; I320T; A426G; L509I | 7.2 | 7.3 |
| 94 | N18Q; A283L; I320T; A426G; T431V; V537I | 4.8 | 6.6 |
| 95 | N18Q; A283L; I320T; E393V; T431V | 2.5 | 7.0 |
| 96 | N18Q; A283L; I320T; V537I | 1.9 | 7.1 |
| 97 | N18Q; A283L; I320V; A426G; T431M; V537I | 8.7 | 5.7 |
| 98 | N18Q; A283L; K404E; A426G; T431V | 6.3 | 3.9 |
| 99 | N18Q; A283L; L509I | 6.0 | 4.6 |
| 100 | N18Q; A283L; S307G; A426G; I440T; V537I | 5.4 | 4.3 |
| 101 | N18Q; A283L; T431M; V537I | 7.6 | 4.2 |
| 102 | N18Q; A283L; T431V; L509I; V537I | 7.2 | 3.8 |
| 103 | N18Q; A283L; V537I | 6.1 | 5.0 |
| 104 | N18Q; A426G; T431V; I440F | 4.3 | 3.9 |
| 105 | N18Q; A89T; T188A; A283L; I320A; A426G; T431V; L509I | 2.1 | 4.9 |
| 106 | N18Q; E247G; V537I | 5.0 | 4.8 |
| 107 | N18Q; G312S; A426G | 3.7 | 5.7 |
| 108 | N18Q; H96R; A283L; A426G; T431M | 5.8 | 4.4 |
| 109 | N18Q; I320T; T431V; D444G; L509I | 2.7 | 7.1 |
| 110 | N18Q; K142E; A283L; I320T; L509I | 5.3 | 7.7 |
| 111 | N18Q; K142E; G156S; I320A; L385S; K491N | 1.4 | 9.6 |
| 112 | N18Q; M210T; H228R; A283L; I320A | 1.9 | 10.0 |
| 113 | N18Q; M259T; I320A | 1.8 | 10.2 |
| 114 | N18Q; N237Y; A283L; T431V; L509I | 7.1 | 4.1 |
| 115 | N18Q; N46D; H81R; A283L; L296P | 3.7 | 3.8 |
| 116 | N18Q; P219S; A283L; C353S; A426G; L509I | 8.7 | 4.6 |
| 117 | N18Q; S22P; N239S; A283L; I320T; A426G; T431V | 6.0 | 6.6 |
| 118 | N18Q; S9P; I57V; A283L; A426G; T431M; V537I | 7.1 | 3.7 |
| 119 | N18Q; T244A; I320T; V537I | 3.3 | 7.5 |
| 120 | N18Q; Y212H; A283L; I320A; L509I; V537I | 6.5 | 9.1 |
| 121 | N386D; T431I | 1.5 | 4.6 |
| 122 | S485C | 1.3 | 4.8 |
| 123 | T431C | 2.0 | 3.5 |
| 124 | T431I | 1.4 | 4.3 |
| 125 | T431I; V566A | 2.3 | 3.6 |
| 126 | T431L | 1.2 | 3.1 |
| 127 | T431M | 2.4 | 3.7 |
| 128 | T431V | 2.3 | 3.8 |
| 139 | T431V; S538C | 2.0 | 3.8 |
| 140 | V322M | 0.8 | 5.4 |

TABLE 7

TRICYCLENE PRODUCTION LEVEL IN MG/L AS MEASURED IN SHAKE FLASKS AND TRICYCLENE AS A PERCENTAGE OF TOTAL MEASURED MONOTERPENE PRODUCTION FROM STRAINS CONTAINING THE LOWER MEVALONATE PATHWAY AND BPS-SOFF AND CAMS-PMEN MONOTERPENE SYNTHASE VARIANTS IN E. COLI.

| Strain/ (Variant No. "VN") | Amino Acid Changes | Tricyclene titer (mg/l) | % Tricyclene |
|---|---|---|---|
| BPS-SOFF/VN14 | V399I | 0.3 | 0.7 |
| BPS-SOFF/VN22 | V399I; I291A | 1 | 4.0 |
| CamS-PMEN/VN67 | N18Q; A283L; I320A; V537I | 1 | 11 |

Example 4

Construction of Full Mevalonate Pathway Strains

An *E. coli* strain was constructed to heterologously express the full mevalonate pathway, by cloning the upper and lower pathways separately into two compatible plasmids. Plasmids pCEN1 and pCEN52 are two vectors from the pZ vector system (Expressys, Ruelzheim, Germany) used as backbones to derive the cloning vectors. Plasmid pCEN1 contains the ColE1 origin, Kanamycin selection, and $P_{L-tet}$ promoter elements (equivalent to pZE21 in pZ nomenclature) and pCEN52 contains the p15A origin, Ampicillin selection, and $P_{Ltet}$ promoter elements (pZS11 in pZ nomenclature). The native multiple cloning site (MCS) fragments in both vectors were replaced with new MCS fragments that would enable having unique restriction sites between each of the pathway genes. The new MCS was generated by annealing the following oligonucleotides;

(SEQ ID NO: 21)
MevMCS-F-
5'-gaattcataagcttgtgagcggccgcattgatgcatagctagcaggccggccaggtaccac-3'
and (SEQ ID NO: 22)
MevMCS-R-
5'-cccgggtggtacctggccggcctgctagctatgcatcaatgcggccgctcacaagcttatg-3'.

This fragment was ligated into pCEN1 and pCEN52 digested with EcoRI and XmaI to create pCEN54 and pCEN53 respectively. pCEN54 and pCEN53 were used for cloning the lower and upper mevalonate pathways, respectively.

Figure 6:
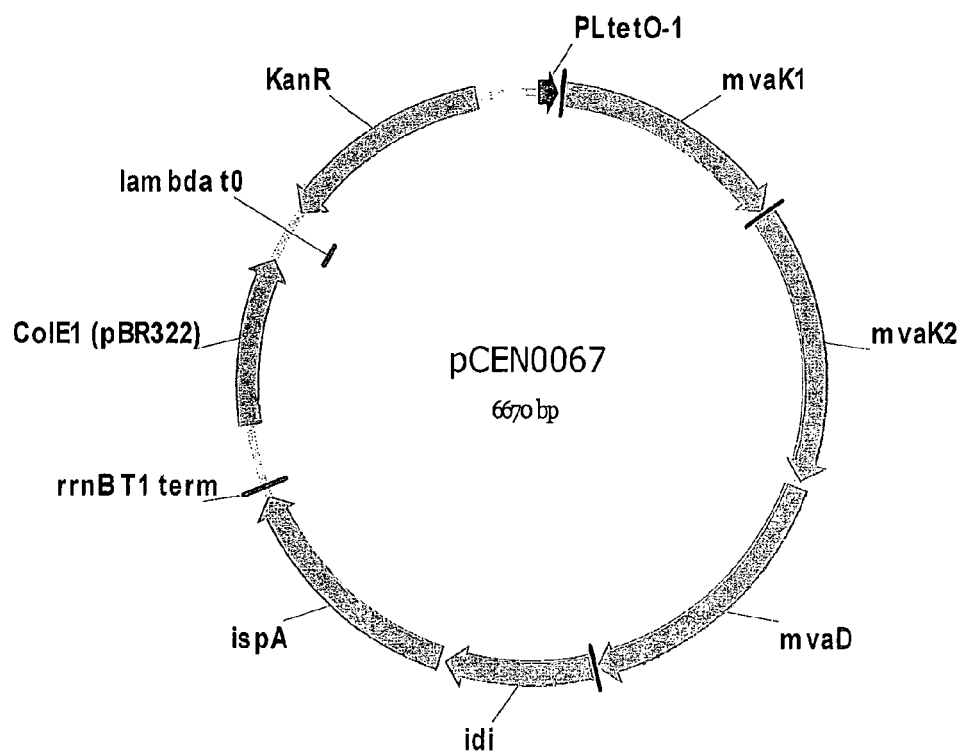
FIG. 6 depicts the plasmid map of pCEN0067 as further described in Example 4.

Lower Pathway Construct:

A lower pathway construct was made using mevalonate kinase (mvaK1), mevalonate phosphor kinase (mvak2) and mevalonate decarboxylase (mvaD) genes from *Streptococcus pneumoniae* together with the idi and ispA genes from *E. coli*. The genes were codon-optimized for expression in *E. coli*, synthesized (Gene Oracle), and cloned into pCEN54 using conventional cloning procedures to generate pCEN0067 (FIG. 6). The five gene operon is regulated by a $P_{Ltet}$ operon that was inducible by anhydrotetracycline.

Figure 7:
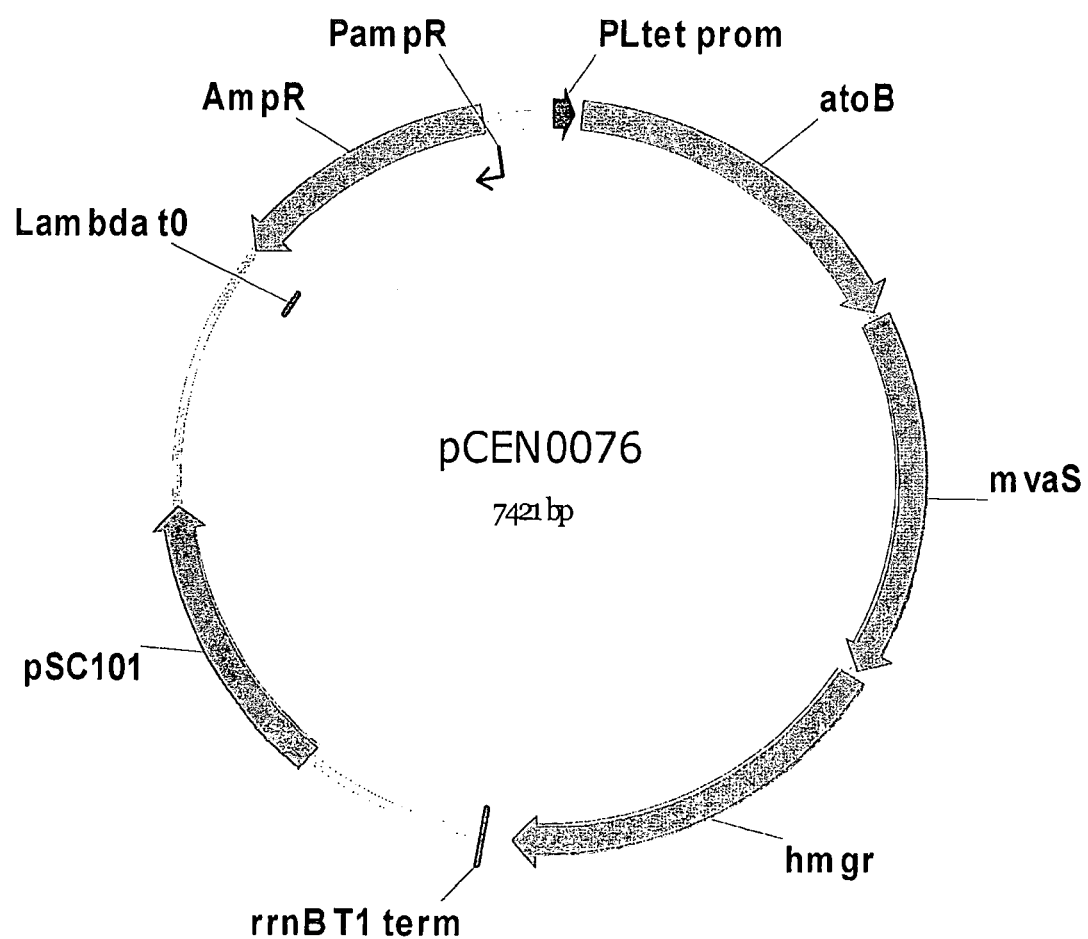
FIG. 7 depicts the plasmid map of pCEN0076 as further described in Example 4.

Upper Pathway Construct:

The upper pathway construct was made by cloning the thiolase (atoB) gene from *E. coli* together with the hmg-CoA synthase (mvaS) and hmg-CoA reductase (hmgr) genes from *S. pneumoniae* into pCEN53 to generate pCEN0076 (FIG. 7). The three gene upper pathway operon expression is also regulated by $P_{Ltet}$ promoter.

Full Mevalonate Pathway Strain:

To obtain the full mevalonate pathway strains for monoterpene production, *E. coli* W3110Z1 (Expressys) cells were first transformed with a monoterpene synthase vector described in the previous examples and also see FIG. 8. These cells were then made electrocompetent using establish molecular biology protocols. The electrocompetent cells were transformed with pCEN0067 and pCEN0076 together or sequentially. Finally, three different full pathway strains were made by transforming *E. coli* containing pCEN0067 and pCEN0076 with different terpene synthase expression plasmids, strain 1 containing BPS-SOFF (i.e. plasmid pCK900-BPS-SOFF), strain 2 containing CamS-PMEN and strain 3 containing the BPS-SOFF variant V3991.

Example 5

Tricyclene Production Using the Full MEV Pathway in *E. coli*

Strains 1, 2 and 3 were tested for tricyclene production as follows. Single colonies of the strains were used to inoculate 5 ml of LB containing 50 ug/ml carbenicillin, 30 ug/ml chloramphenicol and 40 ug/ml of kanamycin. The cultures were incubated at 37° C. and 250 rpm for 14-16 hrs. 600 ul of the starter cultures were used to inoculate 30 ml of TB (Terrific broth) media containing the same antibiotics in 250 ml shake flasks with screw caps. The cultures were incubated at 30° C. and 250 rpm for growth. Once the cultures reached an OD 0.4-0.6, the genes were induced with 100 ng/ml of anhydrotetracycline and 1 mM IPTG. At this time, the cultures were overlayed with 3 ml of dodecane. The shake flasks were screwed tight and the cultures were allowed to incubate for another 48 hrs at 30° C.

For analysis of terpene production, 6 ml of ethyl acetate containing 0.15 mg/ml of 3-nitrobenzaldehyde (3-NBA) was added to 30 ml of media. The samples were spun down at 4000 rpm for 5 min to separate the organic phase from the media. 200 ul samples were taken from the organic phase, diluted 5 fold using ethyl acetate and then analyzed by GC-MS using methods described in Example 2. 3-NBA was used as an internal standard for analysis. Tricyclene production (average of 2 replicates) from these strains is reported in Table 8.

TABLE 8

TRICYCLENE PRODUCTION LEVEL AS A PERCENTAGE OF TOTAL MEASURED MONOTERPENE PRODUCTION FROM *E. COLI* STRAINS 1, 2 AND 3.

| Strain | Tricyclene titer (mg/l) | % Tricyclene |
|---|---|---|
| 1 = WT BPS-SOFF | 0.19 | 1.1 |
| 2 = CamS-PMEN | 0.57 | 4.7 |
| 3 = BPS-SOFF/VN4 | 0.43 | 0.37 |

While various specific embodiments have been illustrated and described, it will be appreciated that various changes can be made without departing from the spirit and scope of the invention(s) described herein.

All publication, patents, patent applications, and other documents cited in this application are hereby incorporated by reference in their entireties for all purposes to the same extent as if each individual publication, patent, patent applications or other document were individually indicated to be incorporated by reference for all purposes. Although any methods and materials similar or equivalent to those described herein can also be used in the practice or testing of the present invention, the preferred methods and materials are now described.

What is claimed is:

1. A method for producing tricyclene comprising:
culturing a microbial organism expressing a heterologous terpene synthase under conditions in which the terpene synthase converts geranyl diphosphate to tricyclene, wherein the terpene synthase has at least 90% sequence identity to SEQ ID NO:2 and comprises an amino acid substitution at one or more positions corresponding to positions I291, V399, and I404 of SEQ ID NO:2.

2. The method according to claim 1, wherein the terpene synthase has at least 95% sequence identity to SEQ ID NO: 2.

3. The method according to claim 1, wherein the terpene synthase comprises an amino acid substitution at both of positions V399 and I404 of SEQ ID NO: 2.

4. The method according to claim 1, wherein the substitution at position V399 is V399A, V399G, V399I, V399R, or V399S.

5. The method according to claim 1, wherein the substitution at position I404 is I404A, I404C, I404L, I404S, I404T, or I404V.

6. The method according to claim 1, wherein the terpene synthase further comprises an amino acid substitution at one or more positions corresponding to positions W270, A294, V366, Y373, N414, T460, and F525 of SEQ ID NO: 2.

7. The method of claim 1, wherein the terpene synthase is a variant of a bornyl diphosphate synthase that produces more tricyclene than the bornyl diphosphate synthase from which it was derived, when cultured in the microbial organism under the same culture conditions.

8. The method of claim 1, wherein the microbial organism also expresses a prenyl transferase, the method further comprising contacting the prenyl transferase with IPP and DMAPP to yield geranyl pyrophosphate.

9. The method of claim 1, wherein the microbial organism is a bacterial cell or a yeast cell.

10. The method of claim 1, wherein tricyclene is produced at a level of at least 0.5% of the total monoterpene production.

11. The method of claim 1, wherein the microbial organism is cultured under fermentation conditions in a fermentation medium, and the fermentation medium comprises fermentable sugar.

12. The method of claim 11, wherein the microbial cells produce at least 0.1 mg/L tricyclene of fermentation medium.

13. The method of claim 10, further comprising recovering the tricyclene.

14. The method according to claim 13, further comprising incorporating the tricyclene into a chemical mixture.

15. The method of claim 1, wherein the substitution at position I291 is I291A, I291C, I291M, I291S, or I291V.

16. The method of claim 1, wherein the terpene synthase comprises an amino acid substitution at both of positions I291 and V399 of SEQ ID NO: 2.

17. The method of claim 1, wherein the microbial organism is *E. coli*.

* * * * *

SEQUENCE LISTING

```
<160> NUMBER OF SEQ ID NOS: 23

<210> SEQ ID NO 1
<211> LENGTH: 1638
<212> TYPE: DNA
<213> ORGANISM: Artificial Sequence
<220> FEATURE:
<223> OTHER INFORMATION: Synthetic polynucleotide for codon optimized
      Salvia officinalis bornyl diphopshate synthase (bornyl-PP
      synthase, (+)-bornyl diphopshate synthase, BPS-SOFF, terpene
      synthase)

<400> SEQUENCE: 1
atgcgtcgtt ctgggaacta ccagccggct ctgtgggaca gtaattacat ccagtctctg      60
aacacacctt acaccgaaga gcgccatctg gaccgcaagg ctgagctgat cgtgcaagtc     120
cgcatcttac tgaaagagaa aatggaaccg gtacagcagc tggaactgat tcacgatttg     180
aaatatttag ggctgtctga ttttttccaa gatgagatta agaaattttt aggcgtgatc     240
tataacgaac acaaatgttt tcacaacaac gaagtggaaa aatggatttt atactttacc     300 gcattggggtt ccgcttatt gcgtcagcac ggttttaata tttctcagga tgtgtttaat     360
tgctttaaaa acgaaaaagg catcgatttt aaagcatctc tggcccaaga tacaaaaggt     420
atgctgcaac tgtatgaagc gtctttcctg ttacgtaaag gcgaagatac tctggagctg     480
gcgcgtgaat tcgccacgaa atgcctgcag aaaaaactgg atgaaggcgg taacgaaatc     540
gatgagaacc tgctgttatg gattcgtcat agcttagatt taccgctgca ctggcgtatt     600
caaagcgtag aggctcgttg gttcatcgat gcgtatgcgc gccgtccgga tatgaacccg     660
ctgattttcg aattggccaa actgaacttt aacattattc aggcgacaca tcagcaggaa     720
ttaaaagatc tgtctcgctg gtggtctcgc ctgtgcttcc cggaaaaact gccgtttgtt     780
cgtgaccgtt tagtagaatc attttttttgg gcagtgggca tgttcgaacc acaccagcac     840
ggctatcagc gtaaaatggc cgcgaccatc attgtcctgg cgactgtcat tgatgatatt     900
tatgatgtct acggtactct ggacgaactg gaactgttta cggatacttt caagcgctgg     960
gatactgaat ctattacccg tctgccatac tatatgcaac tgtgctactg gggggtccac    1020
aactatatct cggacgcagc gtatgatatt ttaaaggaac atggtttctt ttgcctgcag    1080
tatctgcgta atcggtcgt cgatttggtt gaagcatact ccacgaagc taagtggtac     1140 cacagcggtt atacccttc tttggacgaa tacctgaata ttgcgaaaat tcagttgca      1200 tcgccggcca ttatttcccc gacgtatttt acattcgcga acgctagtca tgacacggcg    1260
gtgatcgatt ccctgtacca atatcatgac atcctgtgct ggctggcat tattctgcgc    1320 ctgccggatg atctgggcac ctcttatttc gaactggcgc gtggtgacgt acctaaaacg    1380
atccagtgtt acatgaaaga aaccaatgca tcagaagaag aggcggtgga acacgttaaa    1440
tttctgattc gtgaagcctg gaaagacatg aataccgcca tcgccgcggg ctatccgttt    1500
ccggatggca tggtagcagg cgccgcgaac atcggtcgtg tggcccagtt catttatctg    1560
cacggtgacg gttttggtgt acagcactct aaaacatatg aacatattgc gggtctgctg    1620
```
tttgaaccgt atgcgtaa                                                      1638

<210> SEQ ID NO 2
<211> LENGTH: 545
<212> TYPE: PRT
<213> ORGANISM: Salvia officinalis

<400> SEQUENCE: 2

Met Arg Arg Ser Gly Asn Tyr Gln Pro Ala Leu Trp Asp Ser Asn Tyr
1               5                   10                  15

Ile Gln Ser Leu Asn Thr Pro Tyr Thr Glu Glu Arg His Leu Asp Arg
            20                  25                  30

Lys Ala Glu Leu Ile Val Gln Val Arg Ile Leu Leu Lys Glu Lys Met
        35                  40                  45

Glu Pro Val Gln Gln Leu Glu Leu Ile His Asp Leu Lys Tyr Leu Gly
    50                  55                  60

Leu Ser Asp Phe Phe Gln Asp Glu Ile Lys Glu Ile Leu Gly Val Ile
65                  70                  75                  80

Tyr Asn Glu His Lys Cys Phe His Asn Asn Glu Val Glu Lys Met Asp
                85                  90                  95

Leu Tyr Phe Thr Ala Leu Gly Phe Arg Leu Leu Arg Gln His Gly Phe
            100                 105                 110

Asn Ile Ser Gln Asp Val Phe Asn Cys Phe Lys Asn Glu Lys Gly Ile
        115                 120                 125

Asp Phe Lys Ala Ser Leu Ala Gln Asp Thr Lys Gly Met Leu Gln Leu
    130                 135                 140

Tyr Glu Ala Ser Phe Leu Leu Arg Lys Gly Glu Asp Thr Leu Glu Leu
145                 150                 155                 160

Ala Arg Glu Phe Ala Thr Lys Cys Leu Gln Lys Lys Leu Asp Glu Gly
                165                 170                 175

Gly Asn Glu Ile Asp Glu Asn Leu Leu Leu Trp Ile Arg His Ser Leu
            180                 185                 190

Asp Leu Pro Leu His Trp Arg Ile Gln Ser Val Glu Ala Arg Trp Phe
        195                 200                 205

Ile Asp Ala Tyr Ala Arg Arg Pro Asp Met Asn Pro Leu Ile Phe Glu
    210                 215                 220

Leu Ala Lys Leu Asn Phe Asn Ile Ile Gln Ala Thr His Gln Gln Glu
225                 230                 235                 240

Leu Lys Asp Leu Ser Arg Trp Trp Ser Arg Leu Cys Phe Pro Glu Lys
                245                 250                 255

Leu Pro Phe Val Arg Asp Arg Leu Val Glu Ser Phe Phe Trp Ala Val
            260                 265                 270

Gly Met Phe Glu Pro His Gln His Gly Tyr Gln Arg Lys Met Ala Ala
        275                 280                 285

Thr Ile Ile Val Leu Ala Thr Val Ile Asp Asp Ile Tyr Asp Val Tyr
    290                 295                 300

Gly Thr Leu Asp Glu Leu Glu Leu Phe Thr Asp Thr Phe Lys Arg Trp
305                 310                 315                 320

Asp Thr Glu Ser Ile Thr Arg Leu Pro Tyr Tyr Met Gln Leu Cys Tyr
                325                 330                 335

Trp Gly Val His Asn Tyr Ile Ser Asp Ala Ala Tyr Asp Ile Leu Lys
            340                 345                 350

Glu His Gly Phe Phe Cys Leu Gln Tyr Leu Arg Lys Ser Val Val Asp
        355                 360                 365

-continued

```
Leu Val Glu Ala Tyr Phe His Glu Ala Lys Trp Tyr His Ser Gly Tyr
    370                 375                 380

Thr Pro Ser Leu Asp Glu Tyr Leu Asn Ile Ala Lys Ile Ser Val Ala
385                 390                 395                 400

Ser Pro Ala Ile Ile Ser Pro Thr Tyr Phe Thr Phe Ala Asn Ala Ser
                405                 410                 415

His Asp Thr Ala Val Ile Asp Ser Leu Tyr Gln Tyr His Asp Ile Leu
            420                 425                 430

Cys Leu Ala Gly Ile Ile Leu Arg Leu Pro Asp Asp Leu Gly Thr Ser
        435                 440                 445

Tyr Phe Glu Leu Ala Arg Gly Asp Val Pro Lys Thr Ile Gln Cys Tyr
    450                 455                 460

Met Lys Glu Thr Asn Ala Ser Glu Glu Glu Ala Val Glu His Val Lys
465                 470                 475                 480

Phe Leu Ile Arg Glu Ala Trp Lys Asp Met Asn Thr Ala Ile Ala Ala
                485                 490                 495

Gly Tyr Pro Phe Pro Asp Gly Met Val Ala Gly Ala Ala Asn Ile Gly
            500                 505                 510

Arg Val Ala Gln Phe Ile Tyr Leu His Gly Asp Gly Phe Gly Val Gln
        515                 520                 525

His Ser Lys Thr Tyr Glu His Ile Ala Gly Leu Leu Phe Glu Pro Tyr
    530                 535                 540

Ala
545
```

<210> SEQ ID NO 3
<211> LENGTH: 1644
<212> TYPE: DNA
<213> ORGANISM: Artificial Sequence
<220> FEATURE:
<223> OTHER INFORMATION: Synthetic polynucleotide for codon optimized Rosemarinus officinalis bornyl diphopshate synthase (bornyl-PP synthase, BPS-ROFF, terpene synthase, monoterpene synthase, pinene synthase)

<400> SEQUENCE: 3

```
atgcgtcgta gcggtaacta tcagccgtca agttgggatt tcaattacat ccaaagcctt      60
aatacocccat acaaagaaga acgtcaactg aaccgtgaag ccgaacttat tgtccaagtg     120
aagatgttgc tgaaagagaa acgtgaatat gtaaagcagt ggaactgat tgacgatctt      180
aaatatttag gctgtctta cttcttccaa gatgagatta agaaattct gggctttatc       240
tataacgaac acaaatggtt agacaacagc gaagcggatg aacgtgattt atacttaaag    300
gcattgggtt ccgtatctt gcgtcagcac ggtttcaatg tttctcagga agtgtttgat    360
tgctttaaga tgagaaggg cagcgacttc aaagcatctc tggcccaaga taccaaaggt    420
attctgcaac tgtatgaagc ggctttcctg ttacgtgaag cgaagatac tctggagctg    480
gcgcgtgcat cgccacgaa atgcttacag aagaaactgg atgaaggcgg tgacggaatt    540
gatgagaacc tgctgtcatg gattcgtcat agcttagatt taccgctgca ctggcgtatt    600
caacgtttag aggctcgttg gttcttagat gcgtatgcgc gtcgtccgga tatgaacccg    660
ctgatctttg aattggccaa actggacttt aacattattc aggcgacata tcagcaggaa    720
ttaaaggatg tgtctcgttg gtggaatcgt ctgggcttag cggagaaact gccgtttgtt    780
cgtgaccgta ttagaaatc atatttctgg ggagtgggca tgttcgaacc aaaccagtac    840
ggctatcagc gtaagatgtc cgggatcatc attatgctgg cgactgtcat tgatgatgtt    900
```

```
tatgatgttt atggtactct ggacgaactg caactgttta cggatactat ccgtagcttt    960
agttgggata ctgaatctat ttcccaactg ccatactata tgcaactgtg ctacttggcg   1020
ttatacaact ttgtcagtga attagcgtat gataatttaa aggaacaaca tttcatttcc   1080
attccgtatc tgcataaatc ctgggtcgat ttggctgaag catacttgaa ggaagctaag   1140
tggtactaca gcggttatac cccttctttg aagaatacc tgagtaatgc gaagatctca    1200
attgcaagtc cgaacattat ttcccagttg cactttacat tagcgaactc tagtactgac   1260
aagtggagta tcgaatccct gtaccaatat cataacatcc tgaacttgtc tggcatgctt   1320
ctgcgtctgg cggatgatgt gggcaccgct cctttcgaac tgaagcgtgg tgacgtacag   1380
aaggcgatcc agtgtcacat gaaagatcgt aatgccagtg agaaggaggc gcaggaacac   1440
gttatgtttc tgcttcgtga agcctggaaa gaaatgaata ccgcaatggc tgatggctat   1500
ccgtttgcgg atgaattggt agcagccgcc gcgaacttag gtcgtgtggc ccagttcatg   1560
tatctggaag gtgacggtca tggtgtacag cactctggta ttcatcaaca aatggcgggt   1620
ctgctgtttg aaccatatac ctaa                                          1644
```

<210> SEQ ID NO 4
<211> LENGTH: 547
<212> TYPE: PRT
<213> ORGANISM: Rosemarinus officinalis

<400> SEQUENCE: 4

```
Met Arg Arg Ser Gly Asn Tyr Gln Pro Ser Ser Trp Asp Phe Asn Tyr
1               5                   10                  15

Ile Gln Ser Leu Asn Thr Pro Tyr Lys Glu Glu Arg Gln Leu Asn Arg
            20                  25                  30

Glu Ala Glu Leu Ile Val Gln Val Lys Met Leu Leu Lys Glu Lys Arg
        35                  40                  45

Glu Tyr Val Lys Gln Leu Glu Leu Ile Asp Asp Leu Lys Tyr Leu Gly
    50                  55                  60

Leu Ser Tyr Phe Phe Gln Asp Glu Ile Lys Glu Ile Leu Gly Phe Ile
65                  70                  75                  80

Tyr Asn Glu His Lys Trp Leu Asp Asn Ser Glu Ala Asp Glu Arg Asp
                85                  90                  95

Leu Tyr Leu Lys Ala Leu Gly Phe Arg Ile Leu Arg Gln His Gly Phe
            100                 105                 110

Asn Val Ser Gln Glu Val Phe Asp Cys Phe Lys Asn Glu Lys Gly Ser
        115                 120                 125

Asp Phe Lys Ala Ser Leu Ala Gln Asp Thr Lys Gly Ile Leu Gln Leu
    130                 135                 140

Tyr Glu Ala Ala Phe Leu Leu Arg Glu Gly Glu Asp Thr Leu Glu Leu
145                 150                 155                 160

Ala Arg Ala Phe Ala Thr Lys Cys Leu Gln Lys Lys Leu Asp Glu Gly
                165                 170                 175

Gly Asp Gly Ile Asp Glu Asn Leu Leu Ser Trp Ile Arg His Ser Leu
            180                 185                 190

Asp Leu Pro Leu His Trp Arg Ile Gln Arg Leu Glu Ala Arg Trp Phe
        195                 200                 205

Leu Asp Ala Tyr Ala Arg Arg Pro Asp Met Asn Pro Leu Ile Phe Glu
    210                 215                 220

Leu Ala Lys Leu Asp Phe Asn Ile Ile Gln Ala Thr Tyr Gln Gln Glu
225                 230                 235                 240
```

```
Leu Lys Asp Val Ser Arg Trp Trp Asn Arg Leu Gly Leu Ala Glu Lys
            245                 250                 255
Leu Pro Phe Val Arg Asp Arg Ile Val Glu Ser Tyr Phe Trp Gly Val
        260                 265                 270
Gly Met Phe Glu Pro Asn Gln Tyr Gly Tyr Gln Arg Lys Met Ser Gly
    275                 280                 285
Ile Ile Ile Met Leu Ala Thr Val Ile Asp Asp Val Tyr Asp Val Tyr
290                 295                 300
Gly Thr Leu Asp Glu Leu Gln Leu Phe Thr Asp Thr Ile Arg Ser Phe
305                 310                 315                 320
Ser Trp Asp Thr Glu Ser Ile Ser Gln Leu Pro Tyr Tyr Met Gln Leu
            325                 330                 335
Cys Tyr Leu Ala Leu Tyr Asn Phe Val Ser Glu Leu Ala Tyr Asp Asn
            340                 345                 350
Leu Lys Glu Gln His Phe Ile Ser Ile Pro Tyr Leu His Lys Ser Trp
            355                 360                 365
Val Asp Leu Ala Glu Ala Tyr Leu Lys Glu Ala Lys Trp Tyr Tyr Ser
        370                 375                 380
Gly Tyr Thr Pro Ser Leu Glu Glu Tyr Leu Ser Asn Ala Lys Ile Ser
385                 390                 395                 400
Ile Ala Ser Pro Asn Ile Ile Ser Gln Leu His Phe Thr Leu Ala Asn
                405                 410                 415
Ser Ser Thr Asp Lys Trp Ser Ile Glu Ser Leu Tyr Gln Tyr His Asn
            420                 425                 430
Ile Leu Asn Leu Ser Gly Met Leu Leu Arg Leu Ala Asp Asp Val Gly
        435                 440                 445
Thr Ala Pro Phe Glu Leu Lys Arg Gly Asp Val Gln Lys Ala Ile Gln
450                 455                 460
Cys His Met Lys Asp Arg Asn Ala Ser Glu Lys Glu Ala Gln Glu His
465                 470                 475                 480
Val Met Phe Leu Leu Arg Glu Ala Trp Lys Glu Met Asn Thr Ala Met
            485                 490                 495
Ala Asp Gly Tyr Pro Phe Ala Asp Glu Leu Val Ala Ala Ala Ala Asn
            500                 505                 510
Leu Gly Arg Val Ala Gln Phe Met Tyr Leu Glu Gly Asp Gly His Gly
        515                 520                 525
Val Gln His Ser Gly Ile His Gln Gln Met Ala Gly Leu Leu Phe Glu
530                 535                 540
Pro Tyr Thr
545

<210> SEQ ID NO 5
<211> LENGTH: 1713
<212> TYPE: DNA
<213> ORGANISM: Artificial Sequence
<220> FEATURE:
<223> OTHER INFORMATION: Synthetic polynucleotide for codon optimized
      Pseudotsuga menzeseii camphene/pinene synthase (CamS-PMEN,
      camphene synthase, TPS1, (-)-alpha-pinene/(-)-camphene synthase)

<400> SEQUENCE: 5
atgcgtcgtg tcggtaacta tcattctaac ttatgggacg atgatttcat taatagtctg      60
atctcaactc cttatgaagc gccatcatat cgtgaacgtg gcgagacgtt gattggtgag     120
gtgaaagaaa tcttcaacag cattagcgtg gaggacgccg gggagttgat tacccgtta    180 aatgacctga tccaacgtct gtggatggtt gacagcgtgg aacgtttagg catcgaccgt     240
```

```
cacttcaaag atgaaatcaa gagtgcactg gattatgtat atagtcattg gcgtgaagaa    300
ggcatcggct gtggtcgtga gagtgtagca actgatttaa attctacagc gttaggtctg    360
cgtaccctgc gtctgcatgg ttatccggtt agtagcgacg tgttagaaca tttcaaagac    420
cagaaagggc acttcgcttc ctgttcaagc agtagtattg agaccggtgg ggagattcgt    480
agcgtgctga acctgtttcg tgcgagtctg attgcgttcc caaacgagaa agtcatggac    540
gaagcccaaa tcttctctac cacgtattta aggaagccg tgcagaagat cccagtgagt    600
tctctgtctc gtcaaatcga atacgtcatg gaatacggtt gggataccaa cctgccacgt    660
ctggaggccc gtcactacat ccatgtgttg gccaagaca ttacctataa tgataatgaa    720
atgccctata caaatgtaga gaaactgctg gaattggcga agctggaatt taacatgttc    780
cattctttgc aacaacgtga actgaaacac ctgtcccgtt ggtggaagga tagtggtatg    840
ccagaagcga ccttaccccg tcatcgtcat gttgagtact atgccctggc aagttgtatc    900
gcgtttgaac cgcagcacag tgggttccga ttcggctttg cgaaattatg ccacattatt    960
accgtgctgg atgacatgta tgatttattc ggcaccattg atgagctgga actgtttacc    1020
gccgccatta acgttgggga ccctagtgcc accgactgct accggaata tatgaaaggt    1080
gtgtacacta tggtttatga tactatcaat gagatggcag gcgaggccca gaatgcacag    1140
ggccgtgaca cattgaacta cgcacgtgaa gcgtgggaag cctgtttaga ttcctatttg    1200
caggaggcca atggattgc aaccgggtat ctgcctagct ttgaagagta ctatgagaat    1260
ggtaaagtca gtagtgctca ccgtgtctgc accttacagc cgattctgac gttggatatt    1320
ccatttcctg atcatattct gaaagaggtg gatttcccgt ctaaactgaa cgacctggcc    1380
tgcgccgttc tgcgtctgcg tggtgatacc cgttgttatc aggccgaccg tgcgcgtggt    1440
gaagaagcca gttctatttc atgttacatg aaggataatc caggttccac tgaagaagat    1500
gcgctgaacc acatcaatgc catgcttagt gacgttatca aggaactgaa ctgggaactg    1560
ttgaagcctg acagcgtgcc gattagcgct aagaaacatg cgtatgatgt cagtcgtgca    1620
ttccattacg gctacaaata ccgtgacggt tatagcgtgg ctaatattga aattaagaac    1680
ttcgtggcta ttagtgtgct ggaacccgta taa                                 1713
```

<210> SEQ ID NO 6
<211> LENGTH: 570
<212> TYPE: PRT
<213> ORGANISM: Pseudotsuga menzeseii

<400> SEQUENCE: 6

```
Met Arg Arg Val Gly Asn Tyr His Ser Asn Leu Trp Asp Asp Phe
1               5                   10                  15

Ile Asn Ser Leu Ile Ser Thr Pro Tyr Glu Ala Pro Ser Tyr Arg Glu
            20                  25                  30

Arg Gly Glu Thr Leu Ile Gly Glu Val Lys Glu Ile Phe Asn Ser Ile
        35                  40                  45

Ser Val Glu Asp Ala Gly Glu Leu Ile Thr Pro Leu Asn Asp Leu Ile
    50                  55                  60

Gln Arg Leu Trp Met Val Asp Ser Val Glu Arg Leu Gly Ile Asp Arg
65                  70                  75                  80

His Phe Lys Asp Glu Ile Lys Ser Ala Leu Asp Tyr Val Tyr Ser His
                85                  90                  95

Trp Arg Glu Glu Gly Ile Gly Cys Gly Arg Glu Ser Val Ala Thr Asp
            100                 105                 110
```

-continued

```
Leu Asn Ser Thr Ala Leu Gly Leu Arg Thr Leu Arg Leu His Gly Tyr
    115                 120                 125

Pro Val Ser Ser Asp Val Leu Glu His Phe Lys Asp Gln Lys Gly His
130                 135                 140

Phe Ala Ser Cys Ser Ser Ser Ile Glu Thr Gly Gly Glu Ile Arg
145                 150                 155                 160

Ser Val Leu Asn Leu Phe Arg Ala Ser Leu Ile Ala Phe Pro Asn Glu
                165                 170                 175

Lys Val Met Asp Glu Ala Gln Ile Phe Ser Thr Thr Tyr Leu Lys Glu
            180                 185                 190

Ala Val Gln Lys Ile Pro Val Ser Ser Leu Ser Arg Gln Ile Glu Tyr
        195                 200                 205

Val Met Glu Tyr Gly Trp Asp Thr Asn Leu Pro Arg Leu Glu Ala Arg
    210                 215                 220

His Tyr Ile His Val Leu Gly Gln Asp Ile Thr Tyr Asn Asp Asn Glu
225                 230                 235                 240

Met Pro Tyr Thr Asn Val Glu Lys Leu Leu Glu Leu Ala Lys Leu Glu
                245                 250                 255

Phe Asn Met Phe His Ser Leu Gln Gln Arg Glu Leu Lys His Leu Ser
            260                 265                 270

Arg Trp Trp Lys Asp Ser Gly Met Pro Glu Ala Thr Phe Thr Arg His
        275                 280                 285

Arg His Val Glu Tyr Tyr Ala Leu Ala Ser Cys Ile Ala Phe Glu Pro
    290                 295                 300

Gln His Ser Gly Phe Arg Phe Gly Phe Ala Lys Leu Cys His Ile Ile
305                 310                 315                 320

Thr Val Leu Asp Asp Met Tyr Asp Leu Phe Gly Thr Ile Asp Glu Leu
                325                 330                 335

Glu Leu Phe Thr Ala Ala Ile Lys Arg Trp Asp Pro Ser Ala Thr Asp
            340                 345                 350

Cys Leu Pro Glu Tyr Met Lys Gly Val Tyr Thr Met Val Tyr Asp Thr
        355                 360                 365

Ile Asn Glu Met Ala Gly Glu Ala Gln Asn Ala Gln Gly Arg Asp Thr
    370                 375                 380

Leu Asn Tyr Ala Arg Glu Ala Trp Glu Ala Cys Leu Asp Ser Tyr Leu
385                 390                 395                 400

Gln Glu Ala Lys Trp Ile Ala Thr Gly Tyr Leu Pro Ser Phe Glu Glu
                405                 410                 415

Tyr Tyr Glu Asn Gly Lys Val Ser Ser Ala His Arg Val Cys Thr Leu
            420                 425                 430

Gln Pro Ile Leu Thr Leu Asp Ile Pro Phe Pro Asp His Ile Leu Lys
        435                 440                 445

Glu Val Asp Phe Pro Ser Lys Leu Asn Asp Leu Ala Cys Ala Val Leu
    450                 455                 460

Arg Leu Arg Gly Asp Thr Arg Cys Tyr Gln Ala Asp Arg Ala Arg Gly
465                 470                 475                 480

Glu Glu Ala Ser Ser Ile Ser Cys Tyr Met Lys Asp Asn Pro Gly Ser
                485                 490                 495

Thr Glu Glu Asp Ala Leu Asn His Ile Asn Ala Met Leu Ser Asp Val
            500                 505                 510

Ile Lys Glu Leu Asn Trp Glu Leu Leu Lys Pro Asp Ser Val Pro Ile
        515                 520                 525
```

```
Ser Ala Lys Lys His Ala Tyr Asp Val Ser Arg Ala Phe His Tyr Gly
    530                 535                 540
Tyr Lys Tyr Arg Asp Gly Tyr Ser Val Ala Asn Ile Glu Ile Lys Asn
545                 550                 555                 560
Phe Val Ala Ile Ser Val Leu Glu Pro Val
                565                 570
```

<210> SEQ ID NO 7
<211> LENGTH: 1683
<212> TYPE: DNA
<213> ORGANISM: Artificial Sequence
<220> FEATURE:
<223> OTHER INFORMATION: Synthetic polynucleotide for codon optimized
      Abies grandis camphene synthase (CamS-AGR, BR5-CAMS-AGR,
      (-)-camphene synthase, terpene synthase, monoterpene synthase,
      terpene cyclase, AG6.5)

<400> SEQUENCE: 7

| | | |
|---|---|---|
| atgcgtcgtg tgggtaatta ccactcaaac ttgtgggatg atgactttat tcaaagtctg | 60 |
| attagcacgc cttacggagc ccccgactat cgtgaacgtg ccgatcgttt aattggtgag | 120 |
| gtgaaagaca ttatgttcaa cttcaagagc ttggaggacg ggggaatga cctgttacaa | 180 |
| cgtctgttgt tagttgacga cgtggaacgt ttaggcatcg accgtcactt caagaaagaa | 240 |
| atcaagaccg cactggatta tgtaaatagt tattggaacg agaagggcat cggctgtggt | 300 |
| cgtgagagtg tagtaactga tttaaattct acagcgttag gtctgcgtac cctgcgtctg | 360 |
| catggttata cggttagtag cgacgtgtta aatgtgttta agacaagaa tgggcagttt | 420 |
| agttccactg caaacattca gatcgaaggg gagattcgtg gcgtgctgaa cctgtttcgt | 480 |
| gcgagtctgg ttgcgttccc aggcgagaaa gtcatggacg aagccgaaac tttctctacc | 540 |
| aagtatttac gtgaagcctt acagaagatc ccagcgagtt ctattctgtc tcttgaaatc | 600 |
| cgtgatgttc tggaatacgg ttggcatacc aacctgccac gtctggaggc ccgtaactac | 660 |
| atggatgtct ttggccaaca cacgaagaac aagaacgcag cagagaagct gctggaattg | 720 |
| gcgaagctgg aatttaacat ctttcattct ttgcaagaac gtgaactgaa cacgtgtcc | 780 |
| cgttggtgga aggatagtgg ttctccagaa atgactttct gtcgtcatcg tcatgttgag | 840 |
| tactatgccc tggcaagttg tatcgcgttt gaaccgcagc acagtgggtt ccgtttgggc | 900 |
| tttacgaaga tgtcccacct gattaccgtg ctggatgaca tgtatgatgt cttcggcacc | 960 |
| gtcgatgagc tggaactgtt tactgcaacc attaaacgtt gggaccctag tgcaatggaa | 1020 |
| tgcttaccgg aatatatgaa aggtgtgtac atgatggttt atcatactgt caatgagatg | 1080 |
| gcacgtgtgg ccgagaaagc acagggccgt gacacattga actacgcacg tcaagcgtgg | 1140 |
| gaagcctgtt tcgattccta tatgcaggag gccaaatgga ttgcaaccgg gtatctgcct | 1200 |
| acctttgaag agtacttaga gaatggtaaa gtcagtagtg ctcaccgtcc ctgcgcctta | 1260 |
| cagccgattc tgacgttgga tattccattt cctgatcata ttctgaaaga ggtggatttc | 1320 |
| ccgtctaaac tgaacgacct gatctgcatc attctgcgtc tgcgtggtga tacccgttgt | 1380 |
| tataaggccg accgtgcgcg tggtgaagaa gccagttcta tttcatgtta catgaaggat | 1440 |
| aatccaggtt taactgaaga gatgcgctg aaccacatca attcatgat tcgtgacgct | 1500 |
| atccgtgaac tgaactggga actgttgaag cctgacaata gcgtgccgat tacctccaag | 1560 |
| aagcatgcgt ttgatattag tcgtgtatgg catcacggct accgttaccg tgacggttat | 1620 |
| agcttttgcta atgtggaaac aaagtctctg gtgatgcgta ctgtgattga acccgtacca | 1680 |
| ctg | 1683 |

<210> SEQ ID NO 8
<211> LENGTH: 561
<212> TYPE: PRT
<213> ORGANISM: Abies grandis

<400> SEQUENCE: 8

```
Met Arg Arg Val Gly Asn Tyr His Ser Asn Leu Trp Asp Asp Phe
1               5                   10                  15

Ile Gln Ser Leu Ile Ser Thr Pro Tyr Gly Ala Pro Asp Tyr Arg Glu
                20                  25                  30

Arg Ala Asp Arg Leu Ile Gly Glu Val Lys Asp Ile Met Phe Asn Phe
            35                  40                  45

Lys Ser Leu Glu Asp Gly Gly Asn Asp Leu Leu Gln Arg Leu Leu Leu
    50                  55                  60

Val Asp Asp Val Glu Arg Leu Gly Ile Asp Arg His Phe Lys Lys Glu
65                  70                  75                  80

Ile Lys Thr Ala Leu Asp Tyr Val Asn Ser Tyr Trp Asn Glu Lys Gly
                85                  90                  95

Ile Gly Cys Gly Arg Glu Ser Val Val Thr Asp Leu Asn Ser Thr Ala
            100                 105                 110

Leu Gly Leu Arg Thr Leu Arg Leu His Gly Tyr Thr Val Ser Ser Asp
        115                 120                 125

Val Leu Asn Val Phe Lys Asp Lys Asn Gly Gln Phe Ser Ser Thr Ala
130                 135                 140

Asn Ile Gln Ile Glu Gly Glu Ile Arg Gly Val Leu Asn Leu Phe Arg
145                 150                 155                 160

Ala Ser Leu Val Ala Phe Pro Gly Glu Lys Val Met Asp Glu Ala Glu
                165                 170                 175

Thr Phe Ser Thr Lys Tyr Leu Arg Glu Ala Leu Gln Lys Ile Pro Ala
            180                 185                 190

Ser Ser Ile Leu Ser Leu Glu Ile Arg Asp Val Leu Glu Tyr Gly Trp
        195                 200                 205

His Thr Asn Leu Pro Arg Leu Glu Ala Arg Asn Tyr Met Asp Val Phe
    210                 215                 220

Gly Gln His Thr Lys Asn Lys Asn Ala Ala Glu Lys Leu Leu Glu Leu
225                 230                 235                 240

Ala Lys Leu Glu Phe Asn Ile Phe His Ser Leu Gln Glu Arg Glu Leu
                245                 250                 255

Lys His Val Ser Arg Trp Trp Lys Asp Ser Gly Ser Pro Glu Met Thr
            260                 265                 270

Phe Cys Arg His Arg His Val Glu Tyr Tyr Ala Leu Ala Ser Cys Ile
        275                 280                 285

Ala Phe Glu Pro Gln His Ser Gly Phe Arg Leu Gly Phe Thr Lys Met
    290                 295                 300

Ser His Leu Ile Thr Val Leu Asp Asp Met Tyr Asp Val Phe Gly Thr
305                 310                 315                 320

Val Asp Glu Leu Glu Leu Phe Thr Ala Thr Ile Lys Arg Trp Asp Pro
                325                 330                 335

Ser Ala Met Glu Cys Leu Pro Glu Tyr Met Lys Gly Val Tyr Met Met
            340                 345                 350

Val Tyr His Thr Val Asn Glu Met Ala Arg Val Ala Glu Lys Ala Gln
        355                 360                 365

Gly Arg Asp Thr Leu Asn Tyr Ala Arg Gln Ala Trp Glu Ala Cys Phe
```

```
                370             375             380
Asp Ser Tyr Met Gln Glu Ala Lys Trp Ile Ala Thr Gly Tyr Leu Pro
385             390             395             400

Thr Phe Glu Glu Tyr Leu Glu Asn Gly Lys Val Ser Ser Ala His Arg
                405             410             415

Pro Cys Ala Leu Gln Pro Ile Leu Thr Leu Asp Ile Pro Phe Pro Asp
                420             425             430

His Ile Leu Lys Glu Val Asp Phe Pro Ser Lys Leu Asn Asp Leu Ile
            435             440             445

Cys Ile Ile Leu Arg Leu Arg Gly Asp Thr Arg Cys Tyr Lys Ala Asp
            450             455             460

Arg Ala Arg Gly Glu Glu Ala Ser Ser Ile Ser Cys Tyr Met Lys Asp
465             470             475             480

Asn Pro Gly Leu Thr Glu Glu Asp Ala Leu Asn His Ile Asn Phe Met
                485             490             495

Ile Arg Asp Ala Ile Arg Glu Leu Asn Trp Glu Leu Leu Lys Pro Asp
            500             505             510

Asn Ser Val Pro Ile Thr Ser Lys Lys His Ala Phe Asp Ile Ser Arg
            515             520             525

Val Trp His His Gly Tyr Arg Tyr Arg Asp Gly Tyr Ser Phe Ala Asn
            530             535             540

Val Glu Thr Lys Ser Leu Val Met Arg Thr Val Ile Glu Pro Val Pro
545             550             555             560

Leu
```

<210> SEQ ID NO 9
<211> LENGTH: 1641
<212> TYPE: DNA
<213> ORGANISM: Artificial Sequence
<220> FEATURE:
<223> OTHER INFORMATION: Synthetic polynucleotide for codon optimized
      Arabidopsis thaliana TPS10 synthase (terpene synthase 10, TPS10,
      BR1-TPS10, myrcene/ocimene synthase, AT2G24210 locus, F27D4.12)

<400> SEQUENCE: 9

```
atgcgccgct cggcgaacta ccagccgtcc cgctgggatc accaccacct gctgtcggtg       60
gaaaataagt tcgccaaaga caaacgcgtt cgcgagcgcg atctgttaaa agaaaaagta      120
cgtaaaatgt tgaacgacga acagaaaacc tatctggacc agctggaatt tattgacgac      180
ttgcagaagt tgggcgtgtc gtaccacttt gaggcagaga ttgacaatat tctgacgtcc      240
tcatacaaaa aggaccgcac caacattcag gaaagtgatc tgcatgccac agctctggaa      300
tttcgtctgt tccgccagca tggtttcaac gttagcgaag acgtgtttga tgtatttatg      360
gaaaactgcg gcaaattcga tcgtgatgac atctacggtc tgatcagttt atatgaggct      420
tcctatctgt ctacgaaatt ggataagaat ctgcaaatct ttattcgtcc gtttgctacg      480
cagcagctgc gcgatttcgt ggatacacac tccaacgaag acttcggttc cgtgtgacatg      540 gttgaaattg ttgtacaggc tctggatatg ccatactact ggcagatgcg tcgtttatcg      600
acccgctggt atattgacgt ctacggtaaa cgtcaaaatt acaagaatct ggtagttgtt      660
gaatttgcaa aaattgactt taacatcgtc aggccattc accaggagga actgaaaaac      720
gtgtcatcgt ggtggatgga acaggtctg ggaagcagc tgtactttgc ccgcgaccgt       780
atcgtagaaa actactttg gaccattggc caaattcaag aaccgcagta tggttacgtt      840
cgtcaaacaa tgacgaaaat caatgcgttg ttaacgacta tcgatgacat ctatgatatc      900
```

```
tacggcacgt tggaagaact gcaactgttc actgtcgcat tcgaaaactg ggacatcaac    960
cgcctggatg aactgccgga atacatgcgt ctgtgctttc tggtcatcta acgaagtg    1020
aactcaatcg cgtgcgaaat tctgcgtacg aaaaacatca acgttattcc tttttgaaa    1080
aaaagctgga ccgacgtttc taaggcatat ctggttgaag ctaaatggta taaatctggc    1140
cacaaaccga atctggaaga atacatgcag aatgcgcgca ttagtatttc cagtccgact    1200
atcttcgtgc acttttactg cgtattctct gaccaactga gtatccaagt tctgaaaacc    1260
ttaagccagc accaacagaa tgtggttcgt tgcagttctt cagttttccg tctggcgaac    1320
gacttagtaa cttccccgga tgaattggcc cgtggcgatg tgtgcaaatc gatccaatgt    1380
tacatgtccg aaacgggtgc ctctgaagat aaagcacgca gtcacgtccg ccagatgatt    1440
aatgatctgt gggatgagat gaattatgaa aaaatggccc attcatcttc tattctgcac    1500
cacgatttta tggaaacggt gatcaactta gcccgcatgt cgcagtgcat gtatcagtat    1560
ggcgatggcc acgggtctcc ggaaaaagcg aaaattgtcg accgtgtcat gtcactgctg    1620
tttaatccta ttccgctgga t                                             1641
```

<210> SEQ ID NO 10
<211> LENGTH: 547
<212> TYPE: PRT
<213> ORGANISM: Arabidopsis thaliana

<400> SEQUENCE: 10

```
Met Arg Arg Ser Ala Asn Tyr Gln Pro Ser Arg Trp Asp His His
1               5                   10                  15

Leu Leu Ser Val Glu Asn Lys Phe Ala Lys Asp Lys Arg Val Arg Glu
                20                  25                  30

Arg Asp Leu Leu Lys Glu Lys Val Arg Lys Met Leu Asn Asp Glu Gln
            35                  40                  45

Lys Thr Tyr Leu Asp Gln Leu Glu Phe Ile Asp Asp Leu Gln Lys Leu
        50                  55                  60

Gly Val Ser Tyr His Phe Glu Ala Glu Ile Asp Asn Ile Leu Thr Ser
65                  70                  75                  80

Ser Tyr Lys Lys Asp Arg Thr Asn Ile Gln Glu Ser Asp Leu His Ala
                85                  90                  95

Thr Ala Leu Glu Phe Arg Leu Phe Arg Gln His Gly Phe Asn Val Ser
            100                 105                 110

Glu Asp Val Phe Asp Val Phe Met Glu Asn Cys Gly Lys Phe Asp Arg
        115                 120                 125

Asp Asp Ile Tyr Gly Leu Ile Ser Leu Tyr Glu Ala Ser Tyr Leu Ser
130                 135                 140

Thr Lys Leu Asp Lys Asn Leu Gln Ile Phe Ile Arg Pro Phe Ala Thr
145                 150                 155                 160

Gln Gln Leu Arg Asp Phe Val Asp Thr His Ser Asn Glu Asp Phe Gly
                165                 170                 175

Ser Cys Asp Met Val Glu Ile Val Val Gln Ala Leu Asp Met Pro Tyr
            180                 185                 190

Tyr Trp Gln Met Arg Arg Leu Ser Thr Arg Trp Tyr Ile Asp Val Tyr
        195                 200                 205

Gly Lys Arg Gln Asn Tyr Lys Asn Leu Val Val Val Glu Phe Ala Lys
210                 215                 220

Ile Asp Phe Asn Ile Val Gln Ala Ile His Gln Glu Glu Leu Lys Asn
225                 230                 235                 240
```

```
Val Ser Ser Trp Trp Met Glu Thr Gly Leu Gly Lys Gln Leu Tyr Phe
            245                 250                 255
Ala Arg Asp Arg Ile Val Glu Asn Tyr Phe Trp Thr Ile Gly Gln Ile
        260                 265                 270
Gln Glu Pro Gln Tyr Gly Tyr Val Arg Gln Thr Met Thr Lys Ile Asn
    275                 280                 285
Ala Leu Leu Thr Thr Ile Asp Asp Ile Tyr Asp Ile Tyr Gly Thr Leu
290                 295                 300
Glu Glu Leu Gln Leu Phe Thr Val Ala Phe Glu Asn Trp Asp Ile Asn
305                 310                 315                 320
Arg Leu Asp Glu Leu Pro Glu Tyr Met Arg Leu Cys Phe Leu Val Ile
            325                 330                 335
Tyr Asn Glu Val Asn Ser Ile Ala Cys Glu Ile Leu Arg Thr Lys Asn
        340                 345                 350
Ile Asn Val Ile Pro Phe Leu Lys Lys Ser Trp Thr Asp Val Ser Lys
    355                 360                 365
Ala Tyr Leu Val Glu Ala Lys Trp Tyr Lys Ser Gly His Lys Pro Asn
370                 375                 380
Leu Glu Glu Tyr Met Gln Asn Ala Arg Ile Ser Ile Ser Ser Pro Thr
385                 390                 395                 400
Ile Phe Val His Phe Tyr Cys Val Phe Ser Asp Gln Leu Ser Ile Gln
            405                 410                 415
Val Leu Glu Thr Leu Ser Gln His Gln Asn Val Val Arg Cys Ser
        420                 425                 430
Ser Ser Val Phe Arg Leu Ala Asn Asp Leu Val Thr Ser Pro Asp Glu
    435                 440                 445
Leu Ala Arg Gly Asp Val Cys Lys Ser Ile Gln Cys Tyr Met Ser Glu
450                 455                 460
Thr Gly Ala Ser Glu Asp Lys Ala Arg Ser His Val Arg Gln Met Ile
465                 470                 475                 480
Asn Asp Leu Trp Asp Glu Met Asn Tyr Glu Lys Met Ala His Ser Ser
            485                 490                 495
Ser Ile Leu His His Asp Phe Met Glu Thr Val Ile Asn Leu Ala Arg
        500                 505                 510
Met Ser Gln Cys Met Tyr Gln Tyr Gly Asp Gly His Gly Ser Pro Glu
    515                 520                 525
Lys Ala Lys Ile Val Asp Arg Val Met Ser Leu Leu Phe Asn Pro Ile
530                 535                 540
Pro Leu Asp
545
```

<210> SEQ ID NO 11
<211> LENGTH: 1629
<212> TYPE: DNA
<213> ORGANISM: Artificial Sequence
<220> FEATURE:
<223> OTHER INFORMATION: Synthetic polynucleotide for codon optimized
      Mentha spicata limonene synthase (LS-MSPI, BR2-LS-MSPI, 4S-
      limonene synthase)

<400> SEQUENCE: 11

```
atgcgtcgta gtggtaatta taatccatca cgttgggatg tgaactttat tcagagttta      60
ttatcagatt ataaagaaga caaacatgtc attcgtgctt cagaattagt tacactggtc     120
aagatggagt tagagaagga gacggatcag attcgtcagc tggaattgat tgatgatctt     180
caacgtatgg gtctgtcaga ccactttcag aacgaattta agagatcttt atcctccatt     240
```

```
tatcttgacc accattacta caagaaccca tttcctaaag aggaacgtga tttgtacagt      300
acctcccttg cctttcgttt attgcgtgaa cacggctttc aggttgctca ggaagtgttt      360
gattctttca agaatgaaga gggagaattt aaagaatcct tgtccgatga cactcgtggt      420
ttacttcaac tgtacgaagc atccttctta ttaaccgaag cgagactac cttagaaagt       480 gcgcgtgaat tgcaacgaa attcttggag gagaaggtta acgaaggcgg tgtggacggg       540
gatttactta cccgtattgc ctattctctt gatattccac tgcattggcg tattaaacgt      600
ccgaacgcac cagtttggat cgaatggtat cgtaaacgtc cagatatgaa tccggttgtc     660
ttagagttag ccattcttga tctgaacatt gtacaagccc agttccaaga ggaattgaaa     720
gaaagtttcc gttggtggcg taacacgggt ttcgtagaga aattaccatt cgcccgtgat     780
cgtttagtcg aatgttactt ctggaacacc gggattatcg agcctcgtca gcatgcgtca     840
gcccgtatta tgatgggtaa agtcaacgcc ctgattaccg ttattgatga tatttatgat     900
gtttatggta cacttgaaga gcttgagcag tttactgacc tgattcgtcg ttgggatatt     960
aattcaattg atcagctgcc ggattacatg cagttgtgct ccttgctttt gaataatttc    1020
gtagatgaca catcctacga tgtcatgaaa gagaaagggg tgaatgtcat tccttatctt    1080
cgtcaatcat gggtagattt agcagataaa tacatggttg aagctcgttg gttctacggt    1140
ggacacaaac ccagcttaga agaatacttg gagaactcat ggcaaagtat cagcggccct    1200
tgtatgttaa cccacatctt cttccgtgtt accgactcct tcactaagga aaccgtcgat    1260
tctctttata aatatcatga tctggtacgt tggtctagct ttgtgttacg tttggcagac    1320
gatcttggga catccgtcga ggaagtgtct cgtggagatg taccgaaatc attacaatgt    1380
tacatgtctg attacaacgc atccgaagct gaagcccgta agcatgtgaa gtggttaatc    1440
gcagaagtct ggaagaagat gaatgcagag cgtgtgagta aggactctcc ctttggcaaa    1500
gactttattg gatgtgctgt tgacttaggt cgtatggctc agttaatgta tcataacggt    1560
gatggtcatg gcactcagca cccgattatt caccaacaaa tgacccgtac cctgtttgaa    1620
ccgttcgca                                                            1629
```

<210> SEQ ID NO 12
<211> LENGTH: 541
<212> TYPE: PRT
<213> ORGANISM: Artificial Sequence
<220> FEATURE:
<223> OTHER INFORMATION: Synthetic polypeptide for spearmint limonene
   synthase (LS-MSPI, BR2-LS-MSPI, 4S-limonene synthase)

<400> SEQUENCE: 12

Met Arg Arg Ser Gly Asn Tyr Asn Pro Ser Arg Trp Asp Val Asn Phe
1               5                   10                  15

Ile Gln Ser Leu Leu Ser Asp Tyr Lys Glu Asp Lys His Val Ile Arg
            20                  25                  30

Ala Ser Glu Leu Val Thr Leu Val Lys Met Glu Leu Glu Lys Glu Thr
        35                  40                  45

Asp Gln Ile Arg Gln Leu Glu Leu Ile Asp Asp Leu Gln Arg Met Gly
    50                  55                  60

Leu Ser Asp His Phe Gln Asn Glu Phe Lys Glu Ile Leu Ser Ser Ile
65                  70                  75                  80

Tyr Leu Asp His His Tyr Tyr Lys Asn Pro Phe Pro Lys Glu Glu Arg
                85                  90                  95

Asp Leu Tyr Ser Thr Ser Leu Ala Phe Arg Leu Leu Arg Glu His Gly

```
                100                 105                 110
    Phe Gln Val Ala Gln Glu Val Phe Asp Ser Phe Lys Asn Glu Glu Gly
                    115                 120                 125
    Glu Phe Lys Glu Ser Leu Ser Asp Asp Thr Arg Gly Leu Leu Gln Leu
                    130                 135                 140
    Tyr Glu Ala Ser Phe Leu Leu Thr Glu Gly Glu Thr Thr Leu Glu Ser
    145                 150                 155                 160
    Ala Arg Glu Phe Ala Thr Lys Phe Leu Glu Glu Lys Val Asn Glu Gly
                    165                 170                 175
    Gly Val Asp Gly Asp Leu Leu Thr Arg Ile Ala Tyr Ser Leu Asp Ile
                    180                 185                 190
    Pro Leu His Trp Arg Ile Lys Arg Pro Asn Ala Pro Val Trp Ile Glu
                    195                 200                 205
    Trp Tyr Arg Lys Arg Pro Asp Met Asn Pro Val Val Leu Glu Leu Ala
                    210                 215                 220
    Ile Leu Asp Leu Asn Ile Val Gln Ala Gln Phe Gln Glu Glu Leu Lys
    225                 230                 235                 240
    Glu Ser Phe Arg Trp Trp Arg Asn Thr Gly Phe Val Glu Lys Leu Pro
                    245                 250                 255
    Phe Ala Arg Asp Arg Leu Val Glu Cys Tyr Phe Trp Asn Thr Gly Ile
                    260                 265                 270
    Ile Glu Pro Arg Gln His Ala Ser Ala Arg Ile Met Met Gly Lys Val
                    275                 280                 285
    Asn Ala Leu Ile Thr Val Ile Asp Asp Ile Tyr Asp Val Val Gly Thr
                    290                 295                 300
    Leu Glu Glu Leu Glu Gln Phe Thr Asp Leu Ile Arg Arg Trp Asp Ile
    305                 310                 315                 320
    Asn Ser Ile Asp Gln Leu Pro Asp Tyr Met Gln Leu Cys Phe Leu Ala
                    325                 330                 335
    Leu Asn Asn Phe Val Asp Asp Thr Ser Tyr Asp Val Met Lys Glu Lys
                    340                 345                 350
    Gly Val Asn Val Ile Pro Tyr Leu Arg Gln Ser Trp Val Asp Leu Ala
                    355                 360                 365
    Asp Lys Tyr Met Val Glu Ala Arg Trp Phe Tyr Gly Gly His Lys Pro
                    370                 375                 380
    Ser Leu Glu Glu Tyr Leu Glu Asn Ser Trp Gln Ser Ile Ser Gly Pro
    385                 390                 395                 400
    Cys Met Leu Thr His Ile Phe Phe Arg Val Thr Asp Ser Phe Thr Lys
                    405                 410                 415
    Glu Thr Val Asp Ser Leu Tyr Lys Tyr His Asp Leu Val Arg Trp Ser
                    420                 425                 430
    Ser Phe Val Leu Arg Leu Ala Asp Asp Leu Gly Thr Ser Val Glu Glu
                    435                 440                 445
    Val Ser Arg Gly Asp Val Pro Lys Ser Leu Gln Cys Tyr Met Ser Asp
                    450                 455                 460
    Tyr Asn Ala Ser Glu Ala Glu Ala Arg Lys His Val Lys Trp Leu Ile
    465                 470                 475                 480
    Ala Glu Val Trp Lys Lys Met Asn Ala Glu Arg Val Ser Lys Asp Ser
                    485                 490                 495
    Pro Phe Gly Lys Asp Phe Ile Gly Cys Ala Val Asp Leu Gly Arg Met
                    500                 505                 510
    Ala Gln Leu Met Tyr His Asn Gly Asp Gly His Gly Thr Gln His Pro
                    515                 520                 525
```

Ile Ile His Gln Gln Met Thr Arg Thr Leu Phe Glu Pro
    530                 535                 540

<210> SEQ ID NO 13
<211> LENGTH: 1620
<212> TYPE: DNA
<213> ORGANISM: Artificial Sequence
<220> FEATURE:
<223> OTHER INFORMATION: Synthetic polynucleotide for codon optimized
      Salvia officinalis sabinene synthase (SS-SOFF, BR3-SS-SOFF,
      (+)-sabinene synthase)

<400> SEQUENCE: 13
atgcgtcgct cgggcgatta ccaaccttct ttatgggact taattatat ccagtctctg      60 aacaccccat ataaagagca gcgccatttc aaccgtcagg ctgaactgat tatgcaggtt    120
cgtatgctgc tgaaggtgaa gatggaagca attcagcagc tggaactgat tgacgatctg    180
cagtatctgg gtctgagcta cttctttcag gatgaaatca acaaattct gagctctatt    240 cacaacgaac cacgctattt tcacaataac gacttgtatt tcacggcact gggtttccgc    300 atttacgcc agcatgggtt caacgtgtca gaagacgtat tcgactgttt taaaattgaa    360
aagtgctctg atttcaacgc gaacctggcc caagatacga aaggcatgct gcagctgtat    420
gaagcaagct tttattacg tgaaggtgaa gatactttag agctggcgcg tcgcttcagc    480
acccgtagcc tgcgtgaaaa gtttgatgag ggtggtgatg aaatcgatga agatttatcc    540
agctggattc gtcattcgct ggacttaccg ttgcactggc gcgtccaagg gctggaagca    600
cgctggttcc tggatgcgta tgcccgtcgt ccggatatga atccactgat cttcaaactg    660
gcgaaattaa actttaatat tgtgcaggcc acgtaccagg aggagttaaa agatatctca    720
cgttggtgga acagtagctg cttagcggag aaattgccgt ttgtacgtga tcgcattgtg    780
gaatgttttt tttgggctat tgcggcattc gaaccacacc agtattcgta ccaacgtaaa    840
atggcggctg taattatcac ttttatcacg atcattgacg atgtctatga tgtatacggc    900
actatcgagg aactggagtt actgaccgac atgatccgtc gctgggataa taaatcgatt    960
tcgcaactgc cgtattatat gcaagtttgt tatctggctc tgtacaactt tgtatctgag   1020
cgtgcttacg atatcttaaa agaccagcac ttcaacagca tcccgtactt acagcgttcg   1080
tgggtttctt tggtagaagg gtatttaaag gaagcatatt ggtactataa cggctacaaa   1140
ccgtcgctgg aagaatacct gaataatgcg aaaatttcca tttcagctcc gactattatt   1200
agccaactgt atttttacct ggcgaatagt atcgatgaga ctgctatcga gagcttgtat   1260
cagtatcaca catcctgta tttgtcgggg accatcttac gcctggccga cgatctgggc   1320
acttcgcaac atgagttgga gcgcgggat gtgccgaaag cgattcaatg ttacatgaac   1380
gatacaaatg cgtcggaacg cgaggcagta gaacacgtta aatttctgat ccgtgaagcg   1440
tggaaggaaa tgaacactgt taccaccgct tccgattgtc ctttcaccga tgacctggtt   1500
gctgctgccg cgaatttggc tcgtgcagcg cagttcattt acctggatgg tgacgggcat   1560
ggcgtgcagc actctgaaat tcatcagcag atgggcggcc tgctgttcca accgtacgta   1620

<210> SEQ ID NO 14
<211> LENGTH: 540
<212> TYPE: PRT
<213> ORGANISM: Salvia officinalis

<400> SEQUENCE: 14

Met Arg Arg Ser Gly Asp Tyr Gln Pro Ser Leu Trp Asp Phe Asn Tyr

-continued

```
1               5                   10                  15

Ile Gln Ser Leu Asn Thr Pro Tyr Lys Glu Gln Arg His Phe Asn Arg
             20                  25                  30

Gln Ala Glu Leu Ile Met Gln Val Arg Met Leu Leu Lys Val Lys Met
             35                  40                  45

Glu Ala Ile Gln Gln Leu Glu Leu Ile Asp Asp Leu Gln Tyr Leu Gly
             50                  55                  60

Leu Ser Tyr Phe Phe Gln Asp Glu Ile Lys Gln Ile Leu Ser Ser Ile
65                   70                  75                  80

His Asn Glu Pro Arg Tyr Phe His Asn Asn Asp Leu Tyr Phe Thr Ala
                 85                  90                  95

Leu Gly Phe Arg Ile Leu Arg Gln His Gly Phe Asn Val Ser Glu Asp
                 100                 105                 110

Val Phe Asp Cys Phe Lys Ile Glu Lys Cys Ser Asp Phe Asn Ala Asn
                 115                 120                 125

Leu Ala Gln Asp Thr Lys Gly Met Leu Gln Leu Tyr Glu Ala Ser Phe
                 130                 135                 140

Leu Leu Arg Glu Gly Glu Asp Thr Leu Glu Leu Ala Arg Arg Phe Ser
145                  150                 155                 160

Thr Arg Ser Leu Arg Glu Lys Phe Asp Glu Gly Gly Asp Glu Ile Asp
                 165                 170                 175

Glu Asp Leu Ser Ser Trp Ile Arg His Ser Leu Asp Leu Pro Leu His
                 180                 185                 190

Trp Arg Val Gln Gly Leu Glu Ala Arg Trp Phe Leu Asp Ala Tyr Ala
                 195                 200                 205

Arg Arg Pro Asp Met Asn Pro Leu Ile Phe Lys Leu Ala Lys Leu Asn
                 210                 215                 220

Phe Asn Ile Val Gln Ala Thr Tyr Gln Glu Leu Lys Asp Ile Ser
225                  230                 235                 240

Arg Trp Trp Asn Ser Ser Cys Leu Ala Glu Lys Leu Pro Phe Val Arg
                 245                 250                 255

Asp Arg Ile Val Glu Cys Phe Phe Trp Ala Ile Ala Ala Phe Glu Pro
                 260                 265                 270

His Gln Tyr Ser Tyr Gln Arg Lys Met Ala Ala Val Ile Ile Thr Phe
                 275                 280                 285

Ile Thr Ile Ile Asp Asp Val Tyr Asp Val Tyr Gly Thr Ile Glu Glu
                 290                 295                 300

Leu Glu Leu Leu Thr Asp Met Ile Arg Arg Trp Asp Asn Lys Ser Ile
305                  310                 315                 320

Ser Gln Leu Pro Tyr Tyr Met Gln Val Cys Tyr Leu Ala Leu Tyr Asn
                 325                 330                 335

Phe Val Ser Glu Arg Ala Tyr Asp Ile Leu Lys Asp Gln His Phe Asn
                 340                 345                 350

Ser Ile Pro Tyr Leu Gln Arg Ser Trp Val Ser Leu Val Glu Gly Tyr
                 355                 360                 365

Leu Lys Glu Ala Tyr Trp Tyr Asn Gly Tyr Lys Pro Ser Leu Glu
370                  375                 380

Glu Tyr Leu Asn Asn Ala Lys Ile Ser Ile Ser Ala Pro Thr Ile Ile
385                  390                 395                 400

Ser Gln Leu Tyr Phe Thr Leu Ala Asn Ser Ile Asp Glu Thr Ala Ile
                 405                 410                 415

Glu Ser Leu Tyr Gln Tyr His Asn Ile Leu Tyr Leu Ser Gly Thr Ile
                 420                 425                 430
```

```
Leu Arg Leu Ala Asp Asp Leu Gly Thr Ser Gln His Glu Leu Glu Arg
        435                 440                 445

Gly Asp Val Pro Lys Ala Ile Gln Cys Tyr Met Asn Asp Thr Asn Ala
    450                 455                 460

Ser Glu Arg Glu Ala Val Glu His Val Lys Phe Leu Ile Arg Glu Ala
465                 470                 475                 480

Trp Lys Glu Met Asn Thr Val Thr Thr Ala Ser Asp Cys Pro Phe Thr
                485                 490                 495

Asp Asp Leu Val Ala Ala Ala Asn Leu Ala Arg Ala Ala Gln Phe
            500                 505                 510

Ile Tyr Leu Asp Gly Asp Gly His Gly Val Gln His Ser Glu Ile His
        515                 520                 525

Gln Gln Met Gly Gly Leu Leu Phe Gln Pro Tyr Val
    530                 535                 540
```

<210> SEQ ID NO 15
<211> LENGTH: 1608
<212> TYPE: DNA
<213> ORGANISM: Artificial Sequence
<220> FEATURE:
<223> OTHER INFORMATION: Synthetic polynucleotide for codon optimized
      Artemisia annua pinene synthase (PS-AANN, BR6-PS-AANN, QH6,
      (-)-beta-pinene synthase, monoterpene synthase, terpenoid
      biosynthase)

<400> SEQUENCE: 15

```
atgcgtcgta gtgcaaatta cgccccttca ctgtggagtt atgacttcgt tcaatcgctg      60
tcctcaaaat acaaggggga taactacatg gcgcgttcgc gcgcgttgaa aggtgtagtg     120
cgcactatga tcctggaagc gaatggcatc gaaaacccat tgtcattgct gaacctggtg     180
gacgacttgc agcgcttagg catttcatac catttcctgg acgagatctc caacgttctg     240
gaaaaaatct acctgaactt ctataaaagc ccggaaaaat ggactaacat ggacttgaat     300
ttacgttctc tgggcttccg cttactgcgt caacacggtt atcatattcc tcaggaaatc     360
tttaaggatt tcatcgatgt caacggcaat tttaaggtg atatcatcag tatgctgaat     420
ctgtatgaag cgtcgtacca ctcagtagaa gaggaatcca ttctggatga tgcccgcgaa     480
ttcaccacga atatctgaa agagaccctg gagaacattg aagatcaaaa cattgctttg     540 tcattagcc atgccttagt tttcccgctg cattggatgg ttccgcgcgt cgaaacgtca     600
tggtttattg aagtctaccc gaaaaaggtg ggcatgaatc cgacagtcct ggagtttgca     660
aaactggatt ttaatattct gcaagctgta catcaggagg atatgaagaa agcctcacgc     720
tggtggaaag aaacctgctg ggagaagttt ggcttcgctc gcgatcgtct ggtcgaaaac     780
tttatgtgga ccgtcgctga aactatttta ccgcactttc agaccggccg tggcgtcctg     840
acgaaagtga atgctatgat taccaccatt gacgacgttt atgatgtgta tggtactctg     900
ccagaactgg aactgtttac caacattgtt aattcttggg atatcaatgc gatcgatgaa     960
ctgccggatt atctgaaaat tgcttcctg gcgtgttaca atgccaccaa tgaactgagc    1020
tacaacaccc tgaccaacaa aggttttttt gttcatccat acttaaaaaa agcctggcag    1080
gacttgtgca cagctatat tattgaagct aagtggttta cgatggtta cactccgacg    1140 tttaacgaat tcattgaaaa cgcttacatg tccatcggga ttgcgccgat catccgtcac    1200
gcttacctgc tgactctgac atccgtgacg gaggaagcac tgcagcacat cgaacgtgcg    1260
gaatcaatga ttcgtaacgc gtgcctgatt gtgcgtctga ctaacgacat gggtacgtca    1320
```

```
agcgacgaac tggagcgtgg tgacattcct aagagcatcc agtgctacat gcacgaatcg   1380
ggtgcaaccg aaatggaagc tcgtgcttac atcaaacagt tcattgttga acgtggaaa    1440 aaattgaaca aggaacgtca agaaatcggt agcgaattcc acaagaatt cgttgattgc    1500 gtaattaatc tgccgcgcat gggtcacttc atgtatacgg atggtgataa acacggtaaa   1560
ccggacatgt tcaaaccgta tgtctttagt ctgttcgtga atcctatt                1608

<210> SEQ ID NO 16
<211> LENGTH: 536
<212> TYPE: PRT
<213> ORGANISM: Artemisia annua

<400> SEQUENCE: 16

Met Arg Arg Ser Ala Asn Tyr Ala Pro Ser Leu Trp Ser Tyr Asp Phe
1               5                   10                  15

Val Gln Ser Leu Ser Ser Lys Tyr Lys Gly Asp Asn Tyr Met Ala Arg
            20                  25                  30

Ser Arg Ala Leu Lys Gly Val Val Arg Thr Met Ile Leu Glu Ala Asn
        35                  40                  45

Gly Ile Glu Asn Pro Leu Ser Leu Leu Asn Leu Val Asp Asp Leu Gln
    50                  55                  60

Arg Leu Gly Ile Ser Tyr His Phe Leu Asp Glu Ile Ser Asn Val Leu
65                  70                  75                  80

Glu Lys Ile Tyr Leu Asn Phe Tyr Lys Ser Pro Glu Lys Trp Thr Asn
                85                  90                  95

Met Asp Leu Asn Leu Arg Ser Leu Gly Phe Arg Leu Leu Arg Gln His
            100                 105                 110

Gly Tyr His Ile Pro Gln Glu Ile Phe Lys Asp Phe Ile Asp Val Asn
        115                 120                 125

Gly Asn Phe Lys Gly Asp Ile Ile Ser Met Leu Asn Leu Tyr Glu Ala
    130                 135                 140

Ser Tyr His Ser Val Glu Glu Ser Ile Leu Asp Asp Ala Arg Glu
145                 150                 155                 160

Phe Thr Thr Lys Tyr Leu Lys Glu Thr Leu Glu Asn Ile Glu Asp Gln
                165                 170                 175

Asn Ile Ala Leu Phe Ile Ser His Ala Leu Val Phe Pro Leu His Trp
            180                 185                 190

Met Val Pro Arg Val Glu Thr Ser Trp Phe Ile Glu Val Tyr Pro Lys
        195                 200                 205

Lys Val Gly Met Asn Pro Thr Val Leu Glu Phe Ala Lys Leu Asp Phe
    210                 215                 220

Asn Ile Leu Gln Ala Val His Gln Glu Asp Met Lys Lys Ala Ser Arg
225                 230                 235                 240

Trp Trp Lys Glu Thr Cys Trp Glu Lys Phe Gly Phe Ala Arg Asp Arg
                245                 250                 255

Leu Val Glu Asn Phe Met Trp Thr Val Ala Glu Asn Tyr Leu Pro His
            260                 265                 270

Phe Gln Thr Gly Arg Gly Val Leu Thr Lys Val Asn Ala Met Ile Thr
        275                 280                 285

Thr Ile Asp Asp Val Tyr Asp Val Tyr Gly Thr Leu Pro Glu Leu Glu
    290                 295                 300

Leu Phe Thr Asn Ile Val Asn Ser Trp Asp Ile Asn Ala Ile Asp Glu
305                 310                 315                 320

Leu Pro Asp Tyr Leu Lys Ile Cys Phe Leu Ala Cys Tyr Asn Ala Thr
```

|       |       |       |       |       |       |       | 325   |       |       |       |       |       | 330   |       |       |       |       |       | 335   |       |       |
|-------|-------|-------|-------|-------|-------|-------|-------|-------|-------|-------|-------|-------|-------|-------|-------|-------|-------|-------|-------|-------|-------|

Asn Glu Leu Ser Tyr Asn Thr Leu Thr Asn Lys Gly Phe Phe Val His
            340                 345                 350

Pro Tyr Leu Lys Lys Ala Trp Gln Asp Leu Cys Asn Ser Tyr Ile Ile
        355                 360                 365

Glu Ala Lys Trp Phe Asn Asp Gly Tyr Thr Pro Thr Phe Asn Glu Phe
    370                 375                 380

Ile Glu Asn Ala Tyr Met Ser Ile Gly Ile Ala Pro Ile Ile Arg His
385                 390                 395                 400

Ala Tyr Leu Leu Thr Leu Thr Ser Val Thr Glu Glu Ala Leu Gln His
            405                 410                 415

Ile Glu Arg Ala Glu Ser Met Ile Arg Asn Ala Cys Leu Ile Val Arg
        420                 425                 430

Leu Thr Asn Asp Met Gly Thr Ser Ser Asp Glu Leu Glu Arg Gly Asp
    435                 440                 445

Ile Pro Lys Ser Ile Gln Cys Tyr Met His Glu Ser Gly Ala Thr Glu
450                 455                 460

Met Glu Ala Arg Ala Tyr Ile Lys Gln Phe Ile Val Glu Thr Trp Lys
465                 470                 475                 480

Lys Leu Asn Lys Glu Arg Gln Glu Ile Gly Ser Glu Phe Pro Gln Glu
            485                 490                 495

Phe Val Asp Cys Val Ile Asn Leu Pro Arg Met Gly His Phe Met Tyr
        500                 505                 510

Thr Asp Gly Asp Lys His Gly Lys Pro Asp Met Phe Lys Pro Tyr Val
    515                 520                 525

Phe Ser Leu Phe Val Asn Pro Ile
530                 535

<210> SEQ ID NO 17
<211> LENGTH: 1644
<212> TYPE: DNA
<213> ORGANISM: Artificial Sequence
<220> FEATURE:
<223> OTHER INFORMATION: Synthetic polynucleotide for codon optimized
      Ocimum basilicum fenchol synthase (FS-OBAS, BR7-FS-OBAS, FES,
      terpene synthase)

<400> SEQUENCE: 17
atgcgtcgta gtggtaatta ccagccttcc gcctgggatt tcaattatat ccaatctctt    60
aacaataatc actccaaaga gagcgtcat ttacagggta agctaaatt gatcgaggaa     120 gtcaagatgt tactggaaca agaaatggca gcggtacagc agctggaatt tatcgaggat    180
ttgaagaact tagggctgtc ttatttattc caagatgaga ttaagattat cttgaacagt    240
atctataacc atcacaaatg tttccacaac aaccatcagc aacgtaccga tgagaatgcg    300
gatttatact ttgtcgcatt gggtttccgt ttatttcgtc agcacggttt caaagtttct    360
caggaagtgt ttgattgctt taagaacgaa gaaggcagcg acttcattcc aaatctggcc    420
gaagatacca aggtttgct gcaactgtat gaagcgtctt acctggtacg tcaagacgaa    480
gatactctgg agatggcgcg tcaattctcc acgaagatct tgcagaagaa agtggaagag    540
aagatgatcg aagagaacct gctgtcatgg acttgtcata gcttagaatt accgctgcac    600
tggcgtgttc aacgtattga ggctaaatgg ttcttagatg cgtatgcgag caaaccggat    660
atgaacccga ttatctttga attggccaaa ctggaattta acattgctca ggcgttacaa    720 caggggggaat taaggatct gtctcgttgg tggaatgaca cgggcatcgc ggagaaactg    780

-continued

```
ccgtttgctc gtgaccgtat tgtagaagca cattattggg caattggcac gttagaacca    840
taccagtacc gttatcagcg tagtttgatc gcgaagatca ttgccctgac gactgtcgtt    900
gatgatgttt atgatgttta tggtactctg gacgaaccgc aactgtttac ggatgctatc    960
cgtcgttggg atattgaatc tattaaccaa ctgccacact atttgcaact gtgctacttg    1020
gcgatctaca actttgtcag tgaattagcg tatgatatct ccgtgataaa aggtttcaat    1080
tccctgccgt atctgcataa gagttggtta gatttggttg aagcatactt cttagaagct    1140
aagtggttcc acagcggtta taccctact ttggaagaat acctgaataa tagtaagatg    1200
acaattacat gtccggccat tgtttccgag atttacttcg cattcgcgaa cagtattgac    1260
aagacggagg tcgaatccgt gtacaaatat catgacatcc tgtacttgtc tggcatgctt    1320
ctgcgtctgc cggatgatct gggcaccact actttcgaaa tgaagcgtgg tgacgtagct    1380
aaagcgatcc agtgttacat gaaagaacac aatgccagtg aagaagaggc gcgtgaacac    1440
attcgtttcc tgatgcgtga agcctggaaa caaatgaata ccgccgccgc cgccaataac    1500
tgtccgtttg tgaatgactt tgtagtaggc gccgcgagct taggtcgtgt ggccaatttc    1560
gtttatgtgg aaggtgacgg tttcggtgta cagcactcta agatccatca acaaatggcg    1620
gaactgctgt tctacccgta tcag                                           1644
```

<210> SEQ ID NO 18
<211> LENGTH: 548
<212> TYPE: PRT
<213> ORGANISM: Ocimum basilicum

<400> SEQUENCE: 18

```
Met Arg Arg Ser Gly Asn Tyr Gln Pro Ser Ala Trp Asp Phe Asn Tyr
1               5                   10                  15

Ile Gln Ser Leu Asn Asn Asn His Ser Lys Glu Glu Arg His Leu Gln
            20                  25                  30

Gly Lys Ala Lys Leu Ile Glu Glu Val Lys Met Leu Leu Glu Gln Glu
        35                  40                  45

Met Ala Ala Val Gln Gln Leu Glu Phe Ile Glu Asp Leu Lys Asn Leu
    50                  55                  60

Gly Leu Ser Tyr Leu Phe Gln Asp Glu Ile Lys Ile Ile Leu Asn Ser
65                  70                  75                  80

Ile Tyr Asn His His Lys Cys Phe His Asn Asn His Gln Gln Arg Thr
                85                  90                  95

Asp Glu Asn Ala Asp Leu Tyr Phe Val Ala Leu Gly Phe Arg Leu Phe
            100                 105                 110

Arg Gln His Gly Phe Lys Val Ser Gln Glu Val Phe Asp Cys Phe Lys
        115                 120                 125

Asn Glu Glu Gly Ser Asp Phe Ile Pro Asn Leu Ala Glu Asp Thr Lys
    130                 135                 140

Gly Leu Leu Gln Leu Tyr Glu Ala Ser Tyr Leu Val Arg Gln Asp Glu
145                 150                 155                 160

Asp Thr Leu Glu Met Ala Arg Gln Phe Ser Thr Lys Ile Leu Gln Lys
                165                 170                 175

Lys Val Glu Glu Lys Met Ile Glu Glu Asn Leu Leu Ser Trp Thr Cys
            180                 185                 190

His Ser Leu Glu Leu Pro Leu His Trp Arg Val Gln Arg Ile Glu Ala
        195                 200                 205

Lys Trp Phe Leu Asp Ala Tyr Ala Ser Lys Pro Asp Met Asn Pro Ile
    210                 215                 220
```

Ile Phe Glu Leu Ala Lys Leu Glu Phe Asn Ile Ala Gln Ala Leu Gln
225                 230                 235                 240

Gln Gly Glu Leu Lys Asp Leu Ser Arg Trp Trp Asn Asp Thr Gly Ile
            245                 250                 255

Ala Glu Lys Leu Pro Phe Ala Arg Asp Arg Ile Val Glu Ala His Tyr
        260                 265                 270

Trp Ala Ile Gly Thr Leu Glu Pro Tyr Gln Tyr Arg Tyr Gln Arg Ser
    275                 280                 285

Leu Ile Ala Lys Ile Ile Ala Leu Thr Thr Val Val Asp Asp Val Tyr
290                 295                 300

Asp Val Tyr Gly Thr Leu Asp Glu Pro Gln Leu Phe Thr Asp Ala Ile
305                 310                 315                 320

Arg Arg Trp Asp Ile Glu Ser Ile Asn Gln Leu Pro His Tyr Leu Gln
                325                 330                 335

Leu Cys Tyr Leu Ala Ile Tyr Asn Phe Val Ser Glu Leu Ala Tyr Asp
            340                 345                 350

Ile Phe Arg Asp Lys Gly Phe Asn Ser Leu Pro Tyr Leu His Lys Ser
        355                 360                 365

Trp Leu Asp Leu Val Glu Ala Tyr Phe Leu Glu Ala Lys Trp Phe His
    370                 375                 380

Ser Gly Tyr Thr Pro Thr Leu Glu Glu Tyr Leu Asn Asn Ser Lys Met
385                 390                 395                 400

Thr Ile Thr Cys Pro Ala Ile Val Ser Glu Ile Tyr Phe Ala Phe Ala
                405                 410                 415

Asn Ser Ile Asp Lys Thr Glu Val Glu Ser Val Tyr Lys Tyr His Asp
            420                 425                 430

Ile Leu Tyr Leu Ser Gly Met Leu Leu Arg Leu Pro Asp Asp Leu Gly
        435                 440                 445

Thr Thr Thr Phe Glu Met Lys Arg Gly Asp Val Ala Lys Ala Ile Gln
    450                 455                 460

Cys Tyr Met Lys Glu His Asn Ala Ser Glu Glu Ala Arg Glu His
465                 470                 475                 480

Ile Arg Phe Leu Met Arg Glu Ala Trp Lys Gln Met Asn Thr Ala Ala
                485                 490                 495

Ala Ala Asn Asn Cys Pro Phe Val Asn Asp Phe Val Val Gly Ala Ala
            500                 505                 510

Ser Leu Gly Arg Val Ala Asn Phe Val Tyr Val Glu Gly Asp Gly Phe
        515                 520                 525

Gly Val Gln His Ser Lys Ile His Gln Gln Met Ala Glu Leu Leu Phe
    530                 535                 540

Tyr Pro Tyr Gln
545

<210> SEQ ID NO 19
<211> LENGTH: 1608
<212> TYPE: DNA
<213> ORGANISM: Artificial Sequence
<220> FEATURE:
<223> OTHER INFORMATION: Synthetic polynucleotide for codon optimized
      Salvia fruticosa cineole synthase (CS-SFRU, BR8-CS-SFRU, 1,8-
      cineole synthase, CinS1, terpene synthase)

<400> SEQUENCE: 19
atgcgtcgta ccggagggta tcaacctact ttgtgggatt tcagcactat tcaatcattt     60
gatagcgaat ataagaaga gaaacattta atgcgtgctg cgggcatgat tgatcaggtg    120

```
aagatgatgc ttcaagaaga agttgattct attcgtcgtt tggaactgat tgacgatttg    180
cgtcgtctgg ggatttcatg ccactttgaa cgtgaaatcg tggaaatctt gaactccaaa    240
tattacacga acaacgaaat tgacgagcgt gatctttaca gcaccgcatt gcgattccgt    300
ttattacgtc aatacgattt cagtgttagt caggaggtgt ttgattgctt taagaacgcc    360
aaaggtacgg actttaaacc tagtttagtt gatgatactc gtggtttact tcaactgtac    420
gaagcatcct ttcttagtgc ccagggcgag gaaaccttgc gtttagcgcg tgacttcgca    480
acgaagttct tgcagaaacg tgtgctggtg acaaagata ttaatttatt atcctctatt     540
gagcgtgcac tggaactgcc gactcactgg cgtgttcaaa tgccaaatgc acgttctttc    600
attgatgcct ataaacgtcg tccagacatg aacccaaccg tacttgaact ggcaaagttg    660
gatttcaata tggtccaagc acagtttcag caagaattaa aggaagccag tcgttggtgg    720
aacagtaccg gacttgttca tgagttgccc tttgttcgtg atcgtattgt ggagtgttac    780
tactggacga ctggcgtggt ggagcgtcgt cagcatggtt acgaacgtat catgttgacc    840
aagattaatg cactggttac gacgattgat gatgtattcg acatttatgg cacgcttgag    900
gagcttcagc tgttcaccac ggcgattcaa cgttgggaca tcgaatcaat gaagcaactg    960
ccgccttaca tgcagatctg ttaccttgct ttgtttaatt tcgtaaacga gatggcttat   1020
gacactcttc gtgataaagg cttcgattct actccttatc ttcgtaaagt ctgggtaggc   1080
ttaattgaaa gttacttgat tgaggccaaa tggtactata aaggccataa acctagttta   1140
gaagaataca tgaagaacag ttggattagt atcggcggca ttccaatctt aagtcactta   1200
ttcttccgtt tgactgactc tatcgaggaa gaagcagcag aaagtatgca caaatatcac   1260
gatattgttc gtgcaagctg cactatcttg cgtcttgccg acgatatggg gacttcccct   1320
gacgaagtgg aacgtggaga tgtaccaaag tccgtccaat gttatatgaa cgagaagaat   1380
gccagtgaag aagaggctcg tgaacacgtg cgtagcctta ttgaccaaac gtggaagatg   1440
atgaacaaag aaatgatgac gagttctttc tccaaatact tcgtcgaagt atctgctaac   1500
ttagcacgta tggcacagtg gatctaccaa catgagagtg atggctttgg tatgcaacac   1560
tccttagtga acaagatgct gcgtgactta ttatttcatc gttatgaa              1608
```

<210> SEQ ID NO 20
<211> LENGTH: 536
<212> TYPE: PRT
<213> ORGANISM: Salvia fruticosa

<400> SEQUENCE: 20

```
Met Arg Arg Thr Gly Gly Tyr Gln Pro Thr Leu Trp Asp Phe Ser Thr
1               5                   10                  15

Ile Gln Ser Phe Asp Ser Glu Tyr Lys Glu Lys His Leu Met Arg
            20                  25                  30

Ala Ala Gly Met Ile Asp Gln Val Lys Met Met Leu Gln Glu Glu Val
        35                  40                  45

Asp Ser Ile Arg Arg Leu Glu Leu Ile Asp Asp Leu Arg Arg Leu Gly
    50                  55                  60

Ile Ser Cys His Phe Glu Arg Glu Ile Val Glu Ile Leu Asn Ser Lys
65                  70                  75                  80

Tyr Tyr Thr Asn Asn Glu Ile Asp Glu Arg Asp Leu Tyr Ser Thr Ala
                85                  90                  95

Leu Arg Phe Arg Leu Leu Arg Gln Tyr Asp Phe Ser Val Ser Gln Glu
            100                 105                 110
```

```
Val Phe Asp Cys Phe Lys Asn Ala Lys Gly Thr Asp Phe Lys Pro Ser
            115                 120                 125

Leu Val Asp Asp Thr Arg Gly Leu Leu Gln Leu Tyr Glu Ala Ser Phe
130                 135                 140

Leu Ser Ala Gln Gly Glu Glu Thr Leu Arg Leu Ala Arg Asp Phe Ala
145                 150                 155                 160

Thr Lys Phe Leu Gln Lys Arg Val Leu Val Asp Lys Asp Ile Asn Leu
                165                 170                 175

Leu Ser Ser Ile Glu Arg Ala Leu Glu Leu Pro Thr His Trp Arg Val
                180                 185                 190

Gln Met Pro Asn Ala Arg Ser Phe Ile Asp Ala Tyr Lys Arg Arg Pro
                195                 200                 205

Asp Met Asn Pro Thr Val Leu Glu Leu Ala Lys Leu Asp Phe Asn Met
            210                 215                 220

Val Gln Ala Gln Phe Gln Gln Glu Leu Lys Glu Ala Ser Arg Trp Trp
225                 230                 235                 240

Asn Ser Thr Gly Leu Val His Glu Leu Pro Phe Val Arg Asp Arg Ile
                245                 250                 255

Val Glu Cys Tyr Tyr Trp Thr Thr Gly Val Val Glu Arg Arg Gln His
            260                 265                 270

Gly Tyr Glu Arg Ile Met Leu Thr Lys Ile Asn Ala Leu Val Thr Thr
            275                 280                 285

Ile Asp Asp Val Phe Asp Ile Tyr Gly Thr Leu Glu Glu Leu Gln Leu
            290                 295                 300

Phe Thr Thr Ala Ile Gln Arg Trp Asp Ile Glu Ser Met Lys Gln Leu
305                 310                 315                 320

Pro Pro Tyr Met Gln Ile Cys Tyr Leu Ala Leu Phe Asn Phe Val Asn
                325                 330                 335

Glu Met Ala Tyr Asp Thr Leu Arg Asp Lys Gly Phe Asp Ser Thr Pro
                340                 345                 350

Tyr Leu Arg Lys Val Trp Val Gly Leu Ile Glu Ser Tyr Leu Ile Glu
            355                 360                 365

Ala Lys Trp Tyr Tyr Lys Gly His Lys Pro Ser Leu Glu Glu Tyr Met
            370                 375                 380

Lys Asn Ser Trp Ile Ser Ile Gly Gly Ile Pro Ile Leu Ser His Leu
385                 390                 395                 400

Phe Phe Arg Leu Thr Asp Ser Ile Glu Glu Glu Ala Ala Glu Ser Met
                405                 410                 415

His Lys Tyr His Asp Ile Val Arg Ala Ser Cys Thr Ile Leu Arg Leu
                420                 425                 430

Ala Asp Asp Met Gly Thr Ser Leu Asp Glu Val Glu Arg Gly Asp Val
            435                 440                 445

Pro Lys Ser Val Gln Cys Tyr Met Asn Glu Lys Asn Ala Ser Glu Glu
            450                 455                 460

Glu Ala Arg Glu His Val Arg Ser Leu Ile Asp Gln Thr Trp Lys Met
465                 470                 475                 480

Met Asn Lys Glu Met Met Thr Ser Ser Phe Ser Lys Tyr Phe Val Glu
                485                 490                 495

Val Ser Ala Asn Leu Ala Arg Met Ala Gln Trp Ile Tyr Gln His Glu
                500                 505                 510

Ser Asp Gly Phe Gly Met Gln His Ser Leu Val Asn Lys Met Leu Arg
            515                 520                 525
```

Asp Leu Leu Phe His Arg Tyr Glu
    530                 535

<210> SEQ ID NO 21
<211> LENGTH: 61
<212> TYPE: DNA
<213> ORGANISM: Artificial Sequence
<220> FEATURE:
<223> OTHER INFORMATION: Synthetic oligonucleotide for MevMCS-F

<400> SEQUENCE: 21
gaattcataa gcttgtgagc ggccgcattg atgcatagct agcaggccgg ccaggtacca    60
c                                                                    61

<210> SEQ ID NO 22
<211> LENGTH: 61
<212> TYPE: DNA
<213> ORGANISM: Artificial Sequence
<220> FEATURE:
<223> OTHER INFORMATION: Synthetic oligonucleotide for MevMCS-R

<400> SEQUENCE: 22
cccgggtggt acctggccgg cctgctagct atgcatcaat gcggccgctc acaagcttat    60
g                                                                    61

<210> SEQ ID NO 23
<211> LENGTH: 589
<212> TYPE: PRT
<213> ORGANISM: Artificial Sequence
<220> FEATURE:
<223> OTHER INFORMATION: Synthetic polypeptide for terpene synthase
      consensus sequence
<220> FEATURE:
<221> NAME/KEY: VARIANT
<222> LOCATION: (21)..(21)
<223> OTHER INFORMATION: Xaa = Glu, Leu, Asn, Ile, Ser or Asp
<220> FEATURE:
<221> NAME/KEY: VARIANT
<222> LOCATION: (23)..(23)
<223> OTHER INFORMATION: Xaa = Lys, Asp, Pro, Thr, Asn or Glu
<220> FEATURE:
<221> NAME/KEY: VARIANT
<222> LOCATION: (25)..(25)
<223> OTHER INFORMATION: Xaa = Ala, Tyr, Lys, Ser or absent
<220> FEATURE:
<221> NAME/KEY: VARIANT
<222> LOCATION: (32)..(32)
<223> OTHER INFORMATION: Xaa = Glu, Ile, Asn, Asp, Glu, Arg, Gln or Met
<220> FEATURE:
<221> NAME/KEY: VARIANT
<222> LOCATION: (34)..(34)
<223> OTHER INFORMATION: Xaa = Asp, Ala, Gln, Glu, Lys, Gly, Arg or Lys
<220> FEATURE:
<221> NAME/KEY: VARIANT
<222> LOCATION: (36)..(36)
<223> OTHER INFORMATION: Xaa = Leu, Glu, Arg, Thr, Lys or Gly
<220> FEATURE:
<221> NAME/KEY: VARIANT
<222> LOCATION: (39)..(39)
<223> OTHER INFORMATION: Xaa = Lys, Thr, Met, Val, Gly, Glu or Asp
<220> FEATURE:
<221> NAME/KEY: VARIANT
<222> LOCATION: (40)..(40)
<223> OTHER INFORMATION: Xaa = Val, Leu, Gln or Glu
<220> FEATURE:
<221> NAME/KEY: VARIANT
<222> LOCATION: (46)..(46)
<223> OTHER INFORMATION: Xaa = Asp, Glu, Lys, Phe or Gln
<220> FEATURE:
<221> NAME/KEY: VARIANT
<222> LOCATION: (47)..(47)
<223> OTHER INFORMATION: Xaa = Glu, Lys, Val, Asn, Ala or Gln

```
-continued

<220> FEATURE:
<221> NAME/KEY: VARIANT
<222> LOCATION: (48)..(48)
<223> OTHER INFORMATION: Xaa = Gln, Glu, Lys, Phe, Ser or Asn
<220> FEATURE:
<221> NAME/KEY: VARIANT
<222> LOCATION: (49)..(49)
<223> OTHER INFORMATION: Xaa = Lys, Ile, Gly or absent
<220> FEATURE:
<221> NAME/KEY: VARIANT
<222> LOCATION: (50)..(50)
<223> OTHER INFORMATION: Xaa = Ser or absent
<220> FEATURE:
<221> NAME/KEY: VARIANT
<222> LOCATION: (51)..(51)
<223> OTHER INFORMATION: Xaa = Leu, Val or absent
<220> FEATURE:
<221> NAME/KEY: VARIANT
<222> LOCATION: (52)..(52)
<223> OTHER INFORMATION: Xaa = Glu or absent
<220> FEATURE:
<221> NAME/KEY: VARIANT
<222> LOCATION: (53)..(53)
<223> OTHER INFORMATION: Xaa = Asp or absent
<220> FEATURE:
<221> NAME/KEY: VARIANT
<222> LOCATION: (54)..(54)
<223> OTHER INFORMATION: Xaa = Gly, Ala or absent
<220> FEATURE:
<221> NAME/KEY: VARIANT
<222> LOCATION: (55)..(55)
<223> OTHER INFORMATION: Xaa = Gly or absent
<220> FEATURE:
<221> NAME/KEY: VARIANT
<222> LOCATION: (56)..(56)
<223> OTHER INFORMATION: Xaa = Glu or absent
<220> FEATURE:
<221> NAME/KEY: VARIANT
<222> LOCATION: (57)..(57)
<223> OTHER INFORMATION: Xaa = Leu or absent
<220> FEATURE:
<221> NAME/KEY: VARIANT
<222> LOCATION: (58)..(58)
<223> OTHER INFORMATION: Xaa = Ile or absent
<220> FEATURE:
<221> NAME/KEY: VARIANT
<222> LOCATION: (59)..(59)
<223> OTHER INFORMATION: Xaa = Thr or absent
<220> FEATURE:
<221> NAME/KEY: VARIANT
<222> LOCATION: (60)..(60)
<223> OTHER INFORMATION: Xaa = Pro or absent
<220> FEATURE:
<221> NAME/KEY: VARIANT
<222> LOCATION: (61)..(61)
<223> OTHER INFORMATION: Xaa = Leu, Ile or absent
<220> FEATURE:
<221> NAME/KEY: VARIANT
<222> LOCATION: (62)..(62)
<223> OTHER INFORMATION: Xaa = Lys, Thr, Met, Arg, Asn, Glu or Val
<220> FEATURE:
<221> NAME/KEY: VARIANT
<222> LOCATION: (64)..(64)
<223> OTHER INFORMATION: Xaa = Tyr, Gln, Ala, Pro, Leu or Ser
<220> FEATURE:
<221> NAME/KEY: VARIANT
<222> LOCATION: (75)..(75)
<223> OTHER INFORMATION: Xaa = Gln, Lys, Glu or Arg
<220> FEATURE:
<221> NAME/KEY: VARIANT
<222> LOCATION: (89)..(89)
<223> OTHER INFORMATION: Xaa = Asn, Glu, Gln, Thr, Ser or Ile
<220> FEATURE:
<221> NAME/KEY: VARIANT
<222> LOCATION: (92)..(92)
<223> OTHER INFORMATION: Xaa = Thr, Ser, Gly, Asp, Glu or Asn
<220> FEATURE:
<221> NAME/KEY: VARIANT
<222> LOCATION: (96)..(96)
```

```
<223> OTHER INFORMATION: Xaa = Lys, Leu, Asn, Ser or Tyr
<220> FEATURE:
<221> NAME/KEY: VARIANT
<222> LOCATION: (97)..(97)
<223> OTHER INFORMATION: Xaa = Asp, Glu, Tyr, His, Asn, Thr or absent
<220> FEATURE:
<221> NAME/KEY: VARIANT
<222> LOCATION: (98)..(98)
<223> OTHER INFORMATION: Xaa = His, Pro, Trp, Phe, Asn or absent
<220> FEATURE:
<221> NAME/KEY: VARIANT
<222> LOCATION: (100)..(100)
<223> OTHER INFORMATION: Xaa = Lys, Tyr, Trp, Cys or Glu
<220> FEATURE:
<221> NAME/KEY: VARIANT
<222> LOCATION: (101)..(101)
<223> OTHER INFORMATION: Xaa = Asp, Tyr, Phe, Leu, Lys, Glu, Ser or Ile
<220> FEATURE:
<221> NAME/KEY: VARIANT
<222> LOCATION: (102)..(102)
<223> OTHER INFORMATION: Xaa = Arg, Lys, His, Asp, Gly, Pro or absent
<220> FEATURE:
<221> NAME/KEY: VARIANT
<222> LOCATION: (104)..(104)
<223> OTHER INFORMATION: Xaa = Asn, Pro, Ser, Gly, Lys or absent
<220> FEATURE:
<221> NAME/KEY: VARIANT
<222> LOCATION: (105)..(105)
<223> OTHER INFORMATION: Xaa = Ile, Phe, Glu, Cys, Trp, His or absent
<220> FEATURE:
<221> NAME/KEY: VARIANT
<222> LOCATION: (106)..(106)
<223> OTHER INFORMATION: Xaa = Pro, Ala, Val, Gly, Gln or absent
<220> FEATURE:
<221> NAME/KEY: VARIANT
<222> LOCATION: (107)..(107)
<223> OTHER INFORMATION: Xaa = Lys, Arg, Gln or absent
<220> FEATURE:
<221> NAME/KEY: VARIANT
<222> LOCATION: (108)..(108)
<223> OTHER INFORMATION: Xaa = Glu, Arg or absent
<220> FEATURE:
<221> NAME/KEY: VARIANT
<222> LOCATION: (109)..(109)
<223> OTHER INFORMATION: Xaa = Ser, Thr or absent
<220> FEATURE:
<221> NAME/KEY: VARIANT
<222> LOCATION: (110)..(110)
<223> OTHER INFORMATION: Xaa = Asp or absent
<220> FEATURE:
<221> NAME/KEY: VARIANT
<222> LOCATION: (112)..(112)
<223> OTHER INFORMATION: Xaa = Glu, Lys, Val, Ala, Asn or absent
<220> FEATURE:
<221> NAME/KEY: VARIANT
<222> LOCATION: (113)..(113)
<223> OTHER INFORMATION: Xaa = Ser, Arg, Met, Thr, Ala or absent
<220> FEATURE:
<221> NAME/KEY: VARIANT
<222> LOCATION: (146)..(146)
<223> OTHER INFORMATION: Xaa = Lys, Ser, Ile, Gln, His, Asn, Thr or
      absent
<220> FEATURE:
<221> NAME/KEY: VARIANT
<222> LOCATION: (150)..(150)
<223> OTHER INFORMATION: Xaa = Asp, Glu, Ala, Thr, Cys, Gly or Pro
<220> FEATURE:
<221> NAME/KEY: VARIANT
<222> LOCATION: (154)..(154)
<223> OTHER INFORMATION: Xaa = Asp, Gln, Ser, Glu or absent
<220> FEATURE:
<221> NAME/KEY: VARIANT
<222> LOCATION: (157)..(157)
<223> OTHER INFORMATION: Xaa = Thr or absent
<220> FEATURE:
<221> NAME/KEY: VARIANT
<222> LOCATION: (158)..(159)
<223> OTHER INFORMATION: Xaa = Gly or absent
<220> FEATURE:
```

```
<221> NAME/KEY: VARIANT
<222> LOCATION: (160)..(160)
<223> OTHER INFORMATION: Xaa = Glu or absent
<220> FEATURE:
<221> NAME/KEY: VARIANT
<222> LOCATION: (161)..(161)
<223> OTHER INFORMATION: Xaa = Ile or absent
<220> FEATURE:
<221> NAME/KEY: VARIANT
<222> LOCATION: (175)..(175)
<223> OTHER INFORMATION: Xaa = Thr, Arg, Phe, Val or Ala
<220> FEATURE:
<221> NAME/KEY: VARIANT
<222> LOCATION: (176)..(176)
<223> OTHER INFORMATION: Xaa = Lys, Glu, Pro or Gln
<220> FEATURE:
<221> NAME/KEY: VARIANT
<222> LOCATION: (184)..(184)
<223> OTHER INFORMATION: Xaa = Phe, Asp or absent
<220> FEATURE:
<221> NAME/KEY: VARIANT
<222> LOCATION: (187)..(187)
<223> OTHER INFORMATION: Xaa = Pro, Glu, Arg, Ala, Thr, Ile, Gln or Asp
<220> FEATURE:
<221> NAME/KEY: VARIANT
<222> LOCATION: (200)..(200)
<223> OTHER INFORMATION: Xaa = His, Gly, Ile or absent
<220> FEATURE:
<221> NAME/KEY: VARIANT
<222> LOCATION: (200)..(200)
<223> OTHER INFORMATION: Xaa = His, Gly, Ile or absent
<220> FEATURE:
<221> NAME/KEY: VARIANT
<222> LOCATION: (201)..(201)
<223> OTHER INFORMATION: Xaa = Ser, Gly, Glu or absent
<220> FEATURE:
<221> NAME/KEY: VARIANT
<222> LOCATION: (202)..(202)
<223> OTHER INFORMATION: Xaa = Asn, Gly, Asp, Lys or absent
<220> FEATURE:
<221> NAME/KEY: VARIANT
<222> LOCATION: (203)..(203)
<223> OTHER INFORMATION: Xaa = Glu, Gly, Lys, Gln or Met
<220> FEATURE:
<221> NAME/KEY: VARIANT
<222> LOCATION: (205)..(205)
<223> OTHER INFORMATION: Xaa = Phe, Pro or absent
<220> FEATURE:
<221> NAME/KEY: VARIANT
<222> LOCATION: (206)..(206)
<223> OTHER INFORMATION: Xaa = Gly, Ala, Val or absent
<220> FEATURE:
<221> NAME/KEY: VARIANT
<222> LOCATION: (208)..(208)
<223> OTHER INFORMATION: Xaa = Cys, Gly, Glu, Ser, Ile or absent
<220> FEATURE:
<221> NAME/KEY: VARIANT
<222> LOCATION: (215)..(215)
<223> OTHER INFORMATION: Xaa = Val, Ala, Arg, Glu, Ser or Cys
<220> FEATURE:
<221> NAME/KEY: VARIANT
<222> LOCATION: (245)..(245)
<223> OTHER INFORMATION: Xaa = Lys, Asn or absent
<220> FEATURE:
<221> NAME/KEY: VARIANT
<222> LOCATION: (249)..(249)
<223> OTHER INFORMATION: Xaa = Met or absent
<220> FEATURE:
<221> NAME/KEY: VARIANT
<222> LOCATION: (250)..(250)
<223> OTHER INFORMATION: Xaa = Pro or absent
<220> FEATURE:
<221> NAME/KEY: VARIANT
<222> LOCATION: (251)..(251)
<223> OTHER INFORMATION: Xaa = Tyr or absent
<220> FEATURE:
<221> NAME/KEY: VARIANT
<222> LOCATION: (252)..(252)
<223> OTHER INFORMATION: Xaa = Thr or absent
```

-continued

```
<220> FEATURE:
<221> NAME/KEY: VARIANT
<222> LOCATION: (253)..(253)
<223> OTHER INFORMATION: Xaa = Asn or absent
<220> FEATURE:
<221> NAME/KEY: VARIANT
<222> LOCATION: (254)..(254)
<223> OTHER INFORMATION: Xaa = Ala, Val or absent
<220> FEATURE:
<221> NAME/KEY: VARIANT
<222> LOCATION: (255)..(255)
<223> OTHER INFORMATION: Xaa = Glu or absent
<220> FEATURE:
<221> NAME/KEY: VARIANT
<222> LOCATION: (256)..(256)
<223> OTHER INFORMATION: Xaa = Lys or absent
<220> FEATURE:
<221> NAME/KEY: VARIANT
<222> LOCATION: (274)..(274)
<223> OTHER INFORMATION: Xaa = Glu, Gln, Arg or Gly
<220> FEATURE:
<221> NAME/KEY: VARIANT
<222> LOCATION: (284)..(284)
<223> OTHER INFORMATION: Xaa = Met, Arg, Asn, Ser or Lys
<220> FEATURE:
<221> NAME/KEY: VARIANT
<222> LOCATION: (289)..(289)
<223> OTHER INFORMATION: Xaa = Gly, Val, Ala, Pro or Trp
<220> FEATURE:
<221> NAME/KEY: VARIANT
<222> LOCATION: (295)..(295)
<223> OTHER INFORMATION: Xaa = Ala, Val, Cys or Thr
<220> FEATURE:
<221> NAME/KEY: VARIANT
<222> LOCATION: (302)..(302)
<223> OTHER INFORMATION: Xaa = Asn, Cys, Ser, Tyr or Ala
<220> FEATURE:
<221> NAME/KEY: VARIANT
<222> LOCATION: (310)..(310)
<223> OTHER INFORMATION: Xaa = Ile, Phe, Ala, Asn, Leu or Val
<220> FEATURE:
<221> NAME/KEY: VARIANT
<222> LOCATION: (313)..(313)
<223> OTHER INFORMATION: Xaa = Pro, Arg, His, Asn or Tyr
<220> FEATURE:
<221> NAME/KEY: VARIANT
<222> LOCATION: (318)..(318)
<223> OTHER INFORMATION: Xaa = Val, Ala, Gln, Phe, Gly or Glu
<220> FEATURE:
<221> NAME/KEY: VARIANT
<222> LOCATION: (320)..(320)
<223> OTHER INFORMATION: Xaa = Gln, Ile, Lys, Leu, Phe, Gly or Ser
<220> FEATURE:
<221> NAME/KEY: VARIANT
<222> LOCATION: (326)..(326)
<223> OTHER INFORMATION: Xaa = Asn, Ile, Ser or Cys
<220> FEATURE:
<221> NAME/KEY: VARIANT
<222> LOCATION: (351)..(351)
<223> OTHER INFORMATION: Xaa = Ala, Leu, Met, Thr or Ile
<220> FEATURE:
<221> NAME/KEY: VARIANT
<222> LOCATION: (351)..(351)
<223> OTHER INFORMATION: Xaa = Ala, Leu, Met, Thr or Ile
<220> FEATURE:
<221> NAME/KEY: VARIANT
<222> LOCATION: (355)..(355)
<223> OTHER INFORMATION: Xaa = Phe or absent
<220> FEATURE:
<221> NAME/KEY: VARIANT
<222> LOCATION: (356)..(356)
<223> OTHER INFORMATION: Xaa = Ser or absent
<220> FEATURE:
<221> NAME/KEY: VARIANT
<222> LOCATION: (360)..(360)
<223> OTHER INFORMATION: Xaa = Asn, Lys, Glu or Ser
<220> FEATURE:
<221> NAME/KEY: VARIANT
<222> LOCATION: (394)..(394)
```

```
<223> OTHER INFORMATION: Xaa = Asn, Ile, Phe, Asp
<220> FEATURE:
<221> NAME/KEY: VARIANT
<222> LOCATION: (394)..(394)
<223> OTHER INFORMATION: Xaa = Asn, Ile, Phe or Asp
<220> FEATURE:
<221> NAME/KEY: VARIANT
<222> LOCATION: (422)..(422)
<223> OTHER INFORMATION: Xaa = Ala, Leu, Met, Thr or Ile
<220> FEATURE:
<221> NAME/KEY: VARIANT
<222> LOCATION: (430)..(430)
<223> OTHER INFORMATION: Xaa = Gln, Glu, Asn, Ser or Lys
<220> FEATURE:
<221> NAME/KEY: VARIANT
<222> LOCATION: (438)..(438)
<223> OTHER INFORMATION: Xaa = Ser, Gly, Ala, His, Ile or Cys
<220> FEATURE:
<221> NAME/KEY: VARIANT
<222> LOCATION: (440)..(440)
<223> OTHER INFORMATION: Xaa = Thr, Cys, Asn, Ala, Pro or Val
<220> FEATURE:
<221> NAME/KEY: VARIANT
<222> LOCATION: (444)..(444)
<223> OTHER INFORMATION: Xaa = His, Gln, Pro or Glu
<220> FEATURE:
<221> NAME/KEY: VARIANT
<222> LOCATION: (451)..(451)
<223> OTHER INFORMATION: Xaa = Asp, Asn, Ile or Thr
<220> FEATURE:
<221> NAME/KEY: VARIANT
<222> LOCATION: (452)..(452)
<223> OTHER INFORMATION: Xaa = Gln, Ser, Ala, Pro or absent
<220> FEATURE:
<221> NAME/KEY: VARIANT
<222> LOCATION: (454)..(454)
<223> OTHER INFORMATION: Xaa = Ser, Phe, Ile, Thr, His or Pro
<220> FEATURE:
<221> NAME/KEY: VARIANT
<222> LOCATION: (456)..(456)
<223> OTHER INFORMATION: Xaa = Gln, Lys, Glu, Thr or His
<220> FEATURE:
<221> NAME/KEY: VARIANT
<222> LOCATION: (457)..(457)
<223> OTHER INFORMATION: Xaa = Val, Glu, Thr, Trp, Ala or Ile
<220> FEATURE:
<221> NAME/KEY: VARIANT
<222> LOCATION: (464)..(464)
<223> OTHER INFORMATION: Xaa = His, Lys, Gln, Pro or Arg
<220> FEATURE:
<221> NAME/KEY: VARIANT
<222> LOCATION: (467)..(467)
<223> OTHER INFORMATION: Xaa = Asn, Asp, Ser or absent
<220> FEATURE:
<221> NAME/KEY: VARIANT
<222> LOCATION: (470)..(470)
<223> OTHER INFORMATION: Xaa = Arg, Tyr, Asn, Cys or Asp
<220> FEATURE:
<221> NAME/KEY: VARIANT
<222> LOCATION: (473)..(473)
<223> OTHER INFORMATION: Xaa = Ser, Gly or Cys
<220> FEATURE:
<221> NAME/KEY: VARIANT
<222> LOCATION: (486)..(486)
<223> OTHER INFORMATION: Xaa = Pro, Val, Gln, Tyr, Lys, Ser, Thr or Leu
<220> FEATURE:
<221> NAME/KEY: VARIANT
<222> LOCATION: (487)..(487)
<223> OTHER INFORMATION: Xaa = Asp, Glu, His or Phe
<220> FEATURE:
<221> NAME/KEY: VARIANT
<222> LOCATION: (505)..(505)
<223> OTHER INFORMATION: Xaa = Thr, Tyr, Arg, Asn, Ser, His or Lys
<220> FEATURE:
<221> NAME/KEY: VARIANT
<222> LOCATION: (506)..(506)
<223> OTHER INFORMATION: Xaa = Pro or absent
<220> FEATURE:
<221> NAME/KEY: VARIANT
```

```
<222> LOCATION: (530)..(530)
<223> OTHER INFORMATION: Xaa = Tyr, Ala, Thr, Trp or Lys
<220> FEATURE:
<221> NAME/KEY: VARIANT
<222> LOCATION: (535)..(535)
<223> OTHER INFORMATION: Xaa = His, Lys, Ser, Asp, Ala, Pro, Ile, Asn
      or absent
<220> FEATURE:
<221> NAME/KEY: VARIANT
<222> LOCATION: (536)..(536)
<223> OTHER INFORMATION: Xaa = Ser, Asp, Gly, Asn or absent
<220> FEATURE:
<221> NAME/KEY: VARIANT
<222> LOCATION: (537)..(537)
<223> OTHER INFORMATION: Xaa = Ser, Cys, Tyr, Asn or absent
<220> FEATURE:
<221> NAME/KEY: VARIANT
<222> LOCATION: (540)..(540)
<223> OTHER INFORMATION: Xaa = Leu, Pro or absent
<220> FEATURE:
<221> NAME/KEY: VARIANT
<222> LOCATION: (541)..(541)
<223> OTHER INFORMATION: Xaa = His, Gly, Thr, Ala, Pro, Ile, Val or Ser
<220> FEATURE:
<221> NAME/KEY: VARIANT
<222> LOCATION: (542)..(542)
<223> OTHER INFORMATION: Xaa = His, Lys, Asp, Thr, Ser, Gln or Asn
<220> FEATURE:
<221> NAME/KEY: VARIANT
<222> LOCATION: (546)..(546)
<223> OTHER INFORMATION: Xaa = Glu, Gly, Ala, Lys, Asp or Val
<220> FEATURE:
<221> NAME/KEY: VARIANT
<222> LOCATION: (547)..(547)
<223> OTHER INFORMATION: Xaa = Thr, Cys, Ala, Gly, His or Val
<220> FEATURE:
<221> NAME/KEY: VARIANT
<222> LOCATION: (560)..(560)
<223> OTHER INFORMATION: Xaa = Gln or absent
<220> FEATURE:
<221> NAME/KEY: VARIANT
<222> LOCATION: (561)..(561)
<223> OTHER INFORMATION: Xaa = Gln, His, Leu, Arg, Lys, Thr or Val
<220> FEATURE:
<221> NAME/KEY: VARIANT
<222> LOCATION: (572)..(572)
<223> OTHER INFORMATION: Xaa = Ala, Ile, Glu, Gly, Lys, Phe or Leu
<220> FEATURE:
<221> NAME/KEY: VARIANT
<222> LOCATION: (575)..(575)
<223> OTHER INFORMATION: Xaa = Val or absent
<220> FEATURE:
<221> NAME/KEY: VARIANT
<222> LOCATION: (577)..(577)
<223> OTHER INFORMATION: Xaa = Arg, Gln, His, Leu, Phe, Tyr or Met
<220> FEATURE:
<221> NAME/KEY: VARIANT
<222> LOCATION: (580)..(580)
<223> OTHER INFORMATION: Xaa = Ser, Arg, Gly, Ile, Glu or Asp
<220> FEATURE:
<221> NAME/KEY: VARIANT
<222> LOCATION: (587)..(587)
<223> OTHER INFORMATION: Xaa = Pro, Ala, Val, Thr, Gln, Glu or absent
<220> FEATURE:
<221> NAME/KEY: VARIANT
<222> LOCATION: (588)..(588)
<223> OTHER INFORMATION: Xaa = Leu or absent
<220> FEATURE:
<221> NAME/KEY: VARIANT
<222> LOCATION: (589)..(589)
<223> OTHER INFORMATION: Xaa = Asp or absent

<400> SEQUENCE: 23

Met Arg Arg Ser Gly Asn Tyr Gln Pro Ser Leu Trp Asp Phe Asn Phe
1               5                   10                  15

Ile Gln Ser Leu Xaa Ser Xaa Tyr Xaa Lys Glu Glu Arg His Leu Xaa
            20                  25                  30
```

```
Arg Xaa Ala Xaa Leu Ile Xaa Xaa Val Lys Met Leu Leu Xaa Xaa Xaa
        35              40                  45

Xaa Xaa Xaa Xaa Xaa Xaa Xaa Xaa Xaa Xaa Xaa Xaa Xaa Xaa Asp Xaa
50                  55                  60

Ile Gln Gln Leu Glu Leu Ile Asp Asp Leu Xaa Arg Leu Gly Leu Ser
65                  70                  75                  80

Tyr His Phe Gln Asp Glu Ile Lys Xaa Ile Leu Xaa Ser Ile Tyr Xaa
                85                  90                  95

Xaa Xaa Lys Xaa Xaa Xaa Asn Xaa Xaa Xaa Xaa Xaa Xaa Glu Xaa
            100                 105                 110

Xaa Asp Leu Tyr Ser Thr Ala Leu Gly Phe Arg Leu Leu Arg Gln His
        115                 120                 125

Gly Phe Asn Val Ser Gln Asp Val Phe Asp Cys Phe Lys Asn Glu Lys
    130                 135                 140

Gly Xaa Asp Phe Lys Xaa Ser Leu Ala Xaa Asp Thr Xaa Xaa Xaa Xaa
145                 150                 155                 160

Xaa Lys Gly Leu Leu Gln Leu Tyr Glu Ala Ser Phe Leu Ser Xaa Xaa
                165                 170                 175

Gly Glu Asp Thr Leu Glu Leu Xaa Ala Arg Xaa Phe Ala Thr Lys Tyr
            180                 185                 190

Leu Arg Glu Lys Val Asp Glu Xaa Xaa Xaa Xaa Ile Xaa Xaa Asp Xaa
        195                 200                 205

Asn Leu Leu Ser Trp Ile Xaa His Ser Leu Asp Leu Pro Leu His Trp
        210                 215                 220

Arg Val Gln Arg Leu Glu Ala Arg Trp Phe Ile Asp Ala Tyr Ala Arg
225                 230                 235                 240

Arg Pro Asp Met Xaa Asn Pro Leu Xaa Xaa Xaa Xaa Xaa Xaa Xaa
                245                 250                 255

Ile Leu Glu Leu Ala Lys Leu Asp Phe Asn Ile Val Gln Ala Leu His
            260                 265                 270

Gln Xaa Glu Leu Lys Asp Leu Ser Arg Trp Trp Xaa Asp Thr Gly Leu
    275                 280                 285

Xaa Glu Lys Leu Pro Phe Xaa Arg Asp Arg Ile Val Glu Xaa Tyr Phe
290                 295                 300

Trp Ala Ile Gly Ile Xaa Glu Pro Xaa Gln His Gly Tyr Xaa Arg Xaa
305                 310                 315                 320

Met Leu Ala Lys Ile Xaa Ala Leu Ile Thr Val Ile Asp Asp Val Tyr
            325                 330                 335

Asp Val Tyr Gly Thr Leu Asp Glu Leu Glu Leu Phe Thr Asp Xaa Ile
            340                 345                 350

Arg Arg Xaa Xaa Trp Asp Ile Xaa Ser Ile Asp Gln Leu Pro Glu Tyr
        355                 360                 365

Met Gln Leu Cys Tyr Leu Ala Leu Tyr Asn Phe Val Asn Glu Leu Ala
    370                 375                 380

Tyr Asp Ile Leu Lys Asp Lys Gly Phe Xaa Ser Ile Pro Tyr Leu Arg
385                 390                 395                 400

Lys Ser Trp Val Asp Leu Val Glu Ala Tyr Leu Ile Glu Ala Lys Trp
                405                 410                 415

Tyr Tyr Ser Gly Tyr Xaa Pro Ser Leu Glu Glu Tyr Leu Xaa Asn Ala
            420                 425                 430

Lys Ile Ser Ile Ala Xaa Pro Xaa Ile Ile Ser Xaa Leu Tyr Phe Thr
            435                 440                 445
```

-continued

```
Leu Ala Xaa Xaa Ser Xaa Asp Xaa Xaa Leu Ile Glu Ser Leu Tyr Xaa
    450             455             460
Tyr His Xaa Ile Leu Xaa Leu Ser Xaa Ile Ile Leu Arg Leu Ala Asp
465             470             475             480
Asp Leu Gly Thr Ser Xaa Xaa Glu Leu Ala Arg Gly Asp Val Pro Lys
            485             490                 495
Ser Ile Gln Cys Tyr Met Lys Asp Xaa Xaa Asn Ala Ser Glu Glu Glu
            500             505             510
Ala Arg Glu His Val Lys Phe Leu Ile Arg Glu Ala Trp Lys Glu Met
        515             520             525
Asn Xaa Glu Leu Leu Ala Xaa Xaa Xaa Pro Phe Xaa Xaa Xaa Asp Phe
    530             535             540
Val Xaa Xaa Ala Ala Asn Leu Gly Arg Met Ala Gln Phe Met Tyr Xaa
545             550             555             560
Xaa Glu Gly Asp Gly His Gly Val Gln His Ser Xaa Ile His Xaa Gln
            565             570             575
Xaa Met Ala Xaa Leu Leu Phe Glu Pro Tyr Xaa Xaa Xaa
            580             585
```